United States Patent [19]

Eckhouse

[11] Patent Number: 5,405,368
[45] Date of Patent: Apr. 11, 1995

[54] METHOD AND APPARATUS FOR THERAPEUTIC ELECTROMAGNETIC TREATMENT

[75] Inventor: Shimon Eckhouse, Haifa, Israel

[73] Assignee: ESC Inc., Newton, Mass.

[21] Appl. No.: 964,210

[22] Filed: Oct. 20, 1992

[51] Int. Cl.⁶ ............................................. A61N 5/06
[52] U.S. Cl. ..................................... 607/88; 607/90; 607/94; 606/3; 606/9
[58] Field of Search ............................. 607/88–89, 607/90–94; 606/3, 13, 2, 9–12, 17–19, 9

[56] References Cited

U.S. PATENT DOCUMENTS

| | | |
|---|---|---|
| 4,022,534 | 5/1977 | Kishner . |
| 4,298,005 | 11/1981 | Mutzhas . |
| 4,757,431 | 7/1988 | Cross et al. . |
| 4,784,135 | 11/1985 | Blum et al. ............................ 606/3 |
| 4,829,262 | 5/1989 | Furumoto . |
| 4,930,504 | 6/1990 | Diamantopoulos et al. ............ 606/3 |
| 5,161,526 | 11/1992 | Hellwing et al. ..................... 606/3 X |
| 5,207,671 | 5/1993 | Franken et al. ..................... 606/3 X |
| 5,217,455 | 6/1993 | Tan ..................................... 606/13 X |
| 5,259,380 | 11/1993 | Mendes et al. ....................... 606/9 X |

FOREIGN PATENT DOCUMENTS

3906860A1  9/1989  Germany .

Primary Examiner—Angela D. Sykes
Attorney, Agent, or Firm—Foley & Lardner

[57] ABSTRACT

A therapeutic treatment device includes a housing and an incoherent light source such as a flashlamp disposed in the housing. The flashlamp provides a pulsed light output for treatment of external skin disorders. To provide light to the treatment area the housing has an opening that is disposed adjacent a skin treatment area. A reflector is mounted within the housing near proximate the light source to reflect the light to the treatment area. At least one optical filter and an iris are mounted near the opening in the housing. Power to the lamp is provided by a pulse forming circuit that can provide a variable pulse width.

18 Claims, 4 Drawing Sheets

METHOD AND APPARATUS FOR THERAPEUTIC ELECTROMAGNETIC TREATMENT

FIELD OF THE INVENTION

The present invention relates generally to the art of therapeutic electromagnetic treatment and more specifically to a method and apparatus for utilizing a spatially extended pulsed light source such as a flashlamp (flash tube) for such a treatment or, efficiently focusing light from the flashlamp into optical fibers for therapeutic treatment or other applications.

BACKGROUND OF THE INVENTION

It is known in the prior art to use electromagnetic radiation in medical application for therapeutic uses such as treatment of skin disorders. For example, U.S. Pat. No. 4,298,005 to Mutzhas describes a continuous ultraviolet lamp with cosmetic, photobiological, and photochemical applications. A treatment based on using the UV portion of the spectrum and its photochemical interaction with the skin is described. The power delivered to the skin using Mutzhas' lamp is described as 150 W/m$^2$, which does not have a significant effect on skin temperature.

In addition to prior art treatment involving UV light, lasers have been used for dermatological procedures, including Argon lasers, $CO_2$ lasers, Nd(Yag) lasers, Copper vapor lasers, ruby lasers and dye lasers. For example, U.S. Pat. No. 4,829,262 to Furumoto, describes a method of constructing a dye laser used in dermatology applications. Two skin conditions which may be treated by laser radiation are external skin irregularities such as local differences in the pigmentation or structure of the skin, and vascular disorders lying deeper under the skin which cause a variety of skin abnormalities including port wine stains, telangiectasias, leg veins and cherry and spider angiomas. Laser treatment of these skin disorders generally includes localized heating of the treatment area by absorption of laser radiation. Heating the skin changes or corrects the skin disorder and causes the full or partial disappearance of the skin abnormality.

Certain external disorders such as pigmented lesions can also be treated by heating the skin very fast to a high enough temperature to evaporate parts of the skin. Deeper-lying vascular disorders are more typically treated by heating the blood to a high enough temperature to cause it to coagulate. The disorder will then eventually disappear. To control the treatment depth a pulsed radiation source is often used. The depth the heat penetrates in the blood vessel is controlled by controlling the pulse width of the radiation source. The absorption and scattering coefficients of the skin also affect the heat penetration. These coefficients are a function of the constituents of skin and the wavelength of the radiation. Specifically, the absorption coefficient of light in the epidermis and dermis tends to be a slowly varying, monotonically decreasing function of wavelength. Thus, the wavelength of the light should be chosen so that the absorption coefeicient is optimized for the particular skin condition and vessel size being treated.

The effectiveness of lasers for applications such as tattoo removal and removal of birth and age marks is diminished because lasers are monochromatic. A laser of a given wavelength may be effectively used to treat a first type of skin pigmentation disorder, but, if the specific wavelength of the laser is not absorbed efficiently by skin having a second type of disorder, it will be ineffective for the second type of skin disorder. Also, lasers are usually complicated, expensive to manufacture, large for the amount of power delivered, unreliable and difficult to maintain.

The wavelength of the light also affects vascular disorder treatment because blood content in the vicinity of the vascular disorders varies, and blood content affects the absorption coefficient of the treatment area. Oxyhemoglobin is the main chromophore which controls the optical properties of blood and has strong absorption bands in the visible region. More particularly, the strongest absorption peak of oxyhemoglobin occurs at 418 nm and has a band-width of 60 nm. Two additional absorption peaks with lower absorption coefficients occur at 542 and 577 nm. The total band-width of these two peaks is on the order of 100 nm. Additionally, light in the wavelength range of 500 to 600 nm is desirable for the treatment of blood vessel disorders of the skin since it is absorbed by the blood and penetrates through the skin. Longer wavelengths up to 1000 nm are also effective since they can penetrate deeper into the skin, heat the surrounding tissue and, if the pulse-width is long enough, contribute to heating the blood vessel by thermal conductivity. Also, longer wavelengths are effective for treatment of larger diameter vessels because the lower absorption coefficient is compensated for by the longer path of light in the vessel.

Accordingly, a wide band electromagnetic radiation source that covers the near UV and the visible portion of the spectrum would be desirable for treatment of external skin and vascular disorders. The overall range of wavelengths of the light source should be sufficient to optimize treatment for any of a number of applications. Such a therapeutic electromagnetic radiation device should also be capable of providing an optimal wavelength range within the overall range for the specific disorder being treated. The intensity of the light should be sufficient to cause the required thermal effect by raising the temperature of the treatment area to the required temperature. Also, the pulse-width should be variable over a wide enough range so as to achieve the optimal penetration depth for each application. Therefore, it is desirable to provide a light source having a wide range of wavelengths, which can be selected according to the required skin treatment, with a controlled pulse-width and a high enough energy density for application to the affected area.

Pulsed non-laser type light sources such as linear flashlamps provide these benefits. The intensity of the emitted light can be made high enough to achieve the required thermal effects. The pulse-width can be varied over a wide range so that control of thermal depth penetration can be accomplished. The typical spectrum covers the visible and ultraviolet range and the optical bands most effective for specific applications can be selected, or enhanced using fluorescent materials. Moreover, non-laser type light sources such as flashlamps are much simpler and easier to manufacture than lasers, are significantly less expensive for the same output power and have the potential of being more efficient and more reliable. They have a wide spectral range that can be optimized for a variety of specific skin treatment applications. These sources also have a pulse length that can be varied over a wide range which is critical for the different types of skin treatments.

In addition to being used for treating skin disorders, lasers have been used for invasive medical procedures such as lithotripsy and removal of blood vessel blockage. In such invasive procedures laser light is coupled to optical fibers and delivered through the fiber to the treatment area. In lithotripsy the fiber delivers light from a pulsed laser to a kidney or gallstone and the light interaction with the stone creates a shock wave which pulverizes the stone. To remove blood vessel blockage the light is coupled to the blockage by the fiber and disintegrates the blockage. In either case the shortcomings of lasers discussed above with respect to laser skin treatment are present. Accordingly, a treatment device for lithotripsy and blockage removal utilizing a flashlamp would be desirable.

To effectively treat an area the light from the source must be focussed on the treatment area. Coupling pulsed laser light into optical fibers in medicine is quite common. The prior art describes coupling isotropic incoherent point sources such as CW lamps into small optical fibers. For example, U.S. Pat. No. 4,757,431, issued Jul. 12, 1988, to Cross, et al. discloses a method for focusing incoherent point sources with small filaments or an arc lamp with an electrode separation of 2 mm into a small area. Point (or small) sources are relatively easy to focus without large losses in energy because of the small size of the source. Also, U.S. Pat. No. 4,022,534, issued May 10, 1977, to Kishner discloses light produced by a flash tube and the collection of only a small portion of the light emitted by the tube into an optical fiber.

However, the large dimension of an extended source such as a flashlamp make it difficult to focus large fractions of its energy into small areas. Coupling into optical fibers is even more difficult since not only must a high energy density be achieved, but the angular distribution of the light has to be such that trapping in the optical fiber can be accomplished. Thus, it is desirable to have a system for coupling the output of a high intensity, extended, pulsed light source into an optical fiber.

SUMMARY OF THE PRESENT INVENTION

According to a first embodiment of the invention a therapeutic treatment device comprises a housing and an incoherent light source, suitably a flashlamp, operable to provide a pulsed light output for treatment, disposed in the housing. The housing has an opening and is suitable for being disposed adjacent a skin treatment area. A reflector is mounted within the housing proximate the light source, and at least one optical filter is mounted proximate the opening in the housing. An iris is mounted coextensively with the opening. Power to the lamp is provided by a variable pulse width pulse forming circuit. Thus, the treatment device provides controlled density, filtered, pulsed light output through an opening in the housing to a skin area for treatment.

According to a second embodiment of the invention a method of treatment with light energy comprises the steps of providing a high power, pulsed light output from a non-laser, incoherent light source and directing the pulsed light output to a treatment area. The pulse width of the light output is controlled and focussed so that the power density of the light is controlled. Also, the light is filtered to control the spectrum of the light.

According to a third embodiment of the invention a coupler comprises an incoherent light source such as a toroidal flashlamp. A reflector is disposed around the incoherent light source and at least one optical fiber or light guide. The fiber has an end disposed within the reflector. This end collects the light from the circular lamp. In a similar coupling configuration fibers may be provided, along with a linear to circular fiber transfer unit disposed to receive light from the light source and provide light to the optical fibers. The reflector has an elliptical cross-section in a plane parallel to the axis of the linear flash tube, and the linear flash tube is located at one focus of the ellipse while the linear to circular transfer unit is located at the other focus of the ellipse.

BRIEF DESCRIPTION OF THE DRAWINGS

For a better understanding of the invention, reference is made to the accompanying drawings, in which like numerals designate corresponding elements or sections throughout, and in which.

In the various figures, like reference numerals are used to describe like components.

DETAILED DESCRIPTION OF THE PREFERRED EMBODIMENTS

Figure 1:
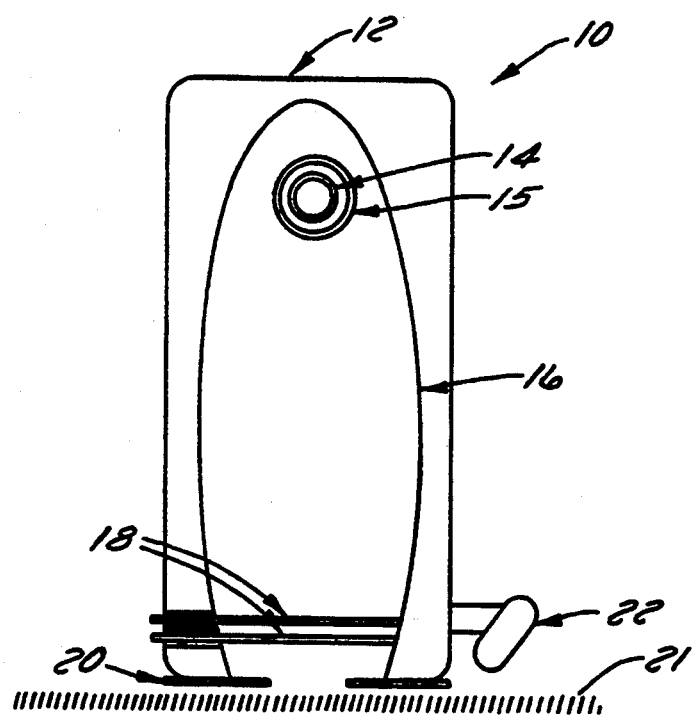
FIG. 1 is a cross-sectional view of an incoherent, pulsed light source skin treatment device.

Before explaining at least one embodiment of the invention in detail it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
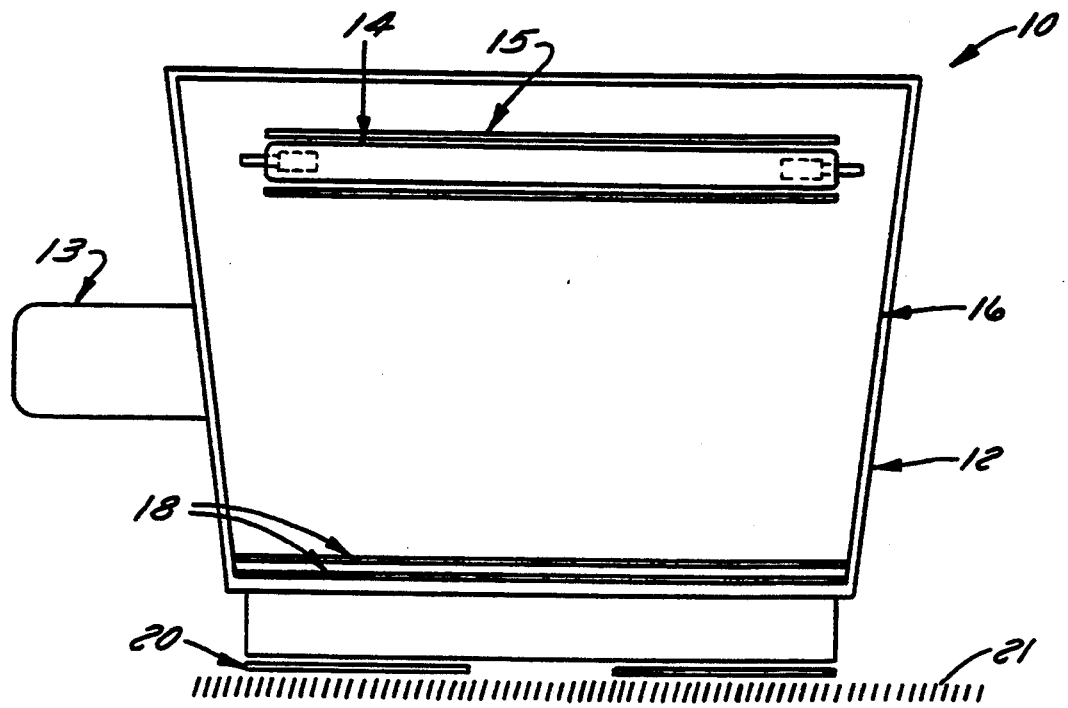
FIG. 2 is a side view of the light source of FIG. 1.

Referring now to FIGS. 1 and 2, cross-sectional and side views of an incoherent, pulsed light source skin treatment device 10 constructed and operated in accordance with the principles of the present invention are shown. The device 10 may be seen to include a housing 12, having an opening therein, a handle 13 (FIG. 2 only), a light source 14 having an outer glass tube 15, an elliptical reflector 16, a set of optical filters 18, an iris 20 and a detector 22 (FIG. 1 only).

Light source 14, which is mounted in housing 12, may be a typical incoherent light source such as a gas filled linear flashlamp Model No. L5568 available from ILC.

The spectrum of light emitted by gas filled linear flashlamp 14 depends on current density, type of glass envelope material and gas mixture used in the tube. For large current densities (e.g., 3000 A/Cm$^2$ or more) the spectrum is similar to a black body radiation spectrum. Typically, most of the energy is emitted in the 300 to 1000 nm wavelength range.

To treat a skin (or visible) disorder a required light density on the skin must be delivered. This light density can be achieved with the focusing arrangement shown in FIGS. 1 and 2. FIG. 1 shows a cross-section view of reflector 16, also mounted in housing 12. As shown in FIG. 1, the cross-section of reflector 16 in a plane is perpendicular to the axis of flashlamp 14 is an ellipse. Linear flashlamp 14 is located at one focus of the ellipse and reflector 16 is positioned in such a way that the treatment area of skin 21 is located at the other focus. The arrangement shown is similar to focusing arrangements used with lasers and efficiently couples light from flashlamp 14 to the skin. This arrangement should not, however, be considered limiting. Elliptical reflector 16 may be a metallic reflector, typically polished aluminum which is an easily machinable reflector and has a very high reflectivity in the visible, and the UV range of the spectrum can be used. Other bare or coated metals can also be used for this purpose.

Optical and neutral density filters 18 are mounted in housing 12 near the treatment area and may be moved into the beam or out of the beam to control the spectrum and intensity of the light. Typically, 50 to 100 nm bandwidth filters, as well as low cutoff filters in the visible and ultraviolet portions of the spectrum, are used. In some procedures it is desirable to use most of the spectrum, with only the UV portion being cut off. In other applications, mainly for deeper penetration, it is preferable to use narrower bandwidths. The bandwidth filters and the cutoff filters are readily available commercially.

Glass tube 15 is located coaxially with flashlamp 14 and has fluorescent material deposited on it. Glass tube 15 will typically be used for treatment of coagulation of blood vessels to optimize the energy efficiency of device 10. The fluorescent material can be chosen to absorb the UV portion of the spectrum of flashlamp 14 and generate light in the 500 to 650 nm range that is optimized for absorption in the blood. Similar materials are coated on the inner walls of commercial fluorescent lamps. A typical material used to generate "warm" white light in fluorescent lamps has a conversion efficiency of 80%, has a peak emission wavelength of 570 nm and has a bandwidth of 70 nm and is useful for absorption in blood. The few millisecond decay time of these phosphors is consistent with long pulses that are required for the treatment of blood vessels.

Other shapes or configurations of flashlamp 14 such as circular, helical, short arc and multiple linear flashlamps may be used. Reflector 16 may have other designs such as parabolic or circular reflectors. The light source can also be used without a reflector and the required energy and power density may be achieved by locating light source 14 in close proximity to the treatment area.

Iris 20 is mounted in housing 12 between optical filters 18 and the treatment area and controls the length and the width of the exposed area, i.e. by collimating the output of flashlamp 14. The length of flashlamp 14 controls the maximum length that can be exposed. Typically a 8 cm long (arc length) tube will be used and only the central 5 cm of the tube is exposed. Using the central 5 cm assures a high degree of uniformity of energy density in the exposed skin area. Thus, in this embodiment the iris 20 (also called a collimator) will enable exposure of skin areas of a maximum length of 5 cm. The iris 20 may be closed to provide a minimum exposure length of one millimeter. Similarly, the width of the exposed skin area can be controlled in the range of 1 to 5 mm for a 5 mm wide flashlamp. Larger exposed areas can be easily achieved by using longer flash tubes or multiple tubes, and smaller exposure areas are obtainable with an iris that more completely collimates the beam. The present invention provides a larger exposure area compared to prior art lasers or point sources and is very effective in the coagulation of blood vessels since blood flow interruption over a longer section of the vessel is more effective in coagulating it. The larger area exposed simultaneously also reduces the required procedure time.

Detector 22 (FIG. 1) is mounted outside housing 12 and monitors the light reflected from the skin. Detector 22 combined with optical filters 18 and neutral density filters can be used to achieve a quick estimate of the spectral reflection and absorption coefficients of the skin. This may be carried out at a low energy density level prior to the application of the main treatment pulse. Measurement of the optical properties of the skin prior to the application of the main pulse is useful to determine optimal treatment conditions. As stated above, the wide spectrum of the light emitted from the non-laser type source enables investigation of the skin over a wide spectral range and choice of optimal treatment wavelengths.

In an alternative embodiment, detector 22 or a second detector system may be used for real-time temperature measurement of the skin during its exposure to the pulsed light source. This is useful for skin thermolysis applications with long pulses in which light is absorbed in the epidermis and dermis. When the external portion of the epidermis reaches too high a temperature, permanent scarring of the skin may result. Thus, the temperature of the skin should be measured. This can be realized using infra-red emission of the heated skin, to prevent over-exposure.

A typical real-time detector system would measure the infra-red emission of the skin at two specific wavelengths by using two detectors and filters. The ratio between the signals of the two detectors can be used to estimate the instantaneous skin-temperature. The operation of the pulsed light source can be stopped if a preselected skin temperature is reached. This measurement is relatively easy since the temperature threshold for pulsed heating that may cause skin scarring is on the order of 50° C. or more, which is easily measurable using infra-red emission.

The depth of heat penetration depends on the light absorption and scattering in the different layers of the skin and the thermal properties of the skin. Another important parameter is pulse-width. For a pulsed light source, the energy of which is absorbed in an infinitesimally thin layer, the depth of heat penetration (d) by thermal conductivity during the pulse can be written as shown in Equation 1:

$$d = 4[k\Delta t / Cp]^{\frac{1}{2}} \qquad \text{(Eq. 1)}$$

where k=heat conductivity of the material being illuminated;
Δt=the pulse-width of the light pulse;
C=the heat capacity of the material;
ρ=density of the material.

It is clear from Equation 1 that the depth of heat penetration can be controlled by the pulse-width of the light source. Thus, a variation of pulse-width in the range of $10^{-5}$ sec to $10^{-1}$ sec will result in a variation in the thermal penetration by a factor of 100.

Accordingly, the flashlamp 14 provides a pulse width of from $10^{-5}$ sec to $10^{-1}$ sec. For treatment of vascular disorders in which coagulation of blood vessels in the skin is the objective the pulse length is chosen to uniformly heat as much of the entire thickness of the vessel as possible to achieve efficient coagulation. Typical blood vessels that need to be treated in the skin have thicknesses in the range of 0.5 mm. Thus, the optimal pulse-width, taking into account the thermal properties of blood, is on the order of 100 msec. If shorter pulses are used, heat will still be conducted through the blood to cause coagulation, however, the instantaneous temperature of part of the blood in the vessel and surrounding tissue will be higher than the temperature required for coagulation and may cause unwanted damage.

For treatment of external skin disorders in which evaporation of the skin is the objective, a very short pulse-width is used to provide for very shallow thermal penetration of the skin. For example, a $10^{-5}$ sec pulse will penetrate (by thermal conductivity) a depth of the order of only 5 microns into the skin. Thus, only a thin layer of skin is heated, and a very high, instantaneous temperature is obtained so that the external mark on the skin is evaporated.

Figure 3:
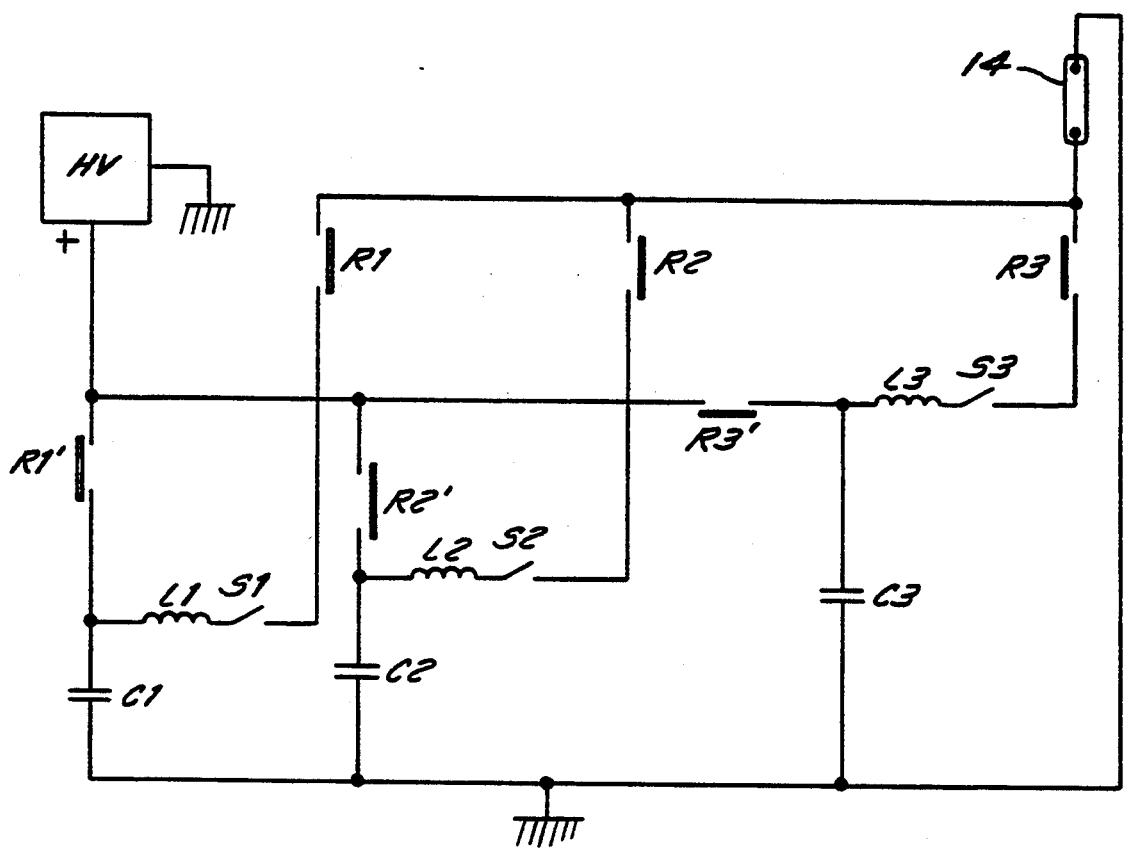
FIG. 3 is a schematic diagram of a pulse forming network with a variable pulse width for use with the skin treatment device of FIGS. 1 and 2.

FIG. 3 shows a variable pulse-width pulse forming circuit comprised of a plurality of individual pulse forming networks (PFN's) that create the variation in pulse-widths of flashlamp 14. The light pulse full width at half maximum (FWHM) of a flashlamp driven by a single element PFN with capacitance C and inductance L is approximately equal to:

$$\Delta t \approx 2[LC]^{\frac{1}{2}} \quad (Eq. 2)$$

Flashlamp 14 may be driven by three different PFN's, as shown in FIG. 3. The relay contacts R1', R2' and R3' are used to select among three capacitors C1, C2 and C3 that are charged by the high voltage power supply. Relays R1, R2 and R3 are used to select the PFN that will be connected to flashlamp 14. The high voltage switches S1, S2 and S3 are used to discharge the energy stored in the capacitor of the PFN into flashlamp 14. In one embodiment L1, L2 and L3 have values of 100 mH, 1 mH and 5 mH, respectively, and C1, C2 and C3 have values of 100 mF, 1 mF and 10 mF, respectively.

In addition to the possibility of firing each PFN separately, which generates the basic variability in pulse-width, additional variation can be achieved by firing PFN's sequentially. If, for example, two PFN's having pulse-width Δt1 and Δt2 are fired, so that the second PFN is fired after the first pulse has decayed to half of its amplitude, then an effective light pulse-width of this operation of the system will be given by the relation: Δt≈Δt1+Δt2.

The charging power supply typically has a voltage range of 500 V to 5 kV. The relays should therefore be high voltage relays that can isolate these voltages reliably. The switches S are capable of carrying the current of flashlamp 14 and to isolate the reverse high voltage generated if the PFNs are sequentially fired. Solid-state switches, vacuum switches or gas switches can be used for this purpose.

A simmer power supply (not shown in FIG. 3) may be used to keep the flashlamp in a low current conducting mode. Other configurations can be used to achieve pulse-width variation, such as the use of a single PFN and a crowbar switch, or use of a switch with closing and opening capabilities.

Typically, for operation of flashlamp 14 with an electrical pulse-width of 1 to 10 msec, a linear electrical energy density input of 100 to 300 J/cm can be used. An energy density of 30 to 100 J/cm² can be achieved on the skin for a typical flashlamp bore diameter of 5 mm. The use of a 500 to 650 nm bandwidth transmits 20% of the incident energy. Thus, energy densities on the skin of 6 to 20 J/cm² are achieved. The incorporation of the fluorescent material will further extend the output radiation in the desired range, enabling the same exposure of the skin with a lower energy input into flashlamp 14.

Pulsed laser skin treatment shows that energy densities in the range of 0.5 to 10 J/cm² with pulse-widths in the range of 0.5 msec are generally effective for treating vascular related skin disorders. This range of parameters falls in the range of operation of pulsed non-laser type light sources such as the linear flashlamp. A few steps of neutral density glass filters 18 can also be used to control the energy density on the skin.

For external disorders a typical pulse-width of 5 microsecond is used. A 20 J/cm electrical energy density input into a 5 mm bore flashlamp results in an energy density on the skin of 10 J/cm². Cutting off the hard UV portion of the spectrum results in 90% energy transmission, or skin exposure to an energy density of close to 10 J/cm². This energy density is high enough to evaporate external marks on the skin.

Device 10 can be provided as two units: a lightweight unit held by a physician using handle 13, with the hand-held unit containing flashlamp 14, filters 18 and iris 20 that together control the spectrum and the size of the exposed area and the detectors that measure the reflectivity and the instantaneous skin temperature. The power supply, the PFN's and the electrical controls are contained in a separate box (not shown) that is connected to the hand-held unit via a flexible cable. This enables ease of operation and easy access to the areas of the skin that need to be treated.

The invention has thus far been described in conjunction with skin treatment. However, using a flashlamp rather than a laser in invasive treatments provides advantages as well. Procedures such as lithotripsy or removal of blood vessel blockage may be performed with a flashlamp. Such a device may be similar to that shown in FIGS. 1 and 2, and may use the electronics of FIG. 3 to produce the flash. However, to properly couple the light to an optical fiber a number of couplers 40, 80 and 90 are shown in FIGS. 4 and 8–10, respectively.

Coupler 40 includes an optical source of high intensity incoherent and isotropic pulsed light such as a linear flash tube 42, a light reflector 44 which delivers the light energy to an optical fiber 46. The latter has a generally conical edge in the embodiment of FIG. 4. Optical fiber 46 transfers the light from light collection system 44 to the treatment area. In general, coupler 40 couples pulsed light from a flash tube into an optical fiber and has applications in medical, industrial and domestic areas.

For example, coupler 40 may be used in material processing to rapidly heat or ablate a portion of a material being processed, or to induce a photo-chemical process. Alternatively, coupler 40 may be used in a photography application to provide a flash for picture taking. Using such a coupler would allow the flash bulb to be located inside the camera, with the light transmitted to outside the camera using an optical fiber. As one skilled in the art should recognize coupler 40 allows the use of incoherent light in many applications that coherent or incoherent light has been used in the past.

Figure 5:
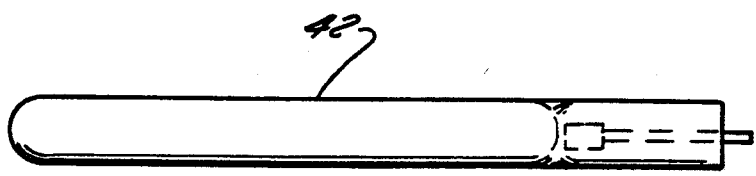
FIG. 5 is a side view of a toroidal flash tube.
Figure 6:
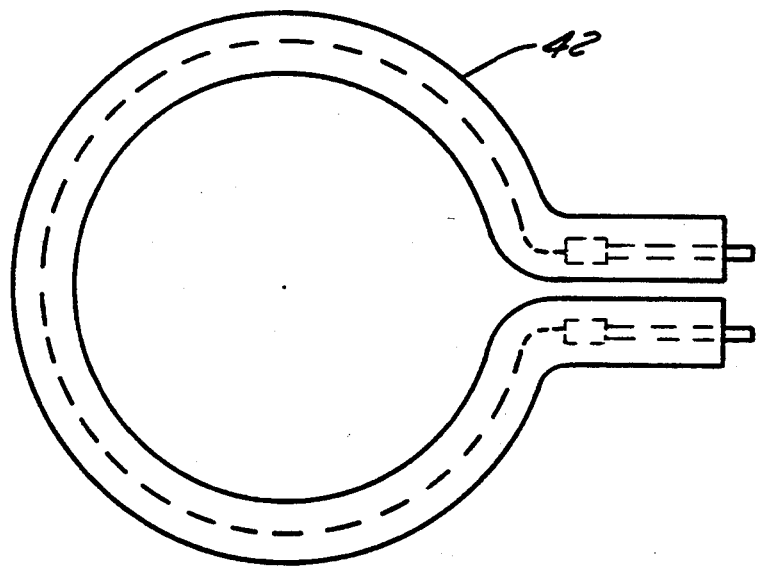
FIG. 6 is a top view of a toroidal flash tube.

To provide for coupling the light to an optical fiber, flash tube 42 has a toroidal shape, shown in FIGS. 5 and 6, and is disposed inside reflector 44. In addition to the toroidal shape other shapes, such as a continuous helix, may be used for flash tube 42. However, a helical tube is more difficult to manufacture than a toroidal tube. Referring now to FIG. 6, flash tube 42 is generally in the shape of a tours, but is not a perfect tours since the electrodes located at the end of the tours have to be connected to the power source. This does not create a significant disturbance in the circular shape of flash tube 42, since the connection to the electrodes can be made quite small.

Reflector 44 collects and concentrates the light, and has a cross-section of substantially an ellipse, in a plane perpendicular to the minor axis of the toroidal flash tube 42. The major axis of this ellipse preferably forms a small angle with the major axis of toroidal lamp 42. The exact value of the angle between the ellipse axis and the main axis of lamp 42 depends on the Numerical Aperture (NA) of the optical fiber. The toroidal flash tube is positioned so that its minor axis coincides with the focus of the ellipse. The other focus of the ellipse is at the edge of optical fiber 46. Reflector 44 may be machined from metal with the inner surfaces polished for good reflectivity. Aluminum is a very good reflector with high reflectivity in the visible and ultraviolet, and it may be used for this purpose. The reflector can be machined in one piece and then cut along a surface perpendicular to the main axis of the device. This will enable integration of the toroidal flash tube into the device.

Figure 4:
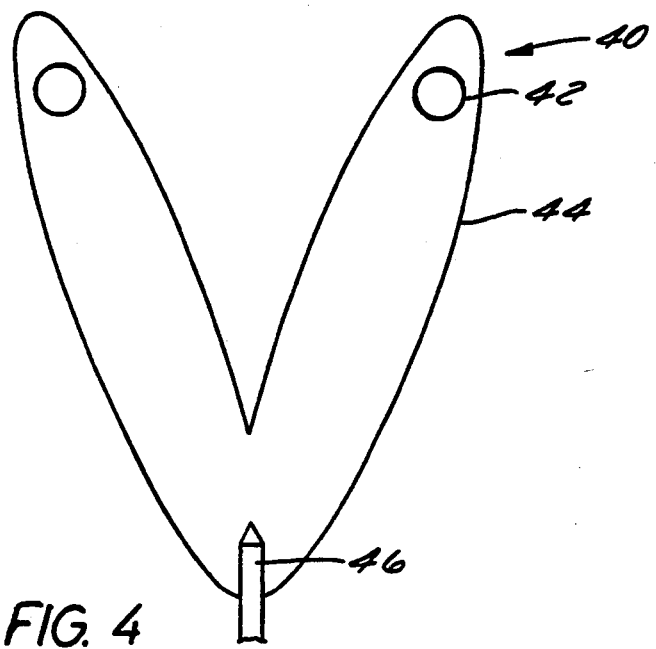
FIG. 4 is a cross-sectional view of a coupler for coupling light from a toroidal flash tube into an optical fiber with a conical edge.
Figure 7:
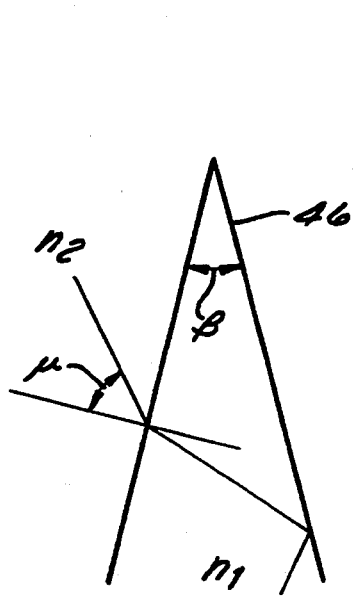
FIG. 7 shows the geometry for coupling into a conical section.

As shown in FIG. 4, the edge of optical fiber 46 is a cone with a small opening angle, so that the total area of the fiber exposed to the light from the flash tube is increased. Referring now to FIG. 7 the geometry for coupling light into a conical tip is shown. It is assumed here that the light comes from a region in space with a refractive index of $n_2$ and that the conical section of the fiber (as well as the rest of the fiber core) has a refractive index of $n_1$.

Not all the light rays hitting the cone are trapped in it. For light rays that propagate in a plane that contains the major axis of the system, a condition can be derived for the angle of a ray that will be trapped and absorbed in the fiber. This condition is shown in Equation 3.

$$\mathrm{Sin}\ (\mu_{criti}) = \mathrm{Cos}\ (\beta) - [n_1^2/n_2^2 - 1]^{\frac{1}{2}} \mathrm{sin}\ (\beta) \qquad (\mathrm{Eq.\ 3})$$

Light will be trapped in the conical portion of the optical fiber if the incidence angle $\mu$ is larger than $\mu_{criti}$ calculated from Equation 3. Trapping is possible only if $n_1 > n_2$. If the medium outside of the fiber is air, $n_2 = 1$. Not all of the light trapped in the conical section of the fiber will also be trapped in the straight portion of the fiber if a fiber with a core and a cladding is used. If a fiber with a core and no cladding is used (air cladding), then all the rays captured in the conical section of the fiber will also be trapped in the straight section of the fiber.

The configuration shown in FIG. 4 can also be used with a fluid filling the volume between the reflector and the optical fiber. A very convenient fluid for this purpose may be water. Water is also very effective in cooling the flashlamp if high repetition rate pulses are used. The presence of a fluid reduces the losses that are associated with glass to air transitions, such as the transition between the flashlamp envelope material and air. If a fluid is used in the reflector volume, then its refractive index can be chosen such that all the rays trapped in the conical section are also trapped in the fiber, even if core/cladding fibers are used.

Figure 8:
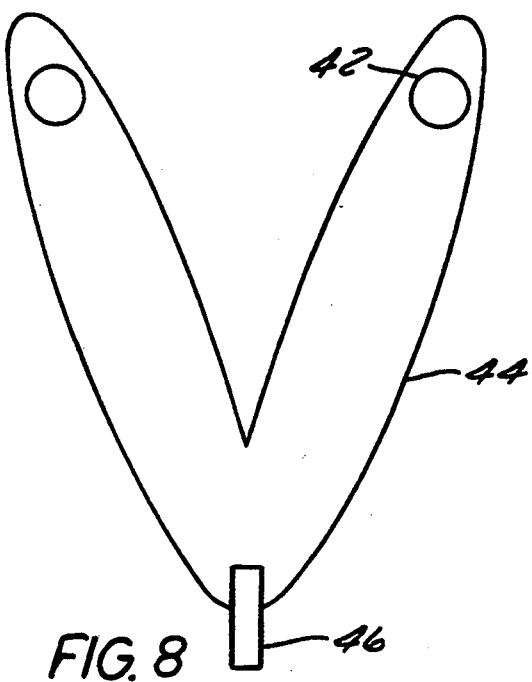
FIG. 8 is a cross-sectional view of a coupler for coupling light from a toroidal flash tube into an optical fiber with a flat edge.

Another way of configuring the fiber in the reflector is by using a fiber with a flat edge. This configuration is shown in FIG. 8 and has trapping efficiency very close to the trapping efficiency of the conical edge. Many other shapes of the fiber edge, such as spherical shapes, can also be used. The configuration of the fiber edge also has an effect on the distribution of the light on the exit side of the fiber and it can be chosen in accordance with the specific application of the device.

The device may be used with a variety of optical fibers. Single, or a small number of millimeter or sub-millimeter diameter fibers, will typically be used in invasive medical applications. In other applications, particularly in industrial and domestic applications, it may be preferable to use a fiber having a larger diameter, or a larger bundle of fibers, or a light guide.

Figure 9:
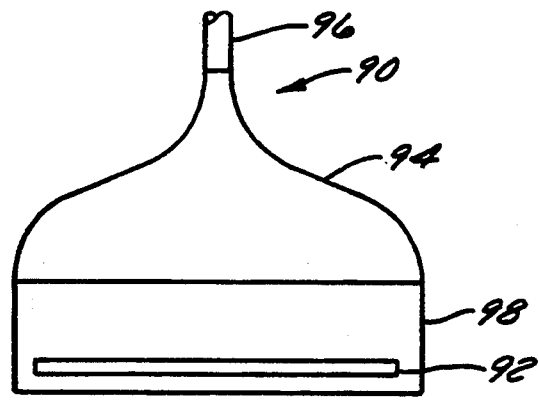
FIG. 9 is a front sectional view of a coupler for coupling light from a linear flash tube into a circular fiber bundle.
Figure 10:
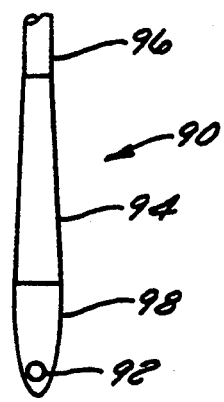
FIG. 10 is a side sectional view of the coupler of FIG. 9.

FIGS. 9 and 10 show a coupler 90 for coupling a linear flash tube 92 through a linear to circular fiber transfer unit 94 to a fiber bundle 96. A reflector 98 has an elliptical cross-section, shown in FIG. 10, in a plane parallel to the axis of linear flash tube 92 in this embodiment. Tube 92 is located on one focus of the ellipse while the linear side of linear to circular bundle converter 94 is located at the other focus of the ellipse. This configuration is relatively simple to manufacture and commercially available linear to circular converters such as 25-004-4 available from General Fiber Optics may be used. This configuration is particularly useful for larger exposure areas of the fiber, or for flash illumination purposes.

The energy and power densities that can be achieved by this invention are high enough to get the desired effects in surface treatment or medical applications. For the embodiment shown in FIG. 4 the total energy and power densities can be estimated as follows. For a typical toroidal lamp with a 4 mm bore diameter and a major diameter of 3.3 cm an electrical linear energy density input of 10 J/cm into the lamp can be used with a 5 $\mu$sec pulse width. The light output of the lamp will be 5 to 6 J/cm for optimal electrical operating conditions. For the reflector shown in FIG. 4, 50% of the light generated in the lamp will reach the lower focus. Thus, a total energy flux on the focus of 25 to 30 J may be obtained. For embodiments shown in FIG. 4 or FIG. 8 the total cross-section area of reflector at the focal plane has a cross-section of 0.8 cm$^2$. Energy densities on the order of 30 to 40 J/cm$^2$ at the entrance to the fiber should be attained with this cross-section. This corresponds to power densities of 5 to 10 MW/cm$^2$, which are the typical power densities used in medical or material processing applications.

For longer pulses, higher linear electrical energy densities into the lamp can be used. For a 1 msec pulse to the flash tube a linear electrical energy density of 100

J/cm can be used. The corresponding energy density at the focal area would be up to 300 J/cm². Such energy densities are very effective in industrial cleaning and processing applications as well as in medical applications.

Figure 11:
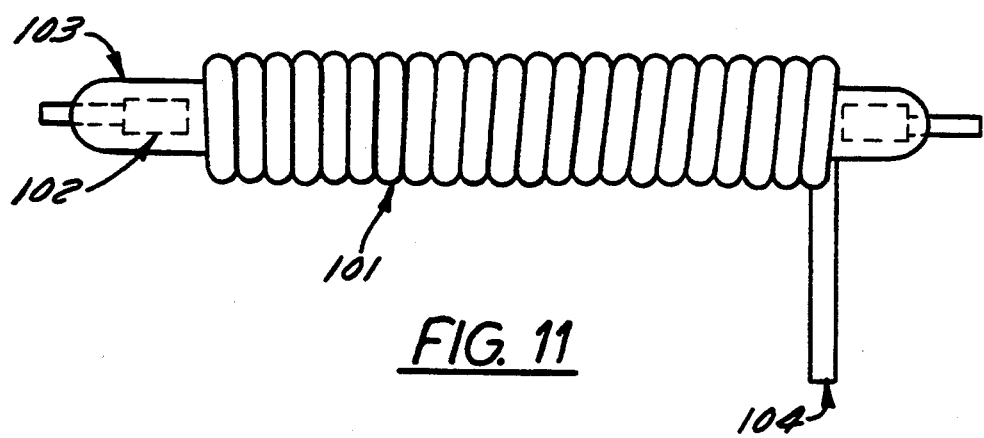
FIG. 11 is a front view of a coupler for coupling light from a linear flash tube into an optical fiber.
Figure 12:
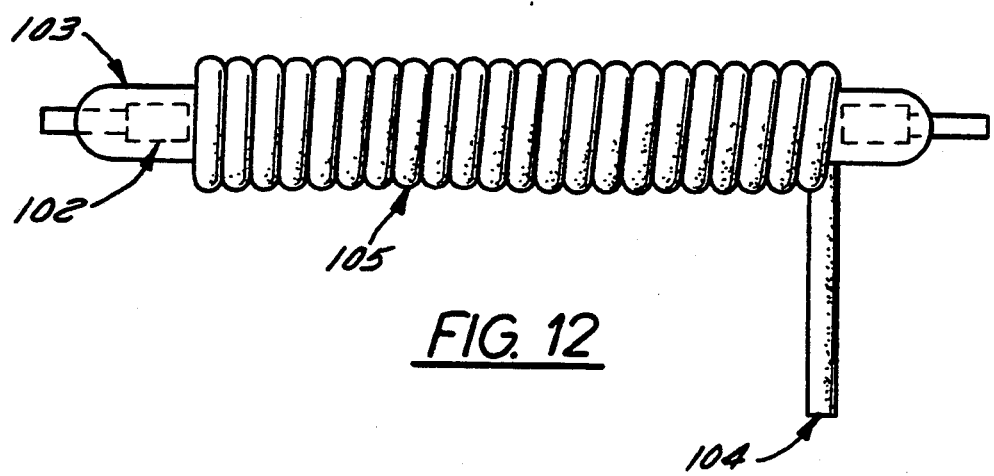
FIG. 12 is a front view of a coupler for coupling light from a linear flash tube into a doped optical fiber.

Alternative embodiments for coupling the optical fiber to an extended light source such as a linear flashlamp are shown in FIGS. 11 and 12. In the embodiment of FIG. 11 an optical fiber 101 is wound around a lamp 102 and a lamp envelope 103. Some of the light that is produced by the light source is coupled into the fiber. If the light rays are propagating in the direction that is trapped by the fiber then this light will propagate in the fiber and it can be used at a fiber output 104. One limitation of this configuration is the fact that most of the light emitted by lamp 103 travels in a direction perpendicular to the surface of lamp 103 and cannot be trapped in fiber 101.

The embodiment shown in FIG. 12 overcomes this problem. A doped optical fiber 105 is wound around lamp 102 and envelope 103, rather than an undoped fiber such as fiber 101 of FIG. 11. The dopant is a fluorescent material which is excited by the radiation emanating from lamp 102 and radiates light inside the fiber. This light is radiated omnidirectionally and the part of it that is within the critical angle of fiber 105 is trapped and propagates through the fiber and can be used at fiber output 104. The angle of light that is trapped in the fiber is the critical angle of the material from which the optical fiber or optical wave guide is made. For a fiber (or optical wave guide) in air this angle is given by $\sin \alpha = 1/n$.

Typically for glass or other transparent materials $n=1.5$ and $\alpha=41.8°$. This corresponds to a trapping efficiency of more than 10% of the light emitted by fluorescence inside the fiber. If we assume a 50% efficiency of the fluorescence process we find out that more than 5% of the light produced by the lamp is trapped and propagated down the fiber. For example, a 4" lamp with a linear electrical energy input of 300 J/inch and 50% electrical to light conversion efficiency would couple 2.5% of its electrical energy into the fiber. This corresponds, for the 4" lamp case to a total light energy of 30 J of light. This embodiment has the additional advantage of transferring the wavelength emitted by the lamp to a wavelength that may be more useful in some of the therapeutic or processing applications mentioned before. Thus, fluorescent material doped in the fiber can be chosen in accordance with an emission wavelength determined by the specific application of the device.

Thus, it should be apparent that there has been provided in accordance with the present invention a flashlamp and coupler that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

I claim:

1. A therapeutic treatment device comprising:
    an incoherent light source operable to provide a pulsed light output having a spectrum of frequencies continuous over at least one bandwidth for treatment;
    a housing with an opening, said light source being disposed in said housing, and said housing being suitable for being disposed adjacent a skin treatment area;
    a variable pulse-width pulse forming circuit electrically connected to said light source; and
    a reflector mounted within said housing and proximate said light source.

2. The treatment device of claim 1 further comprising at least one optical filter mounted proximate said opening.

3. The treatment device of claim 2 further comprising an iris mounted about said opening.

4. The treatment device of claim 3 including means for providing controlled energy density, filtered, pulsed light output through said opening and said iris to a skin area for treatment.

5. The device of claim 4 wherein said light source is a flashlamp.

6. The device of claim 5 wherein said light source comprises means for providing pulses having a width in the range of between substantially 0.5 and 10 microsec and an energy density of the light on the skin of more than 6 J/cm², whereby the power density is more than 600,000 W/cm².

7. The device of claim 5 wherein said light source comprises means for providing a pulse in the range of about 0.5 millisec to 100 millisec, whereby blood vessels proximate the skin may be coagulated.

8. The device of claim 5 wherein said light source further comprises a fluorescent material disposed about said flash lamp, said fluorescent material being of the type that absorbs radiation emitted by said flashlamp and emits radiation in a range effective for skin thermolysis and coagulation of blood vessels in the skin and immediately thereunder, wherein said optical filters are of the type that absorb radiation in the wavelength range of substantially less than 500 nm.

9. The device of claim 5, wherein said light source comprises means for providing pulses having a width in the range of between substantially 0.5 microsec and 10 microsec and an energy density of the light on the skin of more than 10 J/cm².

10. The device of claim 5, wherein said light source comprises means for providing pulses having a width in the range of between substantially 0.5 millisec and 10 millisec and an energy density of the light on the skin of more than 6 J/cm².

11. The device of claim 5, wherein said light source comprises means for providing pulses having a width in the range of between substantially 0.5 millisec and 10 millisec and an energy density of the light on the skin of more than 10 J/cm².

12. The device of claim 1 wherein said reflector has a reflectivity which varies as a function of wavelength.

13. A method of treatment with light energy comprising the steps of:
    providing a pulsed light output having a spectrum of frequencies continuous over at least one bandwidth from a non-laser, incoherent light source;
    directing said pulsed light output to blood vessels in the vicinity of the skin;
    focusing said light source for controlling the power density of said pulsed light output; and
    filtering and controlling the spectrum of said light output;
    wherein said step of controlling the pulse-width includes the step of providing a pulse-width in the range of about 0.5–10 microsec with energy density of the light on the skin on the order of at least 6 J/cm², whereby the skin is treated with a power density of at least 600,000 W/cm².

14. A method of treatment with light energy comprising the steps of:
providing a pulsed light output having a spectrum of frequencies continuous over at least one bandwidth from a non-laser, incoherent light source;
directing said pulsed light output to skin irregularities;
focusing said light source for controlling the power density of said pulsed light output; and
filtering and controlling the spectrum of said pulsed light output;
wherein said step of controlling the pulse-width includes the step of providing a pulse-width in the range of substantially 0.5 millisec to 100 millisec, whereby blood vessels are coagulated.

15. A method of treatment with light energy comprising the steps of:
providing a pulsed light output from a non-laser, incoherent light source;
directing said pulsed light output to a treatment area;
controlling the pulse-width of said pulsed light output;
focusing said light source for controlling the power density of said pulsed light output;
filtering and controlling the spectrum of said pulsed light output;
providing a fluorescent material surrounding the light source;
absorbing radiation in the fluorescent material, said radiation being emitted by said light source;
emitting radiation from the fluorescent material, the radiation having a wavelength in the range of substantially 550 to 650 nm; and
absorbing radiation in the wavelength range substantially less than 500 nm.

16. A method of treatment with light energy comprising the steps of:
providing a pulsed light output having a spectrum of frequencies continuous over at least one bandwidth from a non-laser, incoherent light source;
directing said pulsed light output to blood vessels in the vicinity of the skin;
focusing said light source for controlling the power density of said pulsed light output; and
filtering and controlling the spectrum of said light output;
wherein said step of controlling the pulse-width includes the step of providing a pulse-width in the range of about 0.5 microsec to 10 microsec with energy density of the light on the skin on the order of at least 10 J/cm².

17. A method of treatment with light energy comprising the steps of:
providing a pulsed light output having a spectrum of frequencies continuous over at least one bandwidth from a non-laser, incoherent light source;
directing said pulsed light output to blood vessels in the vicinity of the skin;
focusing said light source for controlling the power density of said pulsed light output; and
filtering and controlling the spectrum of said light output;
wherein said step of controlling the pulse-width includes the step of providing a pulse-width in the range of about 0.5 millisec to 10 millisec with energy density of the light on the skin on the order of at least 6 J/cm2, whereby the skin is treated with a power density of at least 600,000 W/cm².

18. A method of treatment with light energy comprising the steps of:
providing a pulsed light output having a spectrum of frequencies continuous over at least one bandwidth from a non-laser, incoherent light source;
directing said pulsed light output to blood vessels in the vicinity of the skin;
focusing said light source for controlling the power density of said pulsed light output; and
filtering and controlling the spectrum of said light output;
wherein said step of controlling the pulse-width includes the step of providing a pulse-width in the range of about 0.5 millisec to 10 millisec with energy density of the light on the skin on the order of at least 10 J/cm², whereby the skin is treated with a power density of at least 600,000 W/cm².

* * * * *

(12) EX PARTE REEXAMINATION CERTIFICATE (6712th)
United States Patent
Eckhouse

(10) Number: US 5,405,368 C1
(45) Certificate Issued: Mar. 24, 2009

(54) METHOD AND APPARATUS FOR THERAPEUTIC ELECTROMAGNETIC TREATMENT

(75) Inventor: Shimon Eckhouse, Haifa (IL)

(73) Assignee: Lumenis, Ltd., Yokneam (IL)

Reexamination Request:
No. 90/010,068, Dec. 5, 2007
No. 90/010,136, Apr. 7, 2008

Reexamination Certificate for:
Patent No.: 5,405,368
Issued: Apr. 11, 1995
Appl. No.: 07/964,210
Filed: Oct. 20, 1992

(51) Int. Cl.
*A61N 5/06* (2006.01)

(52) U.S. Cl. .............................. 607/88; 607/90; 607/94; 606/3; 606/9

(58) Field of Classification Search ................... None
See application file for complete search history.

(56) References Cited

U.S. PATENT DOCUMENTS

| | | | |
|---|---|---|---|
| 2,716,698 A | 8/1955 | Brukner ........................... 240/1 |
| 2,954,771 A | 10/1960 | Boyan ......................... 128/396 |
| 3,327,712 A | 6/1967 | Kaufman et al. ............ 128/398 |
| 3,693,623 A | 9/1972 | Harte et al. ............... 128/303.1 |
| 3,834,391 A | 9/1974 | Block ....................... 128/303.1 |
| 3,930,504 A | 1/1976 | de Laforcade ........... 128/303.1 |
| 4,229,658 A | 10/1980 | Gonser .................... 250/504 H |
| 4,233,493 A | 11/1980 | Nath ........................... 219/354 |
| 4,283,661 A | 8/1981 | Doty ........................... 315/360 |
| 4,298,005 A | 11/1981 | Mutzhas ..................... 128/396 |
| 4,321,930 A | 3/1982 | Jobsis et al. ................. 128/633 |
| 4,366,570 A | 12/1982 | Bees ............................. 372/70 |
| 4,380,240 A | 4/1983 | Jobsis et al. ................ 128/633 |
| 4,388,924 A | 6/1983 | Weissman et al. ......... 128/303.1 |
| 4,444,190 A | 4/1984 | Mutzhas ..................... 128/396 |
| 4,497,018 A | 1/1985 | Rice ............................. 363/96 |
| 4,506,196 A | 3/1985 | Bees ....................... 315/241 R |
| 4,539,987 A | 9/1985 | Nath et al. ................ 128/303.1 |
| 4,560,883 A | 12/1985 | Kerschgens .................. 250/504 |
| 4,564,011 A | 1/1986 | Goldman .................. 128/303.1 |
| 4,645,980 A | 2/1987 | Yang ........................... 315/159 |
| 4,647,830 A | 3/1987 | Bees ............................. 320/1 |
| 4,653,495 A | 3/1987 | Nanaumi .................. 128/303.1 |
| 4,672,969 A | 6/1987 | Dew ........................... 128/397 |
| 4,726,377 A | 2/1988 | Jegers et al. ................ 128/376 |
| 4,729,375 A | 3/1988 | Jegers et al. ................ 128/376 |
| 4,733,660 A | 3/1988 | Itzkan ..................... 128/303.1 |
| 4,775,361 A | 10/1988 | Jacques et al. ............... 604/20 |
| 4,810,658 A | 3/1989 | Shanks et al. ............... 436/172 |
| 4,829,262 A | 5/1989 | Furumoto ................... 330/4.3 |

(Continued)

FOREIGN PATENT DOCUMENTS

| | | |
|---|---|---|
| DE | 27 17 421 A1 | 11/1978 |
| JP | 4-90360 | 8/1992 |
| SE | 465 953 B | 11/1991 |
| WO | WO 89/00871 | 2/1989 |
| WO | WO 90/14836 | 12/1990 |
| WO | WO-91/15264 | 10/1991 |
| WO | WO 91/15264 | 10/1991 |
| WO | WO 98/52645 | 11/1998 |

OTHER PUBLICATIONS

Achauer et al., "Argon Laser Treatment of Telangiectasia of the Face and Neck: 5 Years' Experience", *Lasers Surg. Med.*, 7:495–498 (1987).

(Continued)

*Primary Examiner*—Beverly M. Flanagan

(57) ABSTRACT

A therapeutic treatment device includes a housing and an incoherent light source such as a flashlamp disposed in the housing. The flashlamp provides a pulsed light output for treatment of external skin disorders. To provide light to the treatment area the housing has an opening that is disposed adjacent a skin treatment area. A reflector is mounted within the housing near proximate the light source to reflect the light to the treatment area. At least one optical filter and an iris are mounted near the opening in the housing. Power to the lamp is provided by a pulse forming circuit that can provide a variable pulse width.

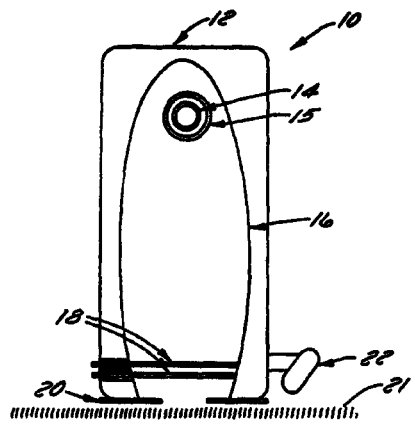

U.S. PATENT DOCUMENTS

| | | | |
|---|---|---|---|
| 4,835,749 A | 5/1989 | Welton | 368/10 |
| 4,839,562 A | 6/1989 | Francis et al. | 315/149 |
| 4,851,738 A | 7/1989 | Yang | 315/159 |
| 4,871,559 A | 10/1989 | Dunn et al. | 426/248 |
| 4,884,568 A | 12/1989 | Hahn | 128/303.1 |
| 4,930,504 A | 6/1990 | Diamantopoulos et al. | 128/395 |
| 4,938,221 A | 7/1990 | Tuffel | 128/401 |
| 4,947,859 A | 8/1990 | Brewer et al. | 128/715 |
| 5,008,579 A | 4/1991 | Conley et al. | 310/303 |
| 5,020,995 A | 6/1991 | Levy | 433/215 |
| 5,034,235 A | 7/1991 | Dunn et al. | 426/238 |
| 5,039,867 A | 8/1991 | Nishihara et al. | 250/492.3 |
| 5,054,488 A | 10/1991 | Muz | 128/633 |
| 5,059,192 A | 10/1991 | Zaias | 606/9 |
| 5,066,293 A | 11/1991 | Furumoto | 606/9 |
| 5,071,422 A | 12/1991 | Watson et al. | 606/128 |
| 5,083,093 A | 1/1992 | Adler et al. | 328/65 |
| 5,113,462 A | 5/1992 | Clancy et al. | 385/53 |
| 5,125,922 A | 6/1992 | Dwyer et al. | 606/3 |
| 5,126,621 A | 6/1992 | Morton et al. | 313/237 |
| 5,194,723 A | 3/1993 | Cates et al. | 250/205 |
| 5,204,517 A | 4/1993 | Cates et al. | 250/205 |
| 5,226,107 A | 7/1993 | Stern et al. | 392/416 |
| 5,269,778 A | 12/1993 | Rink et al. | 606/12 |
| 5,281,798 A | 1/1994 | Hamm et al. | 250/205 |
| 5,282,797 A | 2/1994 | Chess | 606/9 |
| 5,290,273 A | 3/1994 | Tan | 606/9 |
| 5,290,274 A | 3/1994 | Levy et al. | 606/13 |
| 5,312,395 A | 5/1994 | Tan et al. | 606/9 |
| 5,320,618 A | 6/1994 | Gustafsson | 606/9 |
| 5,328,488 A | 7/1994 | Daikuzono | 606/16 |
| 5,328,517 A | 7/1994 | Cates et al. | 134/7 |
| 5,334,190 A | 8/1994 | Seiler | 606/5 |
| 5,337,741 A | 8/1994 | Diamond | 600/8 |
| 5,344,418 A | 9/1994 | Ghaffari | 606/9 |
| 5,344,433 A | 9/1994 | Talmore | 607/88 |
| 5,374,265 A | 12/1994 | Sand | 606/5 |
| 5,400,791 A | 3/1995 | Schlier et al. | 128/664 |
| 5,423,803 A | 6/1995 | Tankovich et al. | 606/9 |
| 5,445,146 A | 8/1995 | Bellinger | 607/89 |
| D363,349 S | 10/1995 | Dittert | D24/158 |
| 5,474,528 A | 12/1995 | Meserol | 604/20 |
| 5,489,279 A | 2/1996 | Meserol | 604/290 |
| 5,522,814 A | 6/1996 | Bernaz | 606/36 |
| 5,546,214 A | 8/1996 | Black et al. | 359/203 |
| 5,558,666 A | 9/1996 | Dewey et al. | 606/9 |
| 5,595,568 A | 1/1997 | Anderson et al. | 606/9 |
| 5,618,284 A | 4/1997 | Sand | 606/5 |
| 5,725,565 A | 3/1998 | Smith | 607/88 |
| 5,755,753 A | 5/1998 | Knowlton | 607/98 |
| 5,814,040 A | 9/1998 | Nelson et al. | 606/9 |
| 5,817,089 A | 10/1998 | Tankovich et al. | 606/9 |
| 5,817,090 A | 10/1998 | Abergel et al. | 606/9 |
| 5,843,143 A | 12/1998 | Whitehurst | 607/88 |
| RE36,634 E | 3/2000 | Ghaffari | 606/9 |
| 6,171,332 B1 | 1/2001 | Whitehurst | 607/89 |

OTHER PUBLICATIONS

Alora et al., "Recent Developments in Cutaneous Lasers", *Lasers Surg. Med.*, 26:108–118 (2000).

Alster et al., "Treatment of Port–Wine Stains with the Flashlamp–pumped Pulsed Dye Laser: Extended Clinical Experience in Children and Adults", *Ann. Plast. Surg.*, 32(5):478–484 (1994).

Altshuler et al., "Extended Theory of Selective Photothermolysis", *Lasers Surg. Med.*, 29:416–432 (2001).

Ambrose et al., "Prospective randomized comparison of photocoagulation and rubber band ligation in treatment of haemorrhoids", *Br. Med. J.*, 286:1389–1391 (1983).

Anderson et al., "Mechanisms of Selective Vascular Changes Caused by Dye Lasers",*Lasers Surg. Med.*, 3:211–215 (1983).

Anderson et al., "Microvasculature Can Be Sensitively Damaged Using Dye Lasers: A Basic Theory and Experimental Evidence in Human Skin", *Lasers Surg. Med.*, 1:263–276 (1981).

Anderson et al., "Selective Photothermolysis: Precise Microsurgery by Selective Absorption of Pulsed Radiation", *Science*, 220:524–527 (1983).

Anderson, T.F., "Light Sources in Photomedicine", in *Clinical Photomedicine*, Chapter 3, pp. 37–58, Marcel Dekker, Inc., New York (1993).

Angermeier, M.C., "Treatment of facial vascular lesions with intense pulsed light",*J. Cutan. Laser Ther.*, 1:95–100 (1999).

Anvari et al., "Selective cooling of biological tissues: application for thermally mediated therapeutic procedures", *Phys. Med. Biol.*, 40:241–252 (1995).

Apfelberg et al., "Comparison of Argon and Carbon Dioxide Laser for Treatment of Decorative Tattoos Clinical and Pathological Observations", *Lasers Surg. Med.*, 3:183 (Abstract No. 294) (1983).

Apfelberg et al., Dot or Pointillistic Method for Improvement in Results of Hypertrophic Scarring in the Argon Laser Treatment of Portwine Hemangionamas,*Lasers Surg. Med.*, 6:552–558 (1987).

Apfelberg et al., "Investigation of YAG Laser Uses in Plastic Surgery", *Lasers Surg.*, 6:246 (Abstract No. 77) (1986).

Apfelberg et al., "Preliminary Investigation of KTP/532 Laser Light in the Treatment of Hemangiomas and Tattoos", *Lasers Surg. Med.*, 6:38–42 (1986).

Apfelberg et al., "Progress Report on Extended Clinical Use of the Argon Laser for Cutaneous Lesions", *Lasers Surg. Med.*, 1:71–83 (1980).

Apfelberg et al., "Progress Report on Multicenter Study of Laser–Assisted Liposuction", *Aesth. Plast. Surg.*, 18:259–264 (1994).

Apfelberg et al., "Results of Argon and CO2 Laser Exposure of Telangiectasia of the Lower Extremity: A Preliminary Report", *Lasers Surg. Med.*, 3:149 (Abstract No. 165) (1983).

Apfelberg et al., "Study of Three Laser Systems for Treatment of Superficial Varicosities of the Lower Extremity", *Lasers Surg. Med.*, 7:219–223 (1987).

Apfelberg et al., "Superpulse $CO_2$ Laser Treatment of Facial Syringomata", *Lasers Surg. Med.*, 7:533–537 (1987).

Apfelberg et al., "Update on Laser Usage in Treatment of Decorative Tattoos", *Lasers Surg. Med.*, 2:169–177 (1982).

Apfelberg, D.B., "Intralesional Laser Photocoagulation—Steroids as an Adjunct to Surgery for Massive Hemangiomas and Vascular Malformations", *Ann. Plast. Surg.*, 35:144–148 (1995).

Ara et al., "Irradiation of Pigmented Melanoma Cells with High Intensity Pulsed Radiation Generates Acoustic Waves and Kills Cells", *Lasers Surg. Med.*, 10:52–59 (1990).

Ashinoff et al., "Cappillary Hemangiomas and Treatment with the FlashLamp–Pumped Pulsed Dye Laser", *Arch. Dematol.*, 127:202–205 (1991).

Ashinoff et al., "Flashlamp–pumped pulsed dye laser for port–wine stains in infancy: Earlier versus later treatment", *J. Am. Acad. Dermatol.*, 24:467–472 (1991).

Bell et al., "100 μsec pulsed $CO_2$ laser resurfacing of lower eyelids: Erythema and rhytides reduction", *SPIE*, 2970:360–366 (1997).

Broska et al., "Comparison of the Argon Tunable Dye Laser with the Flashlamp Pulsed Dye Laser in Treatment of Facial Telangiectasia", *J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–594 (1991).

Burson et al., "Gel de Transmision de Ultrasonidos: Estudio Comparitivo de Distintas Formulaciones", *Farm Hosp.*, pp. 394–399 (1991) (in Spanish, with English Abstract Only).

Cates, M.C., "A long pulse (5 μs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremities", *J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL", *J. Cutan. Laser Ther.*, 1:101–104 (1999).

Cole–Beuglet et al., "Ulstrasound mammography for the Augmented Breast", *Radiology*, 146:737–742 (1983).

Colver et al., "Port Wine Stains", *J. Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "A History of Photodynamic Therapy", *Aust. N. Z. J. Surg.*, 61:340–348 (1991).

Denham et al., "Light Distribution in Laser Irradiated Tissue", *Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulos et al., "High–energy Short–pulse Flashlamps: Operating Characteristics", *Applied Optics*, 16:70–75 (1977).

Ell et al., "Laser Lithotripsy of Gallstone by Means of a Pulsed Neodymium YAG Laser—In Vitro and Animal Experiments", *Endoscopy*, 18:92–94 (1986).

Englehardt et al., "Spectroscopy During Laser Induced Shock Wave Lithotripsy", *SPIE*, 906:200–204 (1988).

Fitzpatrick et al., "Flashlamp–pumped Pulsed Dye Laser Treatment of Port–Wine Stains", *J. Dermatol. Surg. Oncol.*, 20:743–748 (1994).

Fitzpatrick et al., "Treatment of Leg Veins: A Comparison of Laser Therapy with a Noncoherent, Multiwave Light Source", *Proc. Ann. Meeting IEEE Lasers & Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study", *Lasers Med. Sci.*, 8:185–196 (1993).

Foster et al., "The Successful Use of the PhotoDerm VL in the Treatment of a Cavernous Hemangioma in a Dark–Skinned Infant", *Minimally Invasive Surgical Nursing*, 10:102–104 (1996).

Garden et al., "Effects of Dye Laser Pulse Duration on Selective Cutaneous Vascular Injury", *J. Invest. Dermatol.*, 87(5):653–657 (1986).

Garden et al., "The Treatment of Port–wine Stains by the Pulsed Dye Laser: Analysis of Pulse Duration and Long–term Therapy", *Arch. Dermatol.*, 124:889–896 (1988).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Lasers Surg. Med.*, 11:287–296 (1991).

Gijsbers et al., "Effect of Force on Ablation Depth for a XeCl Excimer Laser Beam Delivered by an Optical Fiber in Contact with Arterial Tissue Under Saline", *Lasers Surg. Med.*, 12:576–584 (1992).

Gilbert, D.J., "Incorporating Photodynamic Therapy Into a Medical and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long–Term Hair Removal", *J. Cutan. Laser Ther.*, 1:167–171 (1999).

Gold et al., "Treatment of Wrinkles and Skin Tightening Using Aluma™ Skin Renewal System with FACES™ (Functional Aspiration Controlled Electrothermal Stimulation) Technology", *Aesthetic Buyers Guide*, pp. 1–6 (2005).

Gold, M.H., "Aminolevulinic Acid Photodynamic Therapy: Medical Evidence for Its Expanded Use", *Expert Rev. Med. Devices*, 3:357–371 (2006).

Gold, M.H., "Introduction to Photodynamic Therapy: Early Experience", *Dermatol. Clin.*, 25:1–4 (2007).

Goldberg et al., "Nonablative Treatment of Rhytids With Intense Pulsed Light", *Lasers Surg. Med.*, 26:196–200 (2000).

Goldberg et al, "Q–switched Nd:YAG Laser: Rhytid Improvement by Non–Ablative Dermal Remodeling", *J. Cutan. Laser Ther.*, 2:157–160 (2000).

Goldberg, D.J., "Effect of Temperature–Controlled Cooling on Light–Based Skin Treatments", *J. Cos. Laser Ther.*, 8:155–156 (2006).

Goldberg, D.J., "Erbium: YAG Laser Resurfacing: What Is Its Role?", *Aesth. Surg. J.*, 18(4):255–260 (1998).

Goldberg, D.J., "New Collagen Formation After Dermal Remodeling with an Intense Pulsed Light Source", *J. Cutan. Laser Ther.*, 2:59–61 (2000).

Goldman et al., "600 nm Flash Pumped Dye Laser for Fragile Telangiectasia of the Elderly", *Lasers Surg. Med.*, 13:227–233 (1993).

Goldman et al., "Photothermal Sclerosis of Leg Veins", *Dermatol. Surg.*, 22:323–330 (1996).

Goldman et al., "Pulsed dye laser treatment of telangiectases with and without subtherapeutic sclerotherapy", *J. Am. Acad. Dermatol.*, 23(1):23–30 (1990).

Goldman et al., "Treatment of Cutaneous Vascular Lesions", in *Cutaneous Laser Surgery*, Chapter 2, pp. 19–105 (1994).

Goldman et al., "Treatment of port–wine stains (capillary malformation) with the flashlamp–pumped pulsed dye laser", *J. Pediatrics*, 122(1):71–77 (1993).

Goldman, M.P., "Laser and Noncoherent Pulsed Light Treatment of Leg Telangiectasia and Venules", *Cos. Dermatol.*, 8(10):43–44 (1995).

Goldman, M.P., "Sclerotherapy Treatment for Varicose and Telangiectatic Leg Veins", in *Vascular and Pigmented Abnormalities*, Chapter 17, pp. 256–271 (1997).

Gomer, H., "Military laser burns away skin flaws", *The London Sunday Times*, No. 8929 (Oct. 15, 1995).

Gonzalez et al., "Treatment of telangiectases and other benign vascular lesions with the 577 nm pulsed dye laser", *J. Am. Acad. Dermatol.*, 27(2):220–226 (1992).

Gregory et al., "Effect of Blood Upon the Selective Ablation of Atherosclerotic Plaque with a Pulsed Dye Laser", *Lasers Surg. Med.*, 10:533–543 (1990).

Grevelink et al., "Update on the Treatment of Benign Pigmented Lesions with the Q–Switched Ruby Laser", *Lasers Surg. Med.*, 4:73–74 (Abstract No. 326) (1992).

Groot et al., "Comparison of the infrared coagulator and the carbon dioxide laser in the removal of decorative tattoos", *J. Am. Acad. Dermatol.*, 15:518–522 (1986).

Gustafsson et al., "A Variable Pulsewidth Vascular System for Dermatology",*SPIE*, 2128:188–196 (1994).

Guttman, C., "Novel radiofrequency–based treatment achieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE*, 2671:211–218 (1996).

Henderson, B.W., "Photodynamic therapy—coming of age", *Photodermatology*, 6:200–211 (1989).

Henning et al., "Clinical and Histological Evaluation of Portwine Stain Treatment with a Microsecond pulsed Dye–laser at 577 NM", *Lasers Surg. Med.*, 4:375–380 (1984).

Henning et al., "Port Wine Stain Coagulation Experiments with a 540–nm Continuous Wave Dye–laser", *Lasers Surg. Med.*, 2:205–210 (1983).

Henning et al., "Rhinophyma Treated by Argon Laser",*Lasers Surg. Med.*, 2:211–215 (1983).

Henning et al., "Treatment of Keloids and Hypertrofic Scars with an Argon Laser",*Lasers Surg. Med.*, 6:72–75 (1986).

Hilsenrath, J.E., "Investing it; Unsightly Veins? Zap. Wall St. Woes? Zap.",*New York Times*, http://www.nytimes.com, pp. 1–3 (Jun. 23, 1996).

Hruza et al., "Laser Skin Resurfacing", *Arch. Dermatol.*, 132:451–455 (1996).

Hughes, P.S.H., "Multiple Miliary Osteomas of the Face Ablated With the Erbium: YAG Laser",*Arch. Dermatol.*, 135:378–380 (1999).

"Infrared–Coagulator", Lumatec product leaflet, pp. 1–4.

Ishimaru, A., "Diffusion of light in turbid material",*Applied Optics*, 28(12):2210–2215 (1989).

Jacques, S.L., "The Role of Skin Optics in Diagnostic and Therapeutic Uses of Lasers", *Lasers Dermatol.*, pp. 1–21 (1992).

Jaitly et al., "1 MV Long Pulse Generator with Low Ripple and Low Droop", $8^{th}$ *IEEE Int'l Pulsed Power Conf.*, pp. 161–165 (1991).

Jaitly et al., "Design and Testing of Multi–output 300kV Prototype Induction Cell Pulsed Power Supply for Darht", $10^{th}$ *IEEE Int'l Pulsed Power Conf.*, pp. 1412–1421 (1995).

Jay, H.H., "Victory Over Veins", http://www.nytimes.com, pp. 1–2 (Jul. 21, 1996).

Johannigmann et al., "Ein Neues Ultraschall–Kontaktgel", *Geburtsh. U. Frauenheilk*, p. 34 (1974) (in German, with English Abstract Only).

Kalka et al., "Photodynamic Therapy in Dermatology",*J. Am. Acad. Dermatol.*, 42:389–413 (2000).

Kaminester, L.H., "Suntanning Centers", *JAMA*, 244(11):1258–1259 (1980).

Kaufmann et al., "Pulsed 2·94–μm erbium–YAG laser skin ablation—experimental results and first clinical application", *Clin. Exp. Dermatol.*, 15:389–393 (1990).

Keijzer et al., "Laser Beam Diameter for Port Wine Stain Treatment", *Lasers Surg. Med.*, 11:601–605 (1991).

Kennedy et al., "Photodynamic Therapy with Endogenous Protoporphyrin, IX: Basic Principles and Present Clinical Experience", *J. of Photochem. Photobio.*, 6:143–148 (1990).

Kilmer et al., "Pulse Dye Laser Treatment of Rhytids", *Lasers Surg. Med.*, p. 44 (Abstract No. 194) (1997).

Koechner, W., in *Solid State Laser Engineering*, Springer Series in Optical Sciences—vol. 1, Chapters 1–2, pp. 1–620, Springer–Verlag, New York (1976).

Lakmaker et al., "Modeling the Color Perception of Port Wine Stains and its Relation to the Depth of Laser Coagulated Blood vessels", *Lasers Surg. Med.*, 13:219–226 (1993).

Lash et al., "How We Got Here", *Lasers Surg. Med.*, 3:113 (Abstract No. 29) (1983).

Lask et al., "Laser Skin Resurfacing with the SikTouch Flashscanner for Facial Rhytides", *Dermatol. Surg.*, 21:1021–1024 (1995).

Lask et al., "Nonablative laser treatment of facial rhytides", *SPIE*, 2970:338–349 (1997).

Levins et al., "Q–Switched Ruby Laser Treatment of Tattoos", *Lasers Surg. Med.*, Suppl. 3:63–64 (Abstract No. 255) (1991).

Lowe et al., "Skin Resurfacing with the Ultrapulse Carbon Dioxide Laser", *Dermatol. Surg.*, 21:1025–1029 (1995).

Magee et al., "Vein Marking Through Ultrasound Coupling Gel", *Eur. J. Vasc. Surg.*, 4:491–492 (1990).

Majaron et al., "Deep Coagulation of Dermal Collagen with Repetitive Er:YAG Laser Irradiation", *Lasers Surg. Med.*, 26:215–222 (2000).

Majaron et al., "Er:YAG Laser Skin Resurfacing Using Repetitive Long–Pulse Exposure and Cryogen Spray Cooling: I. Histological Study", *Lasers Surg. Med.*, 28:121–130 (2001).

Majaron et al., "Er:YAG Laser Skin Resurfacing Using Repetitive Long–Pulse Exposure and Cryogen Spray Cooling: II. Theoretical Analysis", *Lasers Surg. Med.*, 28:131–137 (2001).

Margolis et al., "Visible Action Spectrum for Melanin–Specific Selective Photothermolysis", *Lasers Surg. Med.*, 9:389–397 (1989).

Marhic et al., "White–Light Flashlamp–pumped dye laser for photography through endoscopes", *Optics Communications*, 45(1):21–25 (1983).

McCaughan et al., "Photodynamic Therapy for Cutaneous and Subcutaneous Malignant Neoplasms", *Arch. Surg.*, 124:211–216 (1989).

McCaughan et al., "Photodynamic Therapy: An Eight–Year Experience", in *Photodynamic Therapy: Basic Principles and Clinical Applications*, pp. 323–331 (1992).

Meijering et al., "Limits of Radial Time Constants to Approximate Thermal Response of Tissue", *Lasers Surg. Med.*, 13:685–687 (1993).

Miller et al., "Optical Modelling of Light Distributions in Skin Tissue Following Laser Irradiation", *Lasers Surg. Med.*, 13:565–571 (1993).

Milner et al., "Analysis of nonablative skin resurfacing", *SPIE*, 2970:367–373 (1997).

Mordon et al., "Rationale for Automatic Scanners in Laser Treatment of Port wine Stains", *Lasers Surg. Med.*, 13:113–123 (1993).

Morelli et al., "Tunable Dye Laser (577 nm) Treatment of Port Wine Stains", *Lasers Surg. Med.*, 6:94–99 (1986).

Motamedi et al., "Thermal Response of Tissue During Laser Angioplasty", *Lasers Surg. Med.*, 5:172 (Abstract No. 114) (1985).

Mutzhas et al., "A New Apparatus with High Radiation Energy Between 320–460 nm: Physical Description and Dermatological Applications", *J. Invest. Dermatol.*, 76:42–47 (1981).

Nakagawa et al., "Ultrastructural Changes in Human Skin After Exposure to a Pulsed Laser",*J. Invest. Dermatol.*, 84(5):396–400 (1985).

Nestor et al., "New Perspectives on Photorejuvenation", *Skin & Aging*, 11:68–74 (2003).

Newman et al., "Variable Pulse Erbium: YAG Laser Skin Resurfacing of Perioral Rhytides and Side–by–side Comparison with Carbon Dioxide Laser", *Lasers Surg. Med.*, 26:208–214 (2000).

Parrish et al., "Exploring Mechanisms of Specificity in Laser–Tissue Interactions", *Lasers Surg. Med.*, 3:175 (Abstract No. 260) (1983).

Parrish et al., "Spatial Confinement of Thermal Effects of Pulsed Laser Irradiation of Tissue",*Lasers Surg. Med.*, 3:157 (Abstract No. 195) (1973).

Paul et al., "The Effect of Temperature and Other Factors on Selective Microvascular Damage Caused by Pulsed Dye Laser", *J. Invest. Dermatol.*, 81(4):333–336 (1983).

Pfefer et al., "Mechanisms of Laser–Induced Thermal Coagulation of Whole Blood in vitro", *SPIE*, 3590:20–31 (1999).

Philipp et al., "Treatment of Congenital Vascular Disorders: Classification, Step Programme and Therapeutical Procedures", *SPIE*, 2086:228–238 (1993).

Pickering et al., "58 nm for the Laser Treatment of Port Wine Stains: A Possible Mechanism", *Lasers Surg. Med.*, 11:616–618 (1991).

Plewig et al., "A new apparatus for the delivery of high intensity UVA and UVA + UVB irradiation, and some dermatological applications", *Br. J. Dermatol.*, 98:15–24 (1978).

Polla et al., "Tunable Pulsed Dye Laser for the Treatment of Benign Cutaneous Vascular Ectasia", *Dermatologica*, 174:11–17 (1987).

Pottier et al., "Assessment of Non–Coherent Light Sources for Photodynamic Therapy",*SPIE*, 2371:364–368 (1995).

Pratesi, R., "Potential Use of Incoherent and Coherent Light–Emitting–Diodes (LEDs) in Photomedicine", in *Photomedicine, Laser Photobiol. Photomed.*, 22:292–308 (1983).

Ramrus et al., "A Compact One–Half MV Rep–Rate Pulser", $20^{th}$ *IEEE Power Modulator Symposium*, pp. 68–71 (1992).

Ramrus et al., "Design and Performance of a One–Half MV Rep–Rate Pulser", Proc. Of the $8^{th}$ IEEE International Pulsed Power Conference, pp. 982–985 (1991).

Ranganathan et al., "Promises for Ultrasonic Waves on Activity of Silica Gel and Some Supported Catalystes", *Ind. Eng. Chem. Prod. Res. Develop.*, 12:155–158 (1973).

Rassing et al., "Measurement of Ultrasonic Absorption in a Gel by Light Diffraction and Resonator Methods", *J. Mol. Liq.*, 26:97–108 (1983).

Rastegar et al., "Technique for Measurement of One–Dimensional Instantaneous Ablation Velocity", *Lasers Surg. Med.*, 8:533–535 (1988).

Raulin et al., "Treatment of Nonresponding Port–Wine Stain With a New Pulsed Light Source (PhotoDerm® VL)", *Lasers Surg. Med.*, 21:203–208 (1997).

Raulin et al., "Treatment of Adult Port–Wine Stains Using Intense Pulsed Light Therapy (PhotoDerm VL): Brief Initial Clinical Report", *Dermatol. Surg.*, 23:594–601 (1997).

Raulin et al., "Treatment of benign venous malformations with an intense pulsed light source (PhotoDerm VL)", *Eur. J. Dermatol.*, 7:279–282 (1997).

Raulin et al., "Treatment of Essential Telangiectasias with an Intense Pulsed Light Source (PhotoDerm VL)", *Dermatol. Surg.*, 23:941–946 (1997).

Raulin et al., "Treatment of Port–wine Stains With a Noncoherent Pulsed Light Source", *Arch. Dermatol.*, 135:679–683 (1999).

Reyes et al., "Treatment of port–wine stains during childhood with the flashlamp–pumped pulse dye laser", *J. Am. Acad. Dermatol.*, 23:1142–1148 (1990).

Ross et al., "Effects of $CO_2$ Laser Pulse Duration in Ablation and Residual Thermal Damage: Implications for Skin Resurfacing", *Lasers Surg. Med.*, 19:123–129 (1996).

Rowe, P.M., "Photodynamic therapy begins to shine", *Lancet*, 351:1496 (1998).

Sadick et al., "Photorejuvenation with Intense Pulsed Light: Results of a Multi–Center Study", *J. Drugs Dermatol.*, 3(1):41–49 (2004).

Sadick, N.S., "A Structural Approach to Nonablative Rejuvenation", *Cosmetic Dermatol.*, 15(12):39–43 (2002).

Sadick, N.S., "Update on Non–Ablative Light Therapy for Rejuvenation: A Review", *Lasers Surg. Med.*, 32:120–128 (2003).

Schamiloglu et al., "Modern Pulsed Power: Charlie Martin and Beyond", *Proceedings of the IEEE*, 92(7):1014–1020 (2004).

Schroeter et al., "An Intense Light Source: The Photoderm VL–Flashlamp as a New Treatment Possibility for Vascular Skin Lesions", *Dermatol. Surg.*, 24:743–748 (1998).

Schroeter et al., "Clinical significance of an intense, pulsed light source on leg telangiectasias of up to 1mm diameter", *Eur. J. Dermatol.*, 7:38–42 (1997).

Schroeter et al., "Photoderm VL treatment of leg teleangiectasia", *JEADV*, 5(Suppl. 1):S49 (Abstract No. W76) (1995).

Schwimer et al., "The Effect of Ultrasound Coupling Gels on Sperm Motility In Vitro",*Fertil. Steril.*, 42:946–947 (1984).

Sheean et al., "Arrest of Embryo Development by Ultrasound Coupling Gels",*Fertil. Steril.*, 45:568–571 (1986).

Smith et al., "532–Nanometer Green Laser Beam Treatment of Superficial Varicosities of the Lower Extremities", *Lasers Surg. Med.*, 8: 130–134 (1988).

Steiger et al., "Comparison of Different Pulsed and Q–switched Solid–state Laser Systems for Endoscopic Laser Induced Shock Wave Lithotripsy: Performance and Laser/Stone Interactions", *SPIE*, 2300:94–101 (1990).

Strickland et al., "A 5kV, 250 kA Rep–Rated Pulser Using Parallel Ignitrons", *7th IEEE Int'l Pulsed Conf.*, pp. 729–731 (1989).

Sunde et al., "Traumatic Tattoo Removal: Comparison of Four Treatment Methods in an Animal Model with Correlation to Clinical Experience", *Lasers Surg. Med.*, 10:158–164 (1990).

Svaasand et al., "Light and Drug Distribution with Topically Administered Photosensitizers",*Lasers Surg. Med.*, 11:261–265 (1996).

Szeimies et al., "A Possible New Incoherent Lamp for Photodynamic Treatment of Superficial Skin Lesions", *Acta Derm. Venereol (Stockh).*, 74:117–119 (1994).

Tan et al., "Action Spectrum of Vascular Specific Injury Using Pulsed Irradiation", *J. Invest. Dermatol.*, 92(6):868–871 (1989).

Tan et al., "EMLA for Laser Treatment of Portwine Stains in Children",*Lasers Surg. Med.*, 12:543–548 (1992).

Tan et al., "Histologic Responses of Port–wine Stains Treated by Argon, Carbon Dioxide, and Tunable Dye Lasers", *Arch. Dermatol.*, 122:1016–1022 (1986).

Tan et al., "Pulsed Dye Laser Treatment of Recalcitrant Verrucae: A Preliminary Report",*Lasers Surg. Med.*, 13:127–137 (1993).

Tan et al., "Treatment of Children with Port–Wine Stains Using the Flashlamp–Pulsed Tunable Dye Laser", *N. Engl. J. Med.*, 320(7):416–421 (1989).

Taub, A.F., "Photodynamic Therapy: Other Uses", *Dermtol. Clin.*, 25:101–109 (2007).

Taylor et al., "Q–Switched Ruby Laser (QSRL) Irradiation of Benign Pigmented Lesions: Dermal vs. Epidermal", *Lasers Surg. Med.*, 3:65 (Abstract No. 262) (1991).

Templeton et al., "Comparison of infrared coagulation and rubber band ligation for first and second degree haemorrhoids: a randomized prospective clinical trial", *Br. Med. J.*, 286:1387–1389 (1983).

Troccoli et al., "Multiple–Pulse Photocoagulation of Blood Vessels With a 585 Nm Tunable Laser", *Lasers Surg. Med.*, 4:3 (Abstract No. 2) (1992).

van Gemert et al., "Can Physical Modeling Lead to an Optimal Laser Treatment Strategy for Port Wine Stains", in *Laser Applications in Medicine and Biology*, Chapter 5, pp. 199–247, Plenum Press, New York (1991).

van Germert et al., "Instantaneous Ablation Behavior of In–Vitro Rods During Laser Irradiation", *Lasers Surg. Med.*, 5:136 (Abstract No. 4) (1985).

van Germert et al., "Is There an Optimal Laser Treatment for Port Wine Stains?", *Lasers Surg. Med.*, 6:76–83 (1986).

van Germert et al., "Wavelengths for Laser Treatment of Port Wine Stains and Telangiectasia", *Lasers Surg. Med.*, 16:147–155 (1995).

"Varicose Vein Device Producer comes to U.S. Market", *Clinica*, 687:9 (Jan. 8, 1996).

Venning et al., "Tattoo removal using infra–red coagulation: a dose comparison", *Br. J. Dermatol.*, 117:99–105 (1987).

Wagner et al., "Percutalgine–Gel et Ultrasonotherapie en Pathologie du Sport", *La Revue de Medecine*, 32:1681–1683 (1982) (in French, with English Abstract Only).

Waldorf et al., "Skin Resurfacing of Fine to Deep Rhytides Using a Char–Free Carbon Dioxide Laser in 47 Patients", *Dermatol. Surg.*, 21:940–946 (1995).

Walsh et al., "Er:YAG Laser Ablation of Tissue: Measurement of Ablation Rates",*Lasers Surg. Med.*, 9:327–337 (1989).

Walsh et al., "Pulsed $CO_2$ Laser Tissue Ablation: Effect of Tissue Type and Pulse Duration On Thermal Damage", *Lasers Surg. Med.*, 8:108–118 (1988).

Walsh, J.T., "Er:YAG Laser Ablation of Tissue: Effect of Pulse Duration and Tissue Type on Thermal Damage", *Lasers Surg. Med.*, 9:314–326 (1989).

Walsh, J.T., "Pulsed Laser Ablation of Tissue: Analysis of the Removal Process and Tissue Healing", *Unpublished Ph.D. dissertation Massachusetts Institute of Technology*, on file with Institute Archives and Hayden Library, Massachusetts Institute of Technology, pp. 1–312 (1988).

Weiss et al., "Rejuvenation of Photoaged Skin: 5 Years Results with Intense Pulsed Light of the Face, Neck, and Chest", *Dermatol. Surg.*, 28:1115–1119 (2002).

Welch et al., "Practical Models for Light Distribution in Laser–Irradiated Tissue", *Lasers Surg. Med.*, 6:488–493 (1987).

Werner et al., "Die Hamangiombehandlung mit dem Neodym: Yttrium–Aluminum–Granat Laser (Nd:YAG–Laser)", *Laryngo–Rhino–Otol.*, 71:388–395 (1992), (in German, with English Abstract Only).

West, T., "How Laser Surgery Can Help Your Rosacea Patients", *Skin & Aging*, pp. 43–46 (1998).

Wilder, D., "Pulsed 1064–nm Nd:YAG Laser Therapy for Noninvasive Treatment of a Massive Hemangioma: Case Report",*J. Clin. Laser Med. Surg.*, 17(6):245–247 (1999).

Wilson et al., "The physics of photodynamic therapy",*Phys. Med. Biol.*, 31(4):327–360 (1986).

Gros, et al, Diaphanologie Mammaire, Memoires Originaux, *J. Radiol. Electrol.*, 53(4):297–306 (1972), in French, with English translation.

Brochure for an Infrared Coagulator by Redfield Corporation (1968).

Ramrus et al., "Design and Performance of a One–Half Rep–Rate Pulser," 1991.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2–7, 9 and 12 are cancelled.

Claims 1, 8, 10, 11, 14 and 15 are determined to be patentable as amended.

New claims 19–32 are added and determined to be patentable.

Claims 13 and 16–18 were not reexamined.

1. A therapeutic treatment device comprising:
[an incoherent light source] *a flashlamp* operable to provide a pulsed light output having a spectrum of frequencies continuous over at least one bandwidth for treatment;
a [housing with] *hand-held housing* unit defining an opening[, said light source being disposed in said housing, and said housing being] *and containing the flashlamp, the hand-held housing unit* suitable for being disposed adjacent a skin treatment area *and for treating an area of at least 2.5 centimeters*;
*at least one optical filter mounted within the hand-held housing unit; and*
*a control box including* a variable pulse-width pulse forming circuit electrically connected to [said light source] *the flashlamp via at least a flexible cable, wherein the flashlamp and the at least one optical filter are configured to provide pulses having a pulse width in the range of 5–20 milliseconds and an energy density of the light on the skin of about 6–20 Joules per square centimeter*; and
a reflector mounted within [said] *the hand-held* housing *unit* and proximate [said] *the* light source.

8. The device of claim [5] *1* wherein [said light source] *the hand-held housing unit* further comprises a fluorescent material disposed [about said] *between the* flash lamp *and the skin treatment area*, [said] *the* fluorescent material being of the type that absorbs radiation emitted by [said] *the* flashlamp and emits radiation in a range effective for skin thermolysis and coagulation of blood vessels in the skin and immediately thereunder, wherein [said] *the* optical filters are of the type that absorb radiation in the wavelength range of substantially less than 500 nm.

10. The device of claim [5, wherein said light source comprises] *1 further comprising* means for providing pulses having a width in the range of between [substantially 0.5 millisec] *about 10 milliseconds* and [10 millisec] *15 milliseconds* and an energy density of the light on the skin [of more than] *between 6 and 20* [J/cm²] *Joules per square centimeter*.

11. The device of claim [5, wherein said light source comprises] *1 further comprising* means for providing pulses having a width [in the range of between substantially 0.5 millisec and 10 millisec and an energy density of the light on the skin of more than 10 J/cm²] *selected from the group consisting of 10, 12, and 15 milliseconds*.

14. A method of treatment with light energy comprising [the steps of]:
providing a pulsed light output having a spectrum of frequencies continuous over at least one bandwidth [from] *using* a [non-laser, incoherent light source] *flashlamp*;
locating a hand-held unit including a light guide, a filter, and the flashlamp adjacent to an area of skin;
*filtering the pulsed light output to control the spectrum of the pulsed light output;*
directing [said] *the* pulsed light output to *at least a 2.5 square centimeter area that includes* skin irregularities, *wherein the pulsed light travels through the filter*;
*cooling the flashlamp with water;*
focusing [said light source] *the flashlamp* for controlling the power density of [said] *the* pulsed light output; and
[filtering and] controlling the [spectrum of said] *pulse-width of the* pulsed light output *via a pulse forming circuit disposed in a control box and operably coupled to the hand-held unit via a flexible cable*;
wherein [said step of] controlling the pulse-width includes [the step of] providing a pulse-width in the range of [substantially 0.5 millisec] *about 5 milliseconds* to [100 millisec] *20 milliseconds, and an energy density within 6–20 Joules per square centimeter*, whereby blood vessels are coagulated.

15. A method of treatment with light energy comprising [the steps of]:
providing a pulsed light output from a [non-laser, incoherent light source] *flashlamp*;
*locating a hand-held unit including a light guide, a filter, and the flashlamp adjacent to an area of skin;*
directing [said] *the* pulsed light output to *a treatment area of at least 2.5 square centimeters*;
controlling the pulse-width of [said] *the* pulsed light output;
focusing [said] *the* light source for controlling the power density of [said] *the* pulsed light output;
filtering and controlling the spectrum of [said] *the* pulsed light output;
providing a fluorescent material [surrounding] *within the hand-held unit and between the* the [light source] *flashlamp and the skin treatment area*;
absorbing radiation in the fluorescent material, [said] *the* radiation being emitted by [said light source] *the flashlamp*;
emitting radiation from the fluorescent material, the radiation having a wavelength in the range of [substantially] *about* 550 [to] *–*650 nm; and
absorbing radiation in the wavelength range substantially less than 500 nm.

19. *The treatment device of claim 1 wherein the hand-held unit includes two flashlamps.*

20. *The treatment device of claim 1 wherein the at least one optical filter can be moved into and out of the pulsed light output.*

21. *The treatment device of claim 1 comprising a reflector mounted within the hand-held unit and proximate to the flashlamp.*

22. *The treatment device of claim 21 wherein the reflector is circular.*

23. The treatment device of claim 1 wherein the variable pulse-width forming circuit includes a solid state switch.

24. The treatment of claim 1 wherein the flashlamp is cooled by water.

25. The treatment device of claim 1 comprising a simmer power supply.

26. An apparatus for providing light to the skin, comprising:

a hand-held unit including a flashlamp, a fluorescent material, a filter and a light guide;

a control box including a power supply and a pulse-width forming circuit;

a flexible cable configured to connect the hand-held unit to the control box, wherein the hand-held unit is configured to be disposed adjacent to the skin and configured to direct light to at least a 2.5 square centimeter area of skin, the filter is configured to transmit light having a wavelength of about 500–650 nm to the skin, and the pulse-width forming circuit is configured to pulse the flashlamp for about 10 to 15 milliseconds, wherein the energy density of the light on the skin is about 6 to 20 Joules per square centimeter; and a reflector mounted in the hand-held unit and proximate to the flashlamp.

27. The apparatus of claim 26 wherein the filter is configured to transmit light have a wavelength of about 540–650 nm.

28. The apparatus of claim 26 wherein the filter is configured to transmit light have a wavelength of about 570–650 nm.

29. The apparatus of claim 26 comprising at least another flashlamp in the hand-held unit.

30. The apparatus of claim 26 wherein the filter can be moved into or out of the path of the light.

31. The apparatus of claim 26 wherein the control box includes a simmer current power supply.

32. The apparatus of claim 26 wherein the hand-held unit includes cooling water flowing around the flashlamp.

* * * * *

(12) EX PARTE REEXAMINATION CERTIFICATE (7504th)
United States Patent
Eckhouse

(10) Number: US 5,405,368 C2
(45) Certificate Issued: May 11, 2010

(54) METHOD AND APPARATUS FOR THERAPEUTIC ELECTROMAGNETIC TREATMENT

(75) Inventor: Shimon Eckhouse, Haifa (IL)

(73) Assignee: Lumenis, Ltd., Yokneam (IL)

Reexamination Request:
No. 90/010,394, Jan. 23, 2009
No. 90/010,501, Apr. 22, 2009

Reexamination Certificate for:
Patent No.: 5,405,368
Issued: Apr. 11, 1995
Appl. No.: 07/964,210
Filed: Oct. 20, 1992

Reexamination Certificate C1 5,405,368 issued Mar. 24, 2009

(51) Int. Cl.
*A61N 5/06* (2006.01)

(52) U.S. Cl. .............. 607/88; 607/90; 607/94; 606/3; 606/9

(58) Field of Classification Search ............ None
See application file for complete search history.

(56) References Cited

U.S. PATENT DOCUMENTS

| | | | |
|---|---|---|---|
| 1,106,699 A | 8/1914 | Carroll | 600/200 |
| 1,651,385 A | 12/1927 | Goodrich | 392/409 |
| 2,699,771 A | 1/1955 | Ruttger-Pelli | 601/15 |
| 2,716,698 A | 8/1955 | Brukner | 240/1 |
| 2,888,927 A | 6/1959 | Fozard | 606/43 |
| 2,954,771 A | 10/1960 | Boyan | 128/396 |
| 3,126,295 A | 3/1964 | Young | 428/337 |
| 3,289,669 A | 12/1966 | Dwyer et al. | 600/565 |
| 3,307,553 A | 3/1967 | Liebner | 607/1 |
| 3,327,712 A | 6/1967 | Kaufman et al. | 606/40 |
| 3,538,919 A | 11/1970 | Meyer | 606/36 |
| 3,559,531 A | 2/1971 | Leibfritz et al. | 91/26 |
| 3,599,934 A | 8/1971 | Reed | 251/363 |
| 3,601,616 A | 8/1971 | Katsumata | 250/223 |
| 3,658,068 A | 4/1972 | McNall | 128/395 |

(Continued)

FOREIGN PATENT DOCUMENTS

| | | |
|---|---|---|
| AT | 355200 | 3/2006 |
| AU | 1851583 | 3/1984 |
| AU | 2940397 | 12/1997 |
| AU | 0691713 | 5/1998 |
| BE | 894290 | 3/1983 |
| CA | 1122156 | 4/1982 |
| CA | 1197563 | 12/1985 |
| CA | 1260116 | 9/1989 |
| CA | 2093055 | 10/1993 |
| CA | 2131750 | 1/1996 |

(Continued)

OTHER PUBLICATIONS

"Sharplan 771 Microscan Data Sheet", Mar. 28, 1985.
Alster et al., "Improvement of facial acne scars by the 585 nm flashlamp–pumped pulsed dye laser", *Journal of the American Academy of Dermatology*, 35(1):79–81 (Jul. 1996).

(Continued)

*Primary Examiner*—Beverly M. Flanagan

(57) ABSTRACT

A therapeutic treatment device includes a housing and an incoherent light source such as a flashlamp disposed in the housing. The flashlamp provides a pulsed light output for treatment of external skin disorders. To provide light to the treatment area the housing has an opening that is disposed adjacent a skin treatment area. A reflector is mounted within the housing near proximate the light source to reflect the light to the treatment area. At least one optical filter and an iris are mounted near the opening in the housing. Power to the lamp is provided by a pulse forming circuit that can provide a variable pulse width.

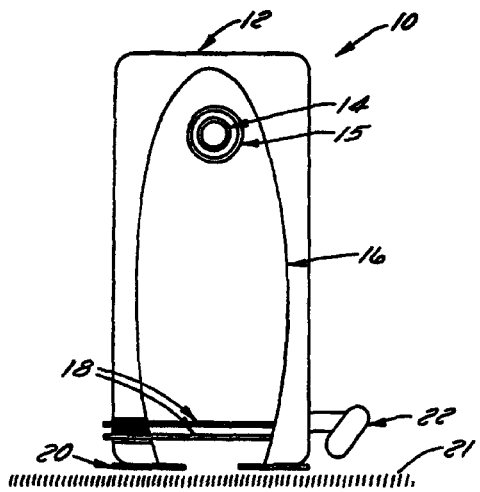

U.S. PATENT DOCUMENTS

| | | | |
|---|---|---|---|
| 3,680,000 A | 7/1972 | Chesler et al. | 372/99 |
| 3,693,623 A | 9/1972 | Harte et al. | 606/9 |
| 3,710,798 A | 1/1973 | Bredemeier | 606/11 |
| 3,804,732 A | 4/1974 | Goodkin | 204/58 |
| 3,806,829 A | 4/1974 | Duston et al. | 372/38.01 |
| 3,818,914 A | 6/1974 | Bender | 607/90 |
| 3,821,510 A | 6/1974 | Muncheryan | 219/121 |
| 3,834,391 A | 9/1974 | Block | 606/9 |
| 3,884,236 A | 5/1975 | Krasnov | 606/3 |
| 3,916,143 A | 10/1975 | Farrell | 219/121.69 |
| 3,930,504 A | 1/1976 | de Laforcade | 128/303.1 |
| 3,967,627 A | 7/1976 | Brown | 128/400 |
| 3,999,552 A | 12/1976 | Huggins | 128/303.13 |
| 4,022,534 A | 5/1977 | Kishner | 356/446 |
| 4,058,752 A | 11/1977 | Woods et al. | 315/360 |
| 4,112,335 A | 9/1978 | Gonser | 315/241 R |
| 4,122,853 A | 10/1978 | Smith | 606/4 |
| 4,174,714 A | 11/1979 | Mehl | 128/303.13 |
| 4,213,462 A | 7/1980 | Sato | 128/634 |
| 4,229,658 A | 10/1980 | Gonser | 250/504 H |
| 4,232,678 A | 11/1980 | Skovajsa | 128/395 |
| 4,233,493 A | 11/1980 | Nath | 219/354 |
| 4,241,382 A | 12/1980 | Daniel | 362/581 |
| 4,246,902 A | 1/1981 | Martinez | 604/22 |
| 4,266,548 A | 5/1981 | Davi | 606/14 |
| 4,283,661 A | 8/1981 | Doty | 315/360 |
| 4,298,005 A | 11/1981 | Mutzhas | 128/396 |
| 4,316,467 A | 2/1982 | Muckerheide | 606/9 |
| 4,321,930 A | 3/1982 | Jobsis et al. | 128/633 |
| 4,336,809 A | 6/1982 | Clark | 128/665 |
| 4,366,570 A | 12/1982 | Bees | 372/70 |
| 4,380,240 A | 4/1983 | Jobsis et al. | 128/633 |
| 4,381,007 A | 4/1983 | Doss | 128/303.1 |
| 4,387,952 A | 6/1983 | Slusher | 359/220.1 |
| 4,388,924 A | 6/1983 | Weissman et al. | 128/303.1 |
| 4,408,602 A | 10/1983 | Nakajima | 606/10 |
| 4,436,097 A | 3/1984 | Cunningham | 600/520 |
| 4,441,485 A | 4/1984 | Reynolds | 600/200 |
| 4,444,190 A | 4/1984 | Mutzhas | 128/396 |
| 4,454,882 A | 6/1984 | Takano | 607/89 |
| 4,469,098 A | 9/1984 | Davi | 606/7 |
| 4,497,018 A | 1/1985 | Rice | 363/96 |
| 4,503,854 A | 3/1985 | Jako | 606/11 |
| 4,506,196 A | 3/1985 | Bees | 315/241 R |
| 4,515,165 A | 5/1985 | Carroll | 600/475 |
| 4,516,195 A | 5/1985 | Gonser | 362/281 |
| 4,520,816 A | 6/1985 | Schachar et al. | 606/4 |
| 4,521,194 A | 6/1985 | Myers et al. | 433/215 |
| 4,539,987 A | 9/1985 | Nath et al. | 128/303.1 |
| 4,554,666 A | 11/1985 | Altman | 372/19 |
| 4,555,179 A | 11/1985 | Langerholc et al. | 356/342 |
| 4,559,942 A | 12/1985 | Eisenberg | 128/303 |
| 4,560,883 A | 12/1985 | Kerschgens | 250/504 |
| 4,564,011 A | 1/1986 | Goldman | 128/303.1 |
| 4,566,453 A | 1/1986 | Kumano et al. | 606/8 |
| 4,587,396 A | 5/1986 | Rubin | 219/121.78 |
| 4,601,037 A | 7/1986 | McDonald | 372/25 |
| 4,608,978 A | 9/1986 | Rohr | 606/9 |
| 4,608,979 A | 9/1986 | Breidenthal et al. | 128/303.1 |
| 4,611,245 A | 9/1986 | Trias et al. | 358/235 |
| 4,617,926 A | 10/1986 | Sutton | 606/9 |
| 4,619,887 A | 10/1986 | Hooper et al. | 430/313 |
| 4,620,547 A | 11/1986 | Boebel | 600/567 |
| 4,645,980 A | 2/1987 | Yang | 315/159 |
| 4,647,830 A | 3/1987 | Bees | 320/1 |
| 4,653,495 A | 3/1987 | Nanaumi | 128/303.1 |
| 4,657,018 A | 4/1987 | Hakky | 606/46 |
| 4,669,466 A | 6/1987 | L'Esperance | 606/3 |
| 4,672,969 A | 6/1987 | Dew | 128/397 |
| 4,686,986 A | 8/1987 | Fenyo et al. | 607/90 |
| 4,712,537 A | 12/1987 | Pender | 600/200 |
| 4,718,418 A | 1/1988 | L'Esperance, Jr. | 606/5 |
| 4,726,377 A | 2/1988 | Jegers et al. | 128/376 |
| 4,729,375 A | 3/1988 | Jegers et al. | 128/376 |
| 4,733,660 A | 3/1988 | Itzkan | 128/303.1 |
| 4,744,360 A | 5/1988 | Bath | 606/6 |
| 4,750,486 A | 6/1988 | Butler et al. | 606/18 |
| 4,754,381 A | 6/1988 | Downs | 362/297 |
| 4,757,431 A | 7/1988 | Cross et al. | 362/261 |
| 4,768,513 A | 9/1988 | Suzuki | 600/476 |
| 4,773,097 A | 9/1988 | Suzaki et al. | 382/128 |
| 4,775,361 A | 10/1988 | Jacques et al. | 604/20 |
| 4,784,135 A | 11/1988 | Blum et al. | 606/3 |
| 4,792,341 A | 12/1988 | Kozikowski et al. | 8/103 |
| 4,803,694 A | 2/1989 | Lee et al. | 372/98 |
| 4,810,658 A | 3/1989 | Shanks et al. | 436/172 |
| 4,818,230 A | 4/1989 | Myers et al. | 433/215 |
| 4,818,847 A | 4/1989 | Hara et al. | 235/455 |
| 4,829,262 A | 5/1989 | Furumoto | 330/4.3 |
| 4,835,749 A | 5/1989 | Welton | 368/10 |
| 4,839,562 A | 6/1989 | Francis et al. | 315/149 |
| 4,840,798 A | 6/1989 | Skaliotis | 424/488 |
| 4,846,172 A | 7/1989 | Berlin | 606/4 |
| 4,846,192 A | 7/1989 | MacDonald | 600/565 |
| 4,851,738 A | 7/1989 | Yang | 315/159 |
| 4,858,090 A | 8/1989 | Downs | 362/297 |
| 4,860,172 A | 8/1989 | Schlager et al. | 362/553 |
| 4,862,886 A | 9/1989 | Clarke et al. | 606/7 |
| 4,871,559 A | 10/1989 | Dunn et al. | 426/248 |
| 4,874,009 A | 10/1989 | Pickerrell et al. | 137/454.6 |
| 4,874,361 A | 10/1989 | Obagi | 606/3 |
| 4,875,214 A | 10/1989 | Denne | 372/5 |
| 4,883,333 A | 11/1989 | Yanez | 385/33 |
| 4,884,568 A | 12/1989 | Hahn | 128/303.1 |
| 4,894,547 A | 1/1990 | Leffell et al. | 250/461.2 |
| 4,897,771 A | 1/1990 | Parker | 362/298 |
| 4,907,235 A | 3/1990 | Kuizenga | 372/21 |
| 4,909,782 A | 3/1990 | Semm et al. | 606/171 |
| 4,910,942 A | 3/1990 | Dunn | 53/425 |
| 4,913,132 A | 4/1990 | Gabriel | 600/200 |
| 4,917,083 A | 4/1990 | Harrington et al. | 606/15 |
| 4,917,084 A | 4/1990 | Sinofsky | 606/7 |
| 4,917,486 A | 4/1990 | Raven et al. | 351/221 |
| 4,926,861 A | 5/1990 | Fenyo et al. | 607/88 |
| 4,930,504 A | 6/1990 | Diamantopoulos et al. | 128/395 |
| 4,938,221 A | 7/1990 | Tuffel | 128/401 |
| 4,940,922 A | 7/1990 | Schuda et al. | 315/246 |
| 4,941,082 A | 7/1990 | Pailthorp et al. | 700/57 |
| 4,945,914 A | 8/1990 | Allen | 600/426 |
| 4,947,305 A | 8/1990 | Gunter, Jr. | 362/297 |
| 4,947,859 A | 8/1990 | Brewer et al. | 128/715 |
| 4,950,880 A | 8/1990 | Hayner | 250/201.9 |
| 4,955,882 A | 9/1990 | Hakky | 606/14 |
| 4,973,848 A | 11/1990 | Kolobanov et al. | 250/458.1 |
| 4,974,138 A | 11/1990 | Negishi | 362/347 |
| 4,976,709 A | 12/1990 | Sand | 606/5 |
| 4,988,163 A | 1/1991 | Cohen et al. | 385/31 |
| 4,996,046 A | 2/1991 | Warshaw et al. | 424/445 |
| 5,000,752 A | 3/1991 | Hoskin et al. | 606/9 |
| 5,005,180 A | 4/1991 | Edelman et al. | 372/57 |
| 5,008,579 A | 4/1991 | Conley et al. | 310/303 |
| 5,011,793 A | 4/1991 | Obinata | 427/383.1 |
| 5,016,151 A | 5/1991 | Mula | 362/267 |
| 5,020,995 A | 6/1991 | Levy | 433/215 |
| 5,023,886 A | 6/1991 | Hobart et al. | 372/99 |
| 5,025,446 A | 6/1991 | Kuizenga | 372/21 |
| 5,034,235 A | 7/1991 | Dunn et al. | 426/238 |
| 5,039,867 A | 8/1991 | Nishihara et al. | 250/492.3 |
| 5,048,034 A | 9/1991 | Tulip | 372/41 |
| 5,049,147 A | 9/1991 | Danon | 606/10 |
| 5,054,488 A | 10/1991 | Muz | 128/633 |

| Patent No. | Date | Inventor | Class |
|---|---|---|---|
| 5,057,100 A | 10/1991 | Lombardo | 606/17 |
| 5,057,104 A | 10/1991 | Chess | 606/9 |
| 5,059,192 A | 10/1991 | Zaias | 606/9 |
| 5,063,961 A | 11/1991 | Brunner | 137/454.5 |
| 5,066,291 A | 11/1991 | Stewart | 606/3 |
| 5,066,293 A | 11/1991 | Furumoto | 606/9 |
| 5,071,417 A | 12/1991 | Sinofsky | 606/8 |
| 5,071,422 A | 12/1991 | Watson et al. | 606/128 |
| 5,074,861 A | 12/1991 | Schneider et al. | 606/17 |
| 5,077,099 A | 12/1991 | Kukanskis et al. | 427/437 |
| 5,078,711 A | 1/1992 | Kakami et al. | 606/16 |
| 5,083,093 A | 1/1992 | Adler et al. | 328/65 |
| 5,084,881 A | 1/1992 | Farries et al. | 372/6 |
| 5,089,945 A | 2/1992 | Mula | 362/261 |
| 5,097,471 A | 3/1992 | Negus et al. | 372/18 |
| 5,106,364 A | 4/1992 | Hayafuji et al. | 604/22 |
| 5,109,463 A | 4/1992 | Lee | 385/123 |
| 5,112,328 A | 5/1992 | Taboada et al. | 606/4 |
| 5,113,462 A | 5/1992 | Clancy et al. | 385/53 |
| 5,123,026 A | 6/1992 | Fan et al. | 372/75 |
| 5,125,922 A | 6/1992 | Dwyer et al. | 606/3 |
| 5,126,621 A | 6/1992 | Morton et al. | 313/237 |
| 5,130,997 A | 7/1992 | Ortiz et al. | 372/21 |
| 5,133,035 A | 7/1992 | Hicks | 385/117 |
| 5,137,539 A | 8/1992 | Bowling | 44/626 |
| 5,139,494 A | 8/1992 | Freiberg | 606/3 |
| 5,146,923 A | 9/1992 | Dhawan | 600/476 |
| 5,161,526 A | 11/1992 | Hellwing et al. | 607/89 |
| 5,178,617 A | 1/1993 | Kuizenga et al. | 606/17 |
| 5,194,723 A | 3/1993 | Cates et al. | 250/205 |
| 5,200,604 A | 4/1993 | Rudko et al. | 250/205 |
| 5,201,731 A | 4/1993 | Hakky | 606/15 |
| 5,204,517 A | 4/1993 | Cates et al. | 250/205 |
| 5,206,867 A | 4/1993 | Esterowitz et al. | 372/20 |
| 5,207,670 A | 5/1993 | Sinofsky | 606/8 |
| 5,207,671 A | 5/1993 | Franken et al. | 606/9 |
| 5,217,455 A | 6/1993 | Tan | 606/9 |
| 5,222,952 A | 6/1993 | Loertscher | 606/6 |
| 5,226,107 A | 7/1993 | Stern et al. | 392/416 |
| 5,226,430 A | 7/1993 | Spears et al. | 128/898 |
| 5,226,907 A | 7/1993 | Tankovich | 606/133 |
| 5,242,460 A | 9/1993 | Klein et al. | 606/159 |
| 5,243,615 A | 9/1993 | Ortiz et al. | 372/34 |
| 5,246,435 A | 9/1993 | Bille et al. | 606/6 |
| 5,246,436 A | 9/1993 | Rowe | 606/13 |
| 5,247,935 A | 9/1993 | Cline et al. | 128/653.2 |
| 5,249,190 A | 9/1993 | Kortz et al. | 372/22 |
| 5,257,274 A | 10/1993 | Barrett et al. | 372/20 |
| 5,259,380 A | 11/1993 | Mendes et al. | 607/115 |
| 5,263,038 A | 11/1993 | Lukas et al. | 372/22 |
| 5,263,950 A | 11/1993 | L'Esperance, Jr. | 606/6 |
| 5,265,598 A | 11/1993 | Searfoss et al. | 607/88 |
| 5,269,778 A | 12/1993 | Rink et al. | 606/12 |
| 5,272,518 A | 12/1993 | Vincent | 356/405 |
| 5,272,713 A | 12/1993 | Sobey et al. | 372/69 |
| 5,274,728 A | 12/1993 | Tran | 385/142 |
| 5,280,378 A | 1/1994 | Lombardo | 359/199.1 |
| 5,281,798 A | 1/1994 | Hamm et al. | 250/205 |
| 5,282,797 A | 2/1994 | Chess | 606/9 |
| 5,282,798 A | 2/1994 | Bruse et al. | 606/17 |
| 5,287,380 A | 2/1994 | Hsia | 372/69 |
| 5,289,479 A | 2/1994 | Oka et al. | 372/22 |
| 5,290,273 A | 3/1994 | Tan | 606/9 |
| 5,290,274 A | 3/1994 | Levy et al. | 606/13 |
| 5,293,872 A | 3/1994 | Alfano | 128/664 |
| 5,300,097 A | 4/1994 | Lerner et al. | 607/93 |
| 5,304,167 A | 4/1994 | Freiberg | 606/3 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,312,396 A | 5/1994 | Feld et al. | 606/11 |
| 5,312,399 A | 5/1994 | Hakky et al. | 606/15 |
| 5,320,618 A | 6/1994 | Gustafsson | 606/9 |
| 5,321,715 A | 6/1994 | Trost | 372/69 |
| 5,325,458 A | 6/1994 | Morrow et al. | 385/125 |
| 5,328,488 A | 7/1994 | Daikuzono | 606/16 |
| 5,328,517 A | 7/1994 | Cates et al. | 134/7 |
| 5,330,517 A | 7/1994 | Mordon et al. | 607/89 |
| 5,334,190 A | 8/1994 | Seiler | 606/5 |
| 5,336,216 A | 8/1994 | Dewey | 606/4 |
| 5,336,217 A | 8/1994 | Buys et al. | 606/9 |
| 5,337,741 A | 8/1994 | Diamond | 600/8 |
| 5,342,198 A | 8/1994 | Vassiliadis et al. | 433/215 |
| 5,344,418 A | 9/1994 | Ghaffari | 606/9 |
| 5,344,433 A | 9/1994 | Talmore | 607/88 |
| 5,344,434 A | 9/1994 | Talmore | 607/88 |
| 5,345,457 A | 9/1994 | Zenzie et al. | 372/22 |
| 5,349,590 A | 9/1994 | Amirkhanian et al. | 372/6 |
| 5,360,424 A | 11/1994 | Klopotek | 606/4 |
| 5,363,387 A | 11/1994 | Sinofsky | 372/15 |
| 5,363,854 A | 11/1994 | Martens et al. | 600/477 |
| 5,364,390 A | 11/1994 | Taboada et al. | 606/10 |
| 5,368,031 A | 11/1994 | Cline et al. | 600/411 |
| 5,368,634 A | 11/1994 | Hackett | 95/260 |
| 5,370,651 A | 12/1994 | Summers | 606/159 |
| 5,374,265 A | 12/1994 | Sand | 606/5 |
| 5,375,132 A | 12/1994 | Connors et al. | 372/34 |
| 5,382,013 A | 1/1995 | Walsh | 271/186 |
| 5,383,467 A | 1/1995 | Auer | 128/664 |
| 5,384,796 A | 1/1995 | Jee | 372/22 |
| 5,386,837 A | 2/1995 | Sterzer | 128/898 |
| 5,387,211 A | 2/1995 | Saadatmanesh et al. | 606/10 |
| 5,390,204 A | 2/1995 | Yessik | 372/38 |
| 5,394,307 A | 2/1995 | Matsuura | 362/16 |
| 5,395,362 A | 3/1995 | Sacharoff et al. | 606/17 |
| 5,397,327 A | 3/1995 | Koop et al. | 606/17 |
| 5,400,428 A | 3/1995 | Grace | 385/115 |
| 5,400,791 A | 3/1995 | Schlier et al. | 128/664 |
| 5,401,171 A | 3/1995 | Paghdiwala | 433/215 |
| 5,403,276 A | 4/1995 | Schechter et al. | 604/22 |
| 5,405,368 A | 4/1995 | Eckhouse | 607/88 |
| 5,405,726 A | 4/1995 | Abe et al. | 430/97 |
| 5,406,577 A | 4/1995 | Gagosz | 372/69 |
| 5,409,479 A | 4/1995 | Dew et al. | 606/9 |
| 5,409,483 A | 4/1995 | Campbell et al. | 606/15 |
| 5,411,502 A | 5/1995 | Zair | 606/10 |
| 5,414,600 A | 5/1995 | Strobl et al. | 362/551 |
| 5,422,899 A | 6/1995 | Freiberg et al. | 372/25 |
| 5,423,798 A | 6/1995 | Crow | 606/4 |
| 5,423,803 A | 6/1995 | Tankovich et al. | 606/9 |
| 5,425,728 A | 6/1995 | Tankovich | 606/9 |
| 5,431,646 A | 7/1995 | Vassiliadis et al. | 606/6 |
| 5,435,724 A | 7/1995 | Goodman et al. | 433/215 |
| 5,438,303 A | 8/1995 | Murakami et al. | 332/109 |
| 5,441,531 A | 8/1995 | Zarate et al. | |
| 5,445,146 A | 8/1995 | Bellinger | 607/89 |
| D363,349 S | 10/1995 | Dittert | D24/158 |
| 5,454,807 A | 10/1995 | Lennox et al. | 606/15 |
| 5,456,689 A | 10/1995 | Kresch et al. | 606/180 |
| 5,458,112 A | 10/1995 | Weaver | 600/566 |
| 5,474,528 A | 12/1995 | Meserol | 604/20 |
| 5,474,549 A | 12/1995 | Ortiz et al. | 606/9 |
| 5,476,461 A | 12/1995 | Cho et al. | 606/15 |
| 5,484,432 A | 1/1996 | Sand | 606/5 |
| 5,489,279 A | 2/1996 | Meserol | 604/290 |
| 5,490,860 A | 2/1996 | Middle et al. | 606/171 |
| 5,498,258 A | 3/1996 | Hakky et al. | 606/15 |
| 5,498,935 A | 3/1996 | McMahan et al. | 315/241 P |
| 5,501,680 A | 3/1996 | Kurtz et al. | 606/9 |
| 5,511,563 A | 4/1996 | Diamond | 128/898 |
| 5,520,679 A | 5/1996 | Lin | 606/5 |
| 5,522,814 A | 6/1996 | Bernaz | 606/36 |

| Patent No. | Date | Inventor | Class |
|---|---|---|---|
| 5,527,332 A | 6/1996 | Clement | 606/171 |
| 5,527,350 A | 6/1996 | Grove et al. | 607/89 |
| 5,529,954 A | 6/1996 | Iijima et al. | 438/653 |
| 5,531,739 A | 7/1996 | Trelles | 606/2.5 |
| 5,531,740 A | 7/1996 | Black | 606/9 |
| 5,540,676 A | 7/1996 | Freiberg | 606/3 |
| 5,544,651 A | 8/1996 | Wilk | 600/310 |
| 5,546,214 A | 8/1996 | Black et al. | 359/203 |
| 5,558,666 A | 9/1996 | Dewey et al. | 606/9 |
| 5,558,667 A | 9/1996 | Yarborough et al. | 606/9 |
| 5,560,699 A | 10/1996 | Davenport et al. | 362/558 |
| 5,569,284 A | 10/1996 | Young et al. | 606/180 |
| 5,572,311 A | 11/1996 | Abe | 399/127 |
| 5,578,029 A | 11/1996 | Trelles et al. | 606/25 |
| 5,586,981 A | 12/1996 | Hu | 606/9 |
| 5,588,428 A | 12/1996 | Smith et al. | 600/425 |
| 5,591,157 A | 1/1997 | Hennings et al. | 606/3 |
| 5,595,568 A | 1/1997 | Anderson et al. | 606/9 |
| 5,599,342 A | 2/1997 | Hsia et al. | 606/9 |
| 5,606,798 A | 3/1997 | Kelman | 30/41.5 |
| 5,608,520 A | 3/1997 | Fleming | 356/318 |
| 5,611,795 A | 3/1997 | Slatkine et al. | 606/9 |
| 5,618,284 A | 4/1997 | Sand | 606/5 |
| 5,618,285 A | 4/1997 | Zair | 606/10 |
| 5,620,478 A | 4/1997 | Eckhouse | 607/88 |
| 5,621,745 A | 4/1997 | Yessik et al. | 372/26 |
| 5,626,631 A | 5/1997 | Eckhouse | 607/88 |
| 5,628,744 A | 5/1997 | Coleman et al. | 606/12 |
| 5,630,811 A | 5/1997 | Miller | 606/9 |
| 5,642,370 A | 6/1997 | Mitchell et al. | 372/25 |
| 5,643,334 A | 7/1997 | Eckhouse et al. | 697/88 |
| 5,644,585 A | 7/1997 | Mitchell et al. | 372/25 |
| 5,649,972 A | 7/1997 | Hochstein | 607/100 |
| 5,655,547 A | 8/1997 | Karni | 128/898 |
| 5,658,323 A | 8/1997 | Miller | 607/89 |
| 5,660,836 A | 8/1997 | Knowlton | 424/400 |
| 5,662,644 A | 9/1997 | Swor | 606/9 |
| 5,683,380 A | 11/1997 | Eckhouse et al. | 606/9 |
| 5,707,413 A | 1/1998 | Inao | 65/78 |
| 5,710,626 A | 1/1998 | O'rourke et al. | 356/301 |
| 5,720,772 A | 2/1998 | Eckhouse | 607/88 |
| 5,722,970 A | 3/1998 | Colvard et al. | 606/3 |
| 5,725,565 A | 3/1998 | Smith | 607/88 |
| 5,733,277 A | 3/1998 | Pallarito | 606/7 |
| 5,733,297 A | 3/1998 | Wang | 606/167 |
| 5,735,844 A | 4/1998 | Anderson et al. | 606/9 |
| 5,738,677 A | 4/1998 | Colvard et al. | 606/4 |
| 5,741,245 A | 4/1998 | Cozean et al. | 606/5 |
| 5,743,902 A | 4/1998 | Trost | 606/18 |
| 5,748,655 A | 5/1998 | Yessik et al. | 372/22 |
| 5,749,868 A | 5/1998 | Furumoto | 606/9 |
| 5,754,573 A | 5/1998 | Yarborough et al. | 372/22 |
| 5,755,751 A | 5/1998 | Eckhouse | 607/88 |
| 5,755,753 A | 5/1998 | Knowlton | 607/98 |
| 5,769,844 A | 6/1998 | Ghaffari | 606/16 |
| 5,776,175 A | 7/1998 | Eckhouse et al. | 607/100 |
| 5,783,798 A | 7/1998 | Abraham | 219/121.73 |
| 5,786,929 A | 7/1998 | Nabors | 359/330 |
| 5,810,801 A | 9/1998 | Anderson et al. | 606/9 |
| 5,814,040 A | 9/1998 | Nelson et al. | 606/9 |
| 5,817,089 A | 10/1998 | Tankovich et al. | 606/9 |
| 5,817,090 A | 10/1998 | Abergel et al. | 606/9 |
| 5,828,803 A | 10/1998 | Eckhouse | 385/88 |
| 5,830,208 A | 11/1998 | Muller | 606/9 |
| 5,833,612 A | 11/1998 | Eckhouse et al. | 600/476 |
| 5,833,683 A | 11/1998 | Fuller et al. | 606/17 |
| 5,836,939 A | 11/1998 | Negus et al. | 606/11 |
| 5,836,999 A | 11/1998 | Eckhouse et al. | 607/88 |
| 5,843,143 A | 12/1998 | Whitehurst | 607/88 |
| 5,849,029 A | 12/1998 | Eckhouse et al. | 607/104 |
| 5,853,407 A | 12/1998 | Miller | 606/9 |
| 5,855,595 A | 1/1999 | Fujishima et al. | 607/90 |
| 5,860,967 A | 1/1999 | Zavislan et al. | 606/9 |
| 5,860,968 A | 1/1999 | Wojcik et al. | 606/10 |
| 5,865,830 A | 2/1999 | Parel et al. | 606/5 |
| 5,871,479 A | 2/1999 | Furumoto et al. | 606/9 |
| 5,879,346 A | 3/1999 | Waldman et al. | 606/9 |
| 5,879,376 A | 3/1999 | Miller | 607/89 |
| 5,885,273 A | 3/1999 | Eckhouse et al. | 606/9 |
| 5,885,274 A | 3/1999 | Fullmer | 606/9 |
| 5,900,211 A | 5/1999 | Dunn et al. | 422/24 |
| 5,906,609 A | 5/1999 | Assa et al. | 606/9 |
| 5,907,574 A | 5/1999 | Karni | 372/95 |
| 5,911,718 A | 6/1999 | Yarborough et al. | 606/9 |
| 5,912,457 A | 6/1999 | Mcquaid | 240/227.17 |
| 5,938,657 A | 8/1999 | Assa et al. | 606/9 |
| 5,957,915 A | 9/1999 | Trost | 606/13 |
| 5,970,983 A | 10/1999 | Karni et al. | 128/898 |
| 5,983,900 A | 11/1999 | Clement et al. | 128/898 |
| 6,024,751 A | 2/2000 | Lovato et al. | 606/170 |
| RE36,634 E | 3/2000 | Ghaffari | 606/9 |
| 6,045,548 A | 4/2000 | Furumoto et al. | 606/9 |
| 6,077,294 A | 6/2000 | Cho et al. | 607/89 |
| 6,090,101 A | 7/2000 | Quon et al. | 606/9 |
| 6,096,031 A | 8/2000 | Mitchell et al. | 606/15 |
| 6,130,900 A | 10/2000 | Black et al. | 372/25 |
| 6,139,712 A | 10/2000 | Patton et al. | 205/143 |
| 6,165,170 A | 12/2000 | Wynne et al. | 606/9 |
| 6,171,302 B1 | 1/2001 | Talpalriu et al. | 606/9 |
| 6,171,332 B1 | 1/2001 | Whitehurst | 607/89 |
| 6,190,376 B1 | 2/2001 | Asah et al. | 606/9 |
| 6,193,711 B1 | 2/2001 | Connors et al. | 606/12 |
| 6,235,016 B1 | 5/2001 | Stewart | 606/9 |
| 6,280,438 B1 | 8/2001 | Eckhouse et al. | 606/9 |
| 6,282,223 B1 | 8/2001 | Angeley | 372/92 |
| 6,289,236 B1 | 9/2001 | Koenig et al. | 600/477 |
| 6,379,376 B1 | 4/2002 | Lubart | 607/88 |
| 6,387,089 B1 | 5/2002 | Kreindel et al. | 606/9 |
| 6,451,010 B1 | 9/2002 | Angeley | 606/17 |
| 6,475,138 B1 | 11/2002 | Schechter et al. | 600/108 |
| 6,505,059 B1 | 1/2003 | Kollias et al. | 600/316 |
| 6,514,243 B1 | 2/2003 | Eckhouse et al. | 606/9 |
| 6,522,911 B1 | 2/2003 | Toida et al. | 600/473 |
| 6,544,585 B1 | 4/2003 | Kuriyama et al. | 216/18 |
| 6,702,838 B1 | 3/2004 | Andersen et al. | 607/89 |
| 6,766,187 B1 | 7/2004 | Black et al. | 600/473 |

FOREIGN PATENT DOCUMENTS

| | | |
|---|---|---|
| CA | 2168624 | 8/1996 |
| CH | 416861 | 7/1966 |
| DE | 565331 | 11/1932 |
| DE | 2308554 | 8/1974 |
| DE | 2740179 | 3/1978 |
| DE | 2717421 | 11/1978 |
| DE | 27 17 421 A1 | 11/1978 |
| DE | 2740969 | 3/1979 |
| DE | 7901050 | 5/1979 |
| DE | 2901534 | 7/1979 |
| DE | 2846471 | 5/1980 |
| DE | 2948580 | 6/1980 |
| DE | 3220218 | 3/1983 |
| DE | 3330293 | 3/1985 |
| DE | 3804732 | 8/1989 |
| DE | 3906860 | 9/1989 |
| DE | 4031320 A | 4/1992 |
| DE | 9304869 | 9/1993 |
| DE | 9321497 | 8/1998 |
| EP | 0003312 | 8/1979 |
| EP | 0052765 | 6/1982 |
| EP | 0075860 | 4/1983 |
| EP | 0172490 | 2/1986 |
| EP | 0185810 | 7/1986 |

| | | |
|---|---|---|
| EP | 0198257 | 10/1986 |
| EP | 0240990 | 10/1987 |
| EP | 0310285 | 4/1989 |
| EP | 0324490 | 7/1989 |
| EP | 0335714 | 10/1989 |
| EP | 0429297 | 5/1991 |
| EP | 0480995 | 4/1992 |
| EP | 0527050 | 2/1993 |
| EP | 0565331 A2 | 10/1993 |
| EP | 0575274 | 12/1993 |
| EP | 0626229 | 11/1994 |
| EP | 0724292 | 7/1996 |
| EP | 0724894 | 8/1996 |
| EP | 0736308 | 10/1996 |
| EP | 0753285 A1 | 1/1997 |
| EP | 0763371 | 3/1997 |
| EP | 0807418 | 11/1997 |
| EP | 0880168 | 11/1998 |
| EP | 0885629 | 12/1998 |
| EP | 1078604 | 2/2001 |
| EP | 1078605 | 2/2001 |
| ES | 8306601 | 9/1983 |
| FI | 822940 | 3/1983 |
| FI | 0931608 | 10/1993 |
| FR | 2193628 | 2/1974 |
| FR | 2342745 | 9/1977 |
| FR | 2364038 | 4/1978 |
| FR | 2389229 | 11/1978 |
| FR | 2571264 | 4/1986 |
| GB | 1116465 | 6/1968 |
| GB | 2012939 | 8/1979 |
| GB | 2105195 | 3/1983 |
| GB | 2218660 | 11/1989 |
| HU | 181836 | 11/1983 |
| HU | 186081 | 5/1985 |
| IL | 101547 | 12/1996 |
| JP | 52109387 | 9/1977 |
| JP | 53105083 | 9/1978 |
| JP | 55117166 | 9/1980 |
| JP | 56109654 | 8/1981 |
| JP | 56124451 | 9/1981 |
| JP | 56137140 | 10/1981 |
| JP | 58086178 | 5/1983 |
| JP | 60006871 | 1/1985 |
| JP | 60132571 | 7/1985 |
| JP | 62114543 | 5/1987 |
| JP | 63277771 | 11/1988 |
| JP | 1034378 | 2/1989 |
| JP | 64012402 | 2/1989 |
| JP | 1240694 | 9/1989 |
| JP | 2154753 | 6/1990 |
| JP | 3016956 | 1/1991 |
| JP | H3-128069 | 5/1991 |
| JP | 3211287 | 9/1991 |
| JP | 3233986 | 10/1991 |
| JP | HEI-4-53569 | 2/1992 |
| JP | 4067860 | 3/1992 |
| JP | 4079966 | 3/1992 |
| JP | 4-90360 | 8/1992 |
| JP | 5001559 | 1/1993 |
| JP | 5029089 | 2/1993 |
| JP | 5111539 | 5/1993 |
| JP | 6063165 | 3/1994 |
| JP | 6198945 | 7/1994 |
| JP | 7008281 | 1/1995 |
| JP | 7275380 | 10/1995 |
| JP | 7308300 | 11/1995 |
| JP | 86266326 | 10/1996 |
| LU | 84349 | 6/1983 |
| SE | 416861 | 2/1981 |
| SE | 452852 | 12/1987 |
| SE | 465 953 B | 11/1991 |
| SE | 515325 | 7/2001 |
| SU | 1347142 | 10/1987 |
| WO | WO 80/02640 | 12/1980 |
| WO | WO 84/03049 | 8/1984 |
| WO | WO 84/04463 | 11/1984 |
| WO | WO 89/00871 | 2/1989 |
| WO | WO 89/11261 | 11/1989 |
| WO | WO 90/12545 | 11/1990 |
| WO | WO 90/14836 | 12/1990 |
| WO | WO 91/00063 | 1/1991 |
| WO | WO 91/12766 | 9/1991 |
| WO | WO 91/13652 | 9/1991 |
| WO | WO 91/15264 | 10/1991 |
| WO | WO 92/19165 | 11/1992 |
| WO | WO 93/08715 | 5/1993 |
| WO | WO 95/15725 | 6/1995 |
| WO | WO 96/21490 | 7/1996 |
| WO | WO 96/32895 | 10/1996 |
| WO | WO 96/33538 | 10/1996 |
| WO | WO 96/41577 | 12/1996 |
| WO | WO 97/37602 | 10/1997 |
| WO | WO 98/52645 | 11/1998 |
| WO | WO 99/25905 | 5/1999 |
| WO | WO 99/55243 | 11/1999 |
| WO | WO 00/32835 | 6/2000 |

OTHER PUBLICATIONS

Alster et al., "Treatment of Scars: A Review", *Annuals of Plastic Surgery*, 39(4):418–432 (Oct. 1997).

Anderson et al., "Selective Photothermolysis: Precise Microsurgery by Selective Absorption of Pulsed Radiation", *Science*, 220:524–527 (Apr. 1993).

Anderson et al., "Pulsed photothermal radiometry in turbid media: internal reflection of backscattered radiation strongly influences optical dosimetry", *Applied Optics*, 28(12):2256–2262 (1989).

Anderson et al., "Microvasculature can be selectively damaged using dye lasers: basic theories and experimental evidence in human skin", *Laser in Surg. Med.*, 1:263–276 (1981).

Arthrex, Inc., "Single Use Shaver Blades and Burs", (1996).

Birngruber et al., "Fundus Reflectometry: A Step towards Optimization of the Retina Photocoagulation", *Mod. Probl. Ophthal.*, 18:383–390 (1977).

Blitzer, "Laser Photocoagulation in the Care of Patients with Osler–Weber–Rendu Disease", *Operative Techniques in Otolaryngology—Head and Neck Surgery*, 5(4):274–277 (Dec. 1994).

Boulnois, "Photophysical Processes in Recent Medical Laser Developments: A Review", *Lasers in Medical Science*, 1:47–64 (1986).

Brauner et al., "Treatment of Pigmented Lesions with the Flashlamp Pumped PL DL ("Brown Spot") Laser", *Laser Med. And Surgery Abstracts*, 4:73 (Sep. 1992).

Cisneros et al., "The Q–switched Neodymium (Nd): YAG Laser with Quadruple Frequency", *Dermatol. Surg.*, 24:345–350 (1998).

Dagan et al., "Microprocessor—Controlled Scanning Micromanipulator for Carbon–Dioxide Laser Surgery", *J. Neurosurgery*, 59:1098–1099 (Dec. 1983).

Fitzpatrick et al., "Treatment of Benign Cutaneous Pigmented Lesions with the Candela 510 NM Pulsed Laser", *Laser Med. and Surgery Abstracts*, 4S:73 (Sep. 1992).

Frauchiger et al., "Laser properties of selectively excited YAlO$_3$:Er", *Optic Letters*, 13(11):964–966 (1988).

Gabay et al., "Modelling the Assessment of Port Wine Stain Parameters From Skin Surface Temperature Following a Diagnostic Laser Pulse", *Lasers in Surgery and Medicine*, 20(2):179–187 (1997).

Geeraets et al., "Light Reflectance of the Ocular Fundus", *Archives of Ophthalmology*, 69:612–617 (May 1963).

Gustafsson et al., "A Variable Pulsewidth Vascular System for Dermatology", *SPIE*, 2128:186–196 (1994).

Hacker et al., "The Effect of Flash Lamp–Pulsed Dye Laser on Psoriasis", *Archives of Dermatology*, 128:853–855 (Jun. 1992).

Herloski et al., "Gaussian beam ray–equivalent modeling and optical design", *Applied Optics*, 22(8):1168–1174 (1983).

International Search Report, dated Jul. 24, 1996, for International Application No. PCT/US96/04515, 4 pages.

Ishimaru, "Diffusion of Light in Turbid Material", *Applied Optics*, 28(12):2210–2215 (1989).

Jacques et al., "The Role of Skin Optics in Diagnostic and Therapeutic Uses of Lasers", *Lasers in Dermatology*, 1–21 (1991).

Jerath et al., "Calibrated real–time control for lesion size based on reflectance images", *Applied Optics*, 32(7):1200–1209 (Mar. 1993).

Jerath et al., "Reflectance Feedback Control of Photocoagulation In Vivo", *Arch Ophthalmol*, 111:531–534 (Apr. 1993).

Jeys et al., "Sum fequency generation of sodium resonance radiation", *Applied Optics*, 28(13):2588–2591 (1989).

Kaufman et al., "Clinical Evaluation of Pulsed Erbium:YAG Laser Ablation in Cutaneous Surgery", (Abstract), *Partly Presented at 15th Annual Mtg of the American Society for LaserMedicine and Surgery*, (1995).

Kauver et al., "Laser Therapy for Cutaneous Vascular Lesions", *Operative Techniques in Otolaryngology—Head and Neck Surgery*, 5(4):250–258 (Dec. 1994).

Kienle et al., "Why do veins appear blue? A new look at an old question", *Applied Optics*, 35(7):1151–1160 (1996).

Lahaye et al., "Optimal laser parameters for port wine stain therapy: a theoretical approach", *Phys. Med. Biol.*, 30(6):573–587 (1985).

LaserSight Centers brochure, "Centauri.TM. Ophthalmic Erbium:Yag Laser", (Nov. 1993).

Lesinski et al., "Carbon Dioxide Lasers for Otosclerosis", *Otolaryngologic Clinics of North America*, 26(3)417–441 (Jun. 1993).

Lewis et al., "Backscattering target detection in a turbid medium by polarization discrimination", *Applied Optics*, 38(18):3937–3944 (Jun. 1999).

Lytle et al., "Improved Efficacy of SnET2 Mediated PDT With the Simultaneous Application of Selective Laser–Indused Hyperthermia", *SPIE Proceedings*, 2392–6:15–22.

Maloney et al., "Laser Otology", *Operative Techniques in Otolaryngology—Head and Neck Surgery*, 3(2):74–83 (Jun. 1992).

Milner et al., "Depth determination of chromophores in human skin by pulsed photothermal radiometry," *Applied Optics*, 35(19):3379–3385 (Jul. 1996).

Milner et al., "Depth profiling of laser–heated chromophores in biological tissues by pulsed photothermal radiometry", *Journal of the Optical Society of America A*, 12(7):1479–1488 (Jul. 1995).

Minamihaba et al., "Double–Level CU Inlaid Interconnects with Simultaneously Filled Viaplugs" *Japanese Journal of Applied Physics*, 35(2B):1107–1110 (Feb. 1996).

Mordon et al., "Relation Between Skin Surface Temperature and Minimal Blanching During Argon, Nd–YAG 532, and CW Dye 585 Laser Therapy of Port–Wine Stains," *Lasers in Surgery and Medicine*, 13(1):124–126 (1993).

Morreli et at., "Tunable Dye Lasers (577 nm) Treatment of Port Wine Stains", *Lasers Surg. Med.*, 6(1):94–99 (1986).

Orenberg et al., "Comparison of heat delivery systems for hyperthermia treatment of psoriasis", *Int. J. Hyperthermia*, 2(3):231–241 (1986).

Pai et al., "Selective Electroless Copper for FLSI Interconnection", *IEEE Electron Device Letters*, 10(9):423–425 (1989).

Patent Abstracts of Japan, vol. 012, No. 337 (E–657), Sep. 12, 1988 & JP 63 100749 A (Hitachi Ltd.), May 2, 1988.

Patent Abstracts of Japan, vol. 016, No. 263 (D–1216), Jun. 15, 1992 & JP 04 061125 A (Kanegafuchi Chem. Ind. Co. Ltd.), Feb. 27, 1992.

Patent Abstract of Japan, vol. 018, No. 480 (E–1603), Sep. 8, 1994 & JP 06 164140 A (Ibiden Co. Ltd.), Jun. 10, 1994.

Patent Abstracts of Japan, vol. 4, No. 172 (P–038), Sep. 9, 1980.

Petrovich et al., "Relationship of Response to Transurethral Hyperthermia and Prostate Volume in BPH Patients", *Urology*, 40(4):317–321 (Oct. 1992).

Polla, et al., "Tunable Pulsed Dye Laser for the Treatment of Benign Cutaneous Vascular Ectasia", *Drematologica*, 174:11–17 (1987).

Pomerantzeff et al., "A Method to Predetermine the Correct Photocoagulation Dosage", *Arch Ophthalmol*, 101:949–953 (1983).

Pomerantzeff et al., "Time and Location Analysis of Lesion Formation in Photocoagulation", *Arch Ophthalmol*, 101:954–957 (1983).

Sausville et al., "Blue Lamps in Phototherapy of Hyperbilrubinemia", *Journal of IES*, 112–118 (1972).

Semm et al., "Tissue Morcellation in Endoscopic Surgery", *Surgical Technology International V, International Developments In Surgery & Surgical Research*, 175–178. (1996).

Slatkine et al., "Instrumentation for Office Laser Surgery", *Operative Techniques in Otolaryngology—Head and Neck Surgery*, 5(4):211–217 (Dec. 1994).

Smith & Nephew, Inc., "Shaver Systems–Endoscopic Powered Instrument System", Mar. 1997.

Smith et al., "The Design of Optical Systems", *Modern Optical Engineering*, 273–278 (1990).

Smithies et al., "The Effect of the Illumination Time When Treating Port–wine Stains", *Lasers in Medical Science*, 10(2):93–104 (1995).

Taylor et al., "Light & Electron Microscopic Analysis of Tattoos Treated by O–Switched Ruby Laser", *J. of Investigative Dermatology*, 97:131–136 (1991).

Van–Gemert et al. "Treatment of Port–Wine Stains: Analysis", *Medical Instrumentation*, 21:213–217 (1987).

Waldow et al., "Nd: YAG Laser–Induced Hyperthermia in A Mouse Tumor Model", *Lasers in Surgery and Medicine*, 8(5)510–514 (1988).

Weinberg et al., "The Change in Light Reflection of the Retina During Therapeutic Laser–Photocoagulation," *IEEE J. Quantum Electronics*, QE–20(12):1481–1489 (1984).

Wright et al., "Initial in vivo results of hybrid retinal photocoagulation system", *Journal of Biomedical Optics*, 5(1):56–61 (Jan. 2000).

Yang et al., "Automatic Control of Lesion Size in a Simulated Model of the Eye", *IEEE Journal of Quantum Electronics*, 26(12):2232–2239 (1990).

Yang et al., "Reflectance as an Indirect Measurement of the Extent of Laser–Induced Coagulation," *IEEE Transactions on Biomedical Engineering*, 37(5):466–473 (1990).

Zee et al, "Whole–Body Hyperthermia in Cancer Therapy: A Report of A Phase I–II Study" *Eur. J., Cancer Clinical Oncology*, 19(9):1189–1200 (1983).

Zimmer information brochure, "Arthroscopic Blades and Burrs", (1996).

File history for EP0565331, Various Dates.

Deposition transcript of Lars Ake Morgan Gustavsson (Dec. 10, 2007).

*Lumenis Ltd., et al. v. Alma Ltd., et al.*, 07:CV3622, N.D.ILL.—Complaint (Jun. 28, 2007).

*Lumenis Ltd., et al. v. Alma Ltd., et al.*, 07:CV3622, N.D.ILL.—Joint Claim Construction Statement (Jan. 4, 2008.

*Lumenis Ltd., et al. v. Alma Ltd., et al.*, 07:CV3622, N.D.ILL.—Plaintiffs' Opening Claim Construction Brief) (Jan. 7, 2008).

*Lumenis Ltd., et al. v. Alma Ltd., et al.*, 07:CV3622, N.D.ILL.—Plaintiffs' Reply to Defendants Responsive Claim Construction Brief (Jan. 22, 2008).

*Lumenis Ltd., et al. v. Alma Ltd., et al.*, 07:CV3622, N.D.ILL.—Plaintiffs' Demonstratives for Markman Hearing (Jan. 23, 2008).

*Lumenis Ltd., et al. v. Alma Ltd., et al.*, 07:CV3622, N.D.ILL.—Defendants' Amended Answer, Affirmative Defenses, and Counterclaims (Jan. 25, 2008).

*Lumenis Ltd., et al. v. Alma Ltd., et al.*, 07:CV3622, N.D.ILL.—Plaintiffs' Reply to Defendants Counterclaim (Feb. 14, 2008).

*Lumenis Ltd., et al. v. Alma Ltd., et al.*, 07:CV3622, N.D.ILL.—Plaintiffs' Further Supplemental Answers to Defendants' First Set of Interrogatories to Plaintiffs (Nos. 3 an 11) (Feb. 1, 2008).

*Lumenis Ltd., et al. v. Alma Ltd., et al.*, 07:CV3622, N.D.ILL.—Plaintiffs' Rule 26(a)(1) Initial Disclosures to Defendants (Oct. 29, 2007).

*Lumenis Ltd., et al. v. Alma Ltd., et al.*, 07:CV3622, N.D.ILL.—Defendants Initial Disclosures Pursuant to Fed. R. Civ. P. 26(a) (Oct. 29, 2007).

*Lumenis Ltd., et al. v. Alma Ltd., et al.*, 07:CV3622, N.D.ILL.—Plaintiffs' Answers to Defendants' First Set of Interrogatories to Plaintiffs (Nov. 19, 2007).

*Lumenis Ltd., et al. v. Alma Ltd., et al.*, 07:CV3622, N.D.ILL.—Plaintiffs' Supplemental Answers to Defendants' First Set of Interrogatories to Plaintiffs (Nos. 2, 5, 8, & 15) (Dec. 14, 2007).

*Lumenis Ltd., et al. v. Alma Ltd., et al.*, 07:CV3622, N.D.ILL.—Plaintiffs' Further Supplemental Answers to Defendants' First Set of Interrogatories to Plaintiffs (Nos. 7, 11, and 12) (Dec. 21, 2007).

*Lumenis Ltd., et al. v. Alma Ltd., et al.*, 07:CV3622, N.D.ILL.—Plaintiffs' Further Supplemental Answers to Defendants' First Set of Interrogatories to Plaintiffs (No. 3) (Dec. 27, 2007).

*Lumenis Ltd., et al. v. Alma Ltd., et al.*, 07:CV3622, N.D.ILL.—Plaintiffs' Answers to Defendants' Second Set of Interrogatories to Plaintiffs (Nos. 16–18) (Dec. 28, 2007).

*Lumenis Ltd., et al. v. Alma Ltd., et al.*, 07:CV3622, N.D.ILL.—Plaintiffs' Supplemental Answers to Defendants' Second Set of Interrogatories to Plaintiffs (No. 18) (Jan. 14, 2008).

"Aesthetic CO2 Laser System", literature, 2 pages, (Aug. 1994).

"New Laser for Microlaryngeal Surgery", *I.L.. Med. Newsletter*, 1(1) (Spring 1991).

"The Er.YAG Laser System for ophthalmic microsurgery", *Aesculap Meditec brochure*, 2 pages, (Oct. 1994).

"The Proven Solution for Disk, Spinal Cord and Brain Microsurgery", *I. L. Med. Unilase product info. Brochure* (1993).

"The Proven Solution for Otologic and Microlaryngeal Surgery", *I. L. Med. Unilase product info. Brochure* (1993).

"Using a CO2 Laser During Conventional Microdiskectomy Shows Promise of Faster Recovery", *I.L. Med Newsletter*, 1(4) (Spring 1991).

"Control of Pulse Duration and Pulse Sequence Delays for Effective Photo–Epilation", *EpiLight™ Application Notes*, 3(2) (1997).

Adrian, "LightSheer™ 800 NM Pulsed. High–Power Diode Laser Hair Removal System", (2002).

Adrian, "Tissue Effects of a New Long Pulse Frequency Doubled 532 nm Neodymium: YAG Laser on Vascular Lesions", (2001).

Adrian, "Treatment of Facial Telangiectasia Using the VersaPulse® Variable Pulse Width Frequency Doubled Neodymium:YAG Laser: A Case Report", (2001).

Anderson et al., "Microvasculature Can Be Selectively Damaged Using Dye Lasers: A Basic Theory and Experimental Evidence in Human Skin", *Laser in Surgery and Medicine*, 1:263–276 (1981).

Anderson et al., "The Optics of Human Skin", *The Journal of Investigative Dermatology*, 77(1):13–19 (Jul. 1981).

Anderson, "Laser Hair Removal—A Lecture Presented to the 77th Congres of the Japan Society of Aesthetic Surgery", (Nov. 1999).

Bandel, "Effective Resolution of a Mature Port–Wine Stain Using PhotoDerm® VL", *Clinical Application Notes*, 1(2) (1998).

Bartley et al., "An Experimental Study to Compare Methods of Eyelash Ablation", *Ophthalmology*, 94(10):1286–1289 (Oct. 1987).

Battle et al., "Study of Very Long–Pulsed (100 ms) High–Powered Diode Laser for Hair Reduction on All Skin Types", (2002).

Beasley et al., "New Parameters for Intense Pulsed Light Rejuvenation With a Thermoelectrically Chilled Crystal Delivery System", *Cosmetic Dermatology*, 15(7):14–16 (Jul. 2002).

Bitter, "Noninvasive Rejuvenation of Photodamaged Skin Using Serial, Full–Face Intense Pulsed Light Treatments", *Dermatol Surg.*, 26(9):835–43 (Sep. 2000).

Campos et al., "Use of an 800 nm High–power Diode Laser for the Treatment of Leg Vein Telangiectasia", (2002).

Campos, "Safe and Effective Long–Term Hair Reduction in Tanned Patients Using an 800 nm Diode Laser", (2002).

Del Giglio, "Hair Removal Using a Combination of Electrical and Optical Energies—3–Month Clinical Study", 1–4, (Not Dated).

Del Giglio, "Hair Removal Using a combination of Electrical and Optical Energies: Multiple Treatments Clinical Study—Six–Month Follow Up", 1–4 (Not Dated).

Dierickx et al., "Effective, Permanent Hair Reduction Using a Pulsed, High–Power Diode Laser", (2002).

Dierickx, "Laser Hair Removal: Scientific Principles and Practical Aspects", (2002).

Dover et al., "Pigmented Guinea Pig Skin Irradiated With Q–Switched Ruby Laser Pulses", *Arch Dermatol*, 125(1):43–44 (Jan. 1989).

Dréno et al., "The Benefit of Chilling in Argon–Laser Treatment of Port–Wine Stains", *Plast Reconstr Surg.*, 75(1):42–45 (Jan. 1985).

Dzubow, "Leg Veins and Stretch Marks—Have They Seen the Light?", *Dermatol Surg.*, 22(4):321 (Apr. 1996).

Eckhouse et al., "The Application of Selective Photothermolysis in Treating Leg Veins and Other Benign Vascular Lesions", (Apr. 1996).

ESC Medical Systems, "Eliminating Multicolored Tattoos with PhotoDerm® PL", *PhotoDerm® PL Application Notes*, 2(2) (1997).

ESC Medical Systems, "Facial and truncal angiomas—treating patients quickly and effectively", *PhotoDerm® Application Notes*, 1(2) (1996).

ESC Medical Systems, "How does it look in theory?", (1996).

ESC Medical Systems, "Significance of Wavelength Range for Effective Hair Photo–Epilation", *EpiLight Hair Removal System Application Notes*, 3(1) (1997).

ESC Medical Systems, "Superior Treatment of Benign Pigmented Lesions with PhotoDerm® PL", *PhotoDerm® PL Application Notes*, 2(1) (1997).

ESC Medical Systems, "Why are leg veins so difficult to treat?", *PhotoDerm® VL Application Notes*, 1(1) (1996).

Gilchrest et al., "Chilling Port Wine Stains Improves the Response to Argon Laser Therapy", *Plast Reconstr Surg.*, 69(2):278–83 (Feb. 1982).

Gold et al., "Intense Pulsed Light (IPL™) System Enables Successful Treatment of Skin Type VI", *Clinical Application Notes*, 2(5) (2000).

Gold et al., "Long–term epilation using the EpiLight broad band, intense pulsed light hair removal system", *Dermatol Surg.*, 23(10):909–913 (Oct. 1997).

Gold, "Treatment of Larger and Deeper Varicosities Utilizing a 1064 nm Laser System", *Cosmetic Dermatology*, (Nov. 2000).

Goldman, "Effects of New Laser Systems o the Skin" *Arch. Dermatol.*, 108:385–390 (Sep. 1973).

Goldman et al., "Impact of the Laser on Nevi and Melanomas", *Arch Dermatol*, 90:71–75 (Jul. 1964).

Goldman et al., "Laser Treatment of Tattoos—A Preliminary Survey of Three Year's Clinical Experience", *JAMA*, 201(11):163–166 (Sep. 1967).

Goldman et al., "Long–Term Laser Exposure of a Senile Freckle", *Arch. Environ. Health*, 22:401–403 (Mar. 1971).

Goldman et al., "Pathology of the Effect of the Laser Beam on the Skin", *Nature*, 197:912–914 (Mar. 1963).

Goldman et al., "Photothermal Sclerosis of Leg Veins", *Dermatol Surg.*, 22(4):323–30 (Apr. 1996).

Goldman et al., "Preliminary Investigation of Fat Embolization from Pulsed Ruby Laser Impacts of Bone", *Nature*, 221:361–363 (Jan. 1969).

Goldman et al., "Radiation from a Q–Switched Ruby Laser, Effect of Repeated Impacts of Power Output of 10 Megawatts on a Tattoo of Man", *The Journal of Investigative Dermatology*, 44:69–71 (Jan. 1965).

Goldman et al., "Replica Microscopy and Scanning Electron Microscopy of Laser Impacts on the Skin", *The Journal of Investigative Dermatology*, 52(1):18–24 (Jan. 1969).

Goldman et al., "The Biomedical Aspects of Lasers", *JAMA*, 188(3):230–234 (Apr. 1964).

Goldman et al., "The Effect of Repeated Exposures to Laser Beams", *Acta derm.–venereol*, 44:264–268 (1964).

Goldman et al., "Treating Varicose and Telangiectatic Leg Veins", *Federal Practitioner*, (Mar. 1997).

Goldman et al., "Treatment of Basal Cell Epithelioma by Laser Radiation", *JAMA*, 189:773–5 (Sep. 1964).

Goldman, "Dermatologic manifestations of laser radiation", S92–S93 (Not Dated).

Goldman, "Laser Surgery for Skin Cancer", *New York State Journal of Medicine*, (Oct. 1977).

Goldman, "One Laser For A Cosmetic Dermatologic Practice", *Cosmetic Dermatology*, 15(7):49–50 (Jul. 2002).

Goldman, "Surgery by Laser for Malignant Melanoma", *J. Dermatol. Surg. Oncol.*, 5(2) (Feb. 1979).

Goldman, "The Skin", *Arch Environ Health*, 18:434–436 (Mar. 1969).

Herloski et al., "Gaussian beam ray–equivalent modeling and optical design", *Applied Optics*, 22(8):1168–1174 (Apr. 1983).

Huang et al., "Intense Pulsed Light for the Treatment of Facial Freckles in Asian Skin", *Dermatol Surg.*, 29(11):1008–1012 (Nov. 2002).

Hunt et al., "Treatment of Large Body Areas with EpiLight® Hair Removal System: Multi–Center Back Epilation", *Clinical Application Notes*, 2(2):1–4 (1998).

Inderfurth et al., "Dynamic Reflectometer for Control of Laser Photocoagulation on the Retina", *Lasers in Surgery and Medicine*, 15(1):54–61 (May 1994).

Jay, "Photo–Epilation with the EpiLight™ Hair Removal System: Multi–case Study", *Clinical Application Notes*, 2(3) (1998).

Johnson et al., "Intense pulsed light treatment of hirsutism: case reports of skin phototypes V and VI", *Journal of Cutaneous Laser Therapy*, 1:233–237 (1999).

Karpen, "Treating Benign Vascular Lesions of the Lower Extremities: Past, Present, and Future", *Journal of Clinical Laser Medicine & Surgery*, 12(2):111–112 (1994).

Kautz et al., "Early Intervention in Pediatric Hemangiomas with the VascuLight™ Intense Pulsed Ligh / Laser Source", *Clinical Application Notes*, 8(4) (2000).

Kazmi, "Laser Hair Removal with an 800nm Diode Laser—A Retrospective Study of 1000 Women with Skin Types II to VI", (Jun. 2002).

Klavuhn, "Coverage Rate: The Influence of Laser Parameters on Treatment Time", *Laser Hair Removal Note No. 3*, (Mar. 2000).

Klavuhn, "Epidermal Protection: A Comparative Analysis of Sapphire Contact and Cryogen Spray Cooling", *Laser Hair Removal Technical Note No. 1*, (Jan. 2000).

Klavuhn, "Illumination Geometry: The Importance of Laser Beam Spatial Characteristics", *Laser Hair Removal Technical Note No. 2*, (Feb. 2000).

Kono et al., "Diode Laser–Assisted Hair Removal in Asians: A Study of 101 Japanese Patients", (2000).

Kreindel et al., "Electro–Optical Synergy (ELOS™) Technology for Aesthetic Medicine—Light Triggering Effect on RF Selectivity", 1–4, (Not Dated).

Kreindel et al., "Electro–Optical Synergy ELOS™) Technology for Aesthetic Medicine Advantages and limitations of various forms of electromagnetic energy for safe and effective hair removal", 1–4 (Not Dated).

Kuriloff et al., "Pharyngoesophageal hair growth: The role of laser epilation", *Otolaryngol Head Neck Surg.*, 98(4):342–5 (Apr. 1988).

Lask et al., "The role of laser and intense light sources in photo–epilation: a comparative evaluation", *Journal of Cutaneous Laser Therapy*, 1:3–13 (1999).

Laughlin, "Effective Epilation of a white hair using combined radio–frequency and optical energy", (Not Dated).

Laughlin, "Epilation in dark skin (types V and VI) with integrated radio–frequency and optical energy", 23–26 (Not Dated).

Levy, "Intense pulsed light treatment for chronic facial erythema of systemic lupus erythematosus: a case report", *Journal of Cutaneous Laser Therapy*, 2(4):195–198 (Dec. 2000).

Lou et al., "Prospective Study of Hair Reduction by Diode Laser (800nm) with Long–Term Follow–Up", *Dermatol Surg.*, 26(5):428–432 (May 2000).

Lumenis Inc., "IPL Skin Treatments using Photorejuvenation: helps restore the skin's youthful look", (2002).

Lumenis Inc., "VascuLight: Intense Pulsed Light and Laser Technology", (2002).

Lumenis Inc. "VascuLight Elite: Intense Pulsed Light and Laser Technology", (2002).

Mccoy et al., "An Evaluation of the Copper–Bromide Laser for Treating Telangiectasia", *Dermatol. Surg.*, 22:551–557 (1996).

Moraga, "European Multi–Center Study: VascuLight® for the Treatment of Varicose Veins and Leg Telangiectasias, as well as Other Vascular Lesions", *Clinical Application Notes*, 8(1) (2001).

Moretti, "IPL Photorejuvenation Popularity Spreads Rapidly", *Aesthetic Buyers Guide*, (Mar. 2001).

Moretti, "Laser–Based Technology Expands Treatment Options", *Medical Laser Insight*, (Apr. 1997).

Negishi et al., "Full–Face Photorejuvenation of Photodamged Skin by Intense Pulsed Light with Integrated Contact Cooling: Initial Experiences in Asian Patients", *Lasers in Surgery and Medicine*, 30(4):298–305 (2002).

Negishi et al., "Photorejuvenation for Asian Skin by Intense Pulsed Light", *Dermatol Surg*, 27:7:627–32 (Jul. 2001).

Nestor et al., "Photorejuvention Non–Ablative Skin Rejuvenation Using Intense Pulse Light" (Not dated).

Pardo et al., "Use of the LightSheer™ Diode Laser System for Hair Reduction: Safety and Efficacy in a Large Series of Treatments", (Feb. 2001).

Parrish et al., "Selective Thermal Effects with Pulsed Irradiation from Lasers: From Organ to Organelle", *The Journal of Investigative Dermatology*, 80(6):75s–80s (Jun. 1963).

Pervaiz et al., "A New Method of Quantitating Damage to the Hair Shaft: Its Application to Ultraviolet– and Radio Frequency–Treated Hair", *Annals New York Academy of Sciences*, 642:491–2 (Dec. 1991).

Polla et al., "Melanosomes Are a Primary Target of Q–Switched Ruby Laser Irradiation in Guinae Pig Skin", *The Journal of Investigative Dermatology*, 89(3):281–6 (Sep. 1987).

Raulin et al., "Treatment of a Nonresponding Port–Wine Stain With a New Pulsed Light Source (PhotoDerm® VL)", *Lasers Surg Med.*, 21(2):203–8 (1997).

Raulin et al., "Effective Treatment of Hypertrichosis with Pulsed Light: A Report of Two Cases", *Annals of Plastic Surgery*, 39(2):169–173 (Aug. 1997).

Raulin et al., "Photoderm VL®—efficiency and limitations of an intense pulsed light source", *Australasian Journal of Dermatology*, 38(2) (Jun. 1997) (Abstract Only).

Raulin et al., "Treatment of Adult Port–Wine Stains Using Intense Pulsed Light Therapy (PhotoDerm® VL): Brief Initial Clinical Report", *Dermatol Surg*, 23(7):594–7 (Jul. 1997).

Raulin et al., "Treatment of benign venous malformation with an intense pulsed source (PhotDerm® VL)", Europena Journal of Dermatology 7(4):279–285 (Jun. 1997).

Riggle et al., "Laser Effects on Normal and Tumor Tissue", 35–63 (Not Dated).

Sadick et al., "Advances in Laser Surgery for Leg Veins: Bimodal Wavelength Approach to Lower Extremity Vessels, New Cooling Techniques, and Longer Pulse Durations", *Dermatol Surg.*, 28:1:16–20 (Jan. 2002).

Sadick et al., "Long–term Photoepilation Using a Broad–spectrum Intense Pulsed Light Source", *Arch Dermatol*, 136:1336–1340 (Nov. 2000).

Sadick, "A dual wavelength approach for laser/intense pulsed light source treatment of lower extremity veins", *J Am Acad Dermatol*, 46(1):66–72 (Jan. 2002).

Sadick, "The Role of Combined Intense Pulsed Light/Radiofrequency Technology in the Management of Blond and White Hair Photoepilation", (Feb. 8, 2003, ISHR, Aspen, Colorado).

Schroeter et al., "An Intense Light Source", *Dermatol Surg.*, 24:743–748 (1998).

Schroeter et al., "Clinical significance of an intense, pulsed light source on leg telangiectasias of up to 1 mm diameter", *Eur J Dermatol*, 7:38–42 (Jan.–Feb. 1997).

Shimbashi et al., "Ruby Laser Treatment of Pigmented Skin Lesions", *Aesth. Plast. Surg.*, 19(3):225–9 (1995).

Svaasand et al., "On the physical rationale of laser induced hyperthermia", 65–81 (Not Dated).

Taylor et al., "Treatment of Tattoos by Q–Switched Ruby Laser", *Arch Dermatol*, 126(7): 893–9 (Jul. 1990).

Troxler, "One Clinic's Experience in the Treatment of Varicose Veins and Leg Telangiectasias with the VascuLight™ Intense Pulsed Light / Nd:YAG Laser Source", *Clinical Application Notes*, 8(3) (2001).

Waldman et al., "Cutaneous inflammation: Effects of hydroxy acids and eicosand inhibitors on vascular permeability", *The Journal of Investigative Dermatology*, 88:523 (1987) (Abstract Only).

Warren, "Pigmentation induction by melanocyte stimulating hormone in human skin culture", *The Journal of Investigative Dermatology*, 88:523 (1987) (Abstract Only).

Wastek et al., "Characterization of $^3$H–substance P (SP) binding to a mouse monoclonal mast cell line", *The Journal of Investigative Dermatology*, 88:523 (1987) (Abstract Only).

Watanabe et al., "The effect of pulse duration on selective pigmented cell injury by dye lasers", *The Journal of Investigative Dermatology*, 88:523 (1987) Abstract Only).

Weir et al., "Photo–assisted epilation—review and personal observations", *Journal of Cutaneous Laser Therapy*, 1:135–143 (1999).

Weiss et al., "Intense pulsed light: newer perspective", *Dermatol. Surg.*, 23(10):941–945 (1997).

Weiss et al., "New Treatment for Telangiecases and Venulectases: Status of Intense Pulsed Light Therapy", (Not Dated).

Weiss et al., "Sclerotherapy in the U.S.", *Dermatol. Surg.*, 21:393–396 (1995).

Weissman et al., "Growth, collogen and glycosaminoglycan synthesis by dermal fribroblasts derived from puva treated and psoriatic patients", *The Journal of Investigative Dermatology*, 88:523 (1987) (Abstract Only).

Welsh et al., "Evaluation of Cooling Techniques for the Protection of the Epidermis During ND–YAG Laser Irradiation of the Skin", *Neodymium–YAG Laser in Medicine and Surgery*, (1983).

Werner et al., "New possibilities of epilation with a high energy flash lamp", (Not Dated).

Wertz et al., "Effects of essential fatty acid deficiency on the structure and function of epidermal lipids", *The Journal of Investigative Dermatology*, 88:523 (1987) (Abstract Only).

Wheeland, "Laser–Assisted Hair Removal", *Dermatol Clin.*, 15(3):469–477 (Jul. 1997).

Woo, "Using EpiLight® for Hair Removal Treatment of Fitzpatrick Skin Types IV and V", *Clinical Application Notes*, 2(3):1–4 (1998).

Yanai et al., "Argon Laser Therapy of Port–Wine Stains: Effects and Limitations", *Plastic and Reconstructive Surgery*, 75(4):520–525 (Apr. 1985).

Yules et al., "The Effect of Q–Switched Ruby Laser Radiation on Demal Tattoo Pigment in Man", *Arch Surg*, 95 (Aug. 1967).

Zeitler et al., "Laser Characteristics that Might be Useful in Biology", Chapter 1, 1–18 (Not Dated).

Zelickson et al., "EpiLight® Treatment of Hair Removal Using the Circulating Cutaneous Cooling Device: Preliminary Study Report" (Not Dated).

Goldman et al., "Effect of the Laser Beam on the Skin", *The Journal of Investigative Dermotology*, 40:121–122 (Mar. 1963).

Westinghouse Engineer, "Special Blue Lamp Helps Treat Jaundice in Newborn Infants", 31(1) (Jan. 1971).

*Lumenis Ltd., et al. v. Syneron Medical Ltd., et al.*, 2:02–cv–08269–ABC–PLA, C.D. CA.—Syneron Inc.'s Answer to Plaintiffs' Complaint (Nov. 19, 2002).

*Lumenis Ltd., et al. v. Syneron Medical Ltd., et al.*, 2:02–cv–08269–ABC–PLA, C.D. CA.—Syneron Medical Ltd.'s Answer to Plaintiffs' Complaint (Dec. 9, 2002).

*Lumenis Ltd., et al. v. Syneron Medical Ltd., et al.*, 2:02–cv–08269–ABC–PLA, C.D. CA.—Appendix of Dictionary References in Support of Plaintiffs' Report to Court–Appointed Expert (Jan. 9, 2003).

*Lumenis Ltd., et al. v. Syneron Medical Ltd., et al.*, 2:02–cv–08269–ABC–PLA, C.D. CA.—Syneron's Appendix of Prior Art References Discussed in Declaration of Dr. Warren S. Grundfest (May 8, 2003).

*Lumenis Ltd., et al. v. Syneron Medical Ltd., et al.*, 2:02–cv–08269–ABC–PLA, C.D. CA.—Plaintiffs' Report to Court–Appointed Expert Dr. Bahram (Dec. 30, 2002).

*Lumenis Ltd., et al. v. Syneron Medical Ltd., et al.*, 2:02–cv–08269–ABC–PLA, C.D. CA.—Complaint for Patent Infringement (Oct. 30, 2002).

*Lumenis Ltd., et al. v. Syneron Medical Ltd., et al.*, 2:02–cv–08269–ABC–PLA, C.D. CA.—Declaration of Alon Maor in Support of Plaintiffs' Motion for Prelimiary Injunction (Apr. 25, 2003).

*Lumenis Ltd., et al. v. Syneron Medical Ltd., et al.*, 2:02–cv–08269–ABC–PLA, C.D. CA.—Declaration of Alon Maor in Support of Plaintiffs' Ex Parte Application for Temporary Retraining Order and Order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Declaration of Benjamin J. Fox in Opposition to Plaintiffs' Motion for a Preliminary Injunction (May 8, 2003).

*Lumenis Ltd., et al. v. Syneron Medical Ltd., et al.*, 2:02–cv–08269–ABC–PLA, C.D. CA.—Declaration of Domenic Serafino Re: Plaintiffs' Motion for Preliminary Injunction and Posting of Bond (Jul. 25, 2003).

*Lumenis Ltd., et al. v. Syneron Medical Ltd., et al.*, 2:02–cv–08269–ABC–PLA, C.D. CA.—Declaration of Dr. Michael Kreindel in Opposition to Motion for Preliminary Injunction (May 8, 2003).

*Lumenis Ltd., et al. v. Syneron Medical Ltd., et al.*, 2:02–cv–08269–ABC–PLA, C.D. CA.—Declaration of Dr. Warren S. Grundfest in Support of Syneron's Opposition to Plaintiffs' Motion for Preliminary Injunction (May 8, 2003).

*Lumenis Ltd., et al. v. Syneron Medical Ltd., et al.*, 2:02–cv–08269–ABC–PLA, C.D. CA.—Declaration of Felix T. Woo in Support of Plaintoffs' Motion for Preliminary Injunction (May 20, 2003).

*Lumenis Ltd., et al. v. Syneron Medical Ltd., et al.*, 2:02–cv–08269–ABC–PLA, C.D. CA.—Declaration of Felix T. Woo in Support of Plaintiffs Ex Parte Application for Temporary Restraining Order and order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Declaration of Harry F. Manbeck, Jr. in Response to Expert Report of Gerald J. Mossinghoff (May 27, 2003).

*Lumenis Ltd., et al. v. Syneron Medical Ltd., et al.*, 2:02–cv–08269–ABC–PLA, C.D. CA.—Declaration of John M. May in Support of Opposition to Plaintiffs' Ex Parte Application for Temporary Restraining Order and Order to Show Causes Regarding Preliminary Injunction (Nov. 1, 2002).

*Lumenis Ltd., et al. v. Syneron Medical Ltd., et al.*, 2:02–cv–08269–ABC–PLA, C.D. CA.—Declaration of Jordan A. Sigale in Support of Lumenis' Response to Syneron's Objections to Lumenis' Proposed Order Re: Preliminary Injunction and Posting of Bond (Jul. 31, 2003).

*Lumenis Ltd., et al. v. Syneron Medical Ltd., et al.*, 2:02–cv–08269–ABC–PLA, C.D. CA.—Declaration of Laura A. Wytsma in support of Plaintiffs' Ex Parte Application for Temporary Restraining Order and order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Declaration of Moshe Mizrahy in Opposition to Plaintiffs' Motion for a Preliminary Injunction (May 8, 2003).

*Lumenis Ltd., et al. v. Syneron Medical Ltd., et al.*, 2:02–cv–08269–ABC–PLA, C.D. CA.—Declaration of Moshe Mizrahy in support of Opposition to Plaintiffs Ex Parte Application for Temporary Restraining Order and Order to Show Cause Re Preliminary Injunction (Nov. 1, 2002).

*Lumenis Ltd., et al. v. Syneron Medical Ltd., et al.*, 2:02–cv–08269–ABC–PLA, C.D. CA.—Declaration of Robert Anderson in Support of Plaintiffs' Ex Parte Application for Temporary Restraining order and Order to show Cause re Preliminary Injunction (Nov. 1, 2002).

*Lumenis Ltd., et al. v. Syneron Medical Ltd., et al.*, 2:02–cv–08269–ABC–PLA, C.D. CA.—Declaration of Sarit Mousssayoff in Support of Plaintiffs' Motion for Preliminary Injunction (May 20, 2003).

*Lumenis Ltd., et al. v. Syneron Medical Ltd., et al.*, 2:02–cv–08269–ABC–PLA, C.D. CA.—Declaration of Shimon Eckhouse in Support of Opposition to Plaintiffs' Ex Parte Application for Temporary Restraining Order to Show Cause Re Preliminary Injuction (Nov. 1, 2002).

*Lumenis Ltd., et al. v. Syneron Medical Ltd., et al.*, 2:02–cv–08269–ABC–PLA, C.D. CA.—Plaintiff Lumenis Ltd. And Lumenis Inc.'s Ex Parte Application for Temporary Restraining Order to Show Cause Re Preliminary Injunction; Memorandum of Points and Authorities; Declarations of Alon Maor, Robert Anderson and Felix T. Woo; [Proposed] Order (Oct. 28, 2000).

*Lumenis Ltd., et al. v. Syneron Medical Ltd., et al.*, 2:02–cv–08269–ABC–PLA, C.D. CA.—Expert Report of Hon. Gerald J. Mossinghoff in support of Plaintiffs' Motion for Preliminary Injunction (May 20, 2003).

*Lumenis Ltd., et al. v. Syneron Medical Ltd., et al.*, 2:02–cv–08269–ABC–PLA, C.D. CA.—Syneron Medical Ltd.'s First Amended Answer to Plaintiffs' Complaint (Apr. 23, 2003).

*Lumenis Ltd., et al. v. Syneron Medical Ltd., et al.*, 2:02–cv–08269–ABC–PLA, C.D. CA.—Syneron Inc.'s First Amended Answer to Plaintiffs' Complaint (Apr. 23, 2003).

*Lumenis Ltd., et al. v. Syneron Medical Ltd., et al.*, 2:02–cv–08269–ABC–PLA, C.D. CA.—Plaintiffs' Memorandum of Points and Authorities in Support of Motion for Preliminary Injunction (Apr. 25, 2003).

*Lumenis Ltd., et al. v. Syneron Medical Ltd., et al.*, 2:02–cv–08269–ABC–PLA, C.D. CA.—Synerons' Memorandum of Points and Authorities in Opposition to Plaintiffs' Motion for a Preliminary Injunction (May 8, 2003).

*Lumenis Ltd., et al. v. Syneron Medical Ltd., et al.*, 2:02–cv–08269–ABC–PLA, C.D. CA.—Plaintiffs' Ex Parte Application for Temporary Restraining Order and Order to Show Cause Re Preliminary Injunction (Nov. 4, 2002).

*Lumenis Ltd., et al. v. Syneron Medical Ltd., et al.*, 2:02–cv–08269–ABC–PLA, C.D. CA.—Notice of Errata Re Plaintiffs' Ex Parte Application for Temporary Restraining Order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Notice of Errata (Jan. 8, 2003).

*Lumenis Ltd., et al. v. Syneron Medical Ltd., et al.*, 2:02–cv–08269–ABC–PLA, C.D. CA.—Plaintiff's Notice of Lodging Opinion and Tutorial of Court Appointed Expert Dr. Oscar M. Stafsudd (Apr. 25, 2003).

*Lumenis Ltd., et al. v. Syneron Medical Ltd., et al.*, 2:02–cv–08269–ABC–PLA, C.D. CA.—Notice of Response of Court Appointed Expert to Order Seeking Clarification (Jun. 16, 2003).

*Lumenis Ltd., et al. v. Syneron Medical Ltd., et al.*, 2:02–cv–08269–ABC–PLA, C.D. CA.—Syneron Inc.'s Objection to Declaration of Robert Anderson Submitted in Support of Plaintiffs' Ex Parte Application for Temporary Restraining order and Order to Show Cause Re Preliminary Injunction (Nov. 1, 2002).

*Lumenis Ltd., et al. v. Syneron Medical Ltd., et al.*, 2:02–cv–08269–ABC–PLA, C.D. CA.—Defendant Syneron, Inc.'s Opposition to Plaintiffs' Ex Parte Application for Temporary Restraing Order and Order to Show Cause Re Preliminary Injunction (Nov. 1, 2002).

*Lumenis Ltd., et al. v. Syneron Medical Ltd., et al.*, 2:02–cv–08269–ABC–PLA, C.D. CA.—Plaintiffs' Motion for Preliminary Injunction (Jul. 11, 2003).

*Lumenis Ltd., et al. v. Syneron Medical Ltd., et al.*, 2:02–cv–08269–ABC–PLA, C.D. CA.—Plaintiffs' Motion for Preliminary Injunction (Aug. 5, 2003).

*Lumenis Ltd., et al. v. Syneron Medical Ltd., et al.*, 2:02–cv–08269–ABC–PLA, C.D. CA.—Reply of Plaintiffs Lumenis Ltd. And Lumenis Inc. in Support of Motion for Preliminary Injunction (May 22, 2003).

*Lumenis Ltd., et al. v. Syneron Medical Ltd., et al.*, 2:02–cv–08269–ABC–PLA, C.D. CA.—Reply Opinion of Joseph T. Walsh, Jr. in support of Plaintiffs' Motion for Preliminary Injunction (May 20, 2003).

*Lumenis Ltd., et al. v. Syneron Medical Ltd., et al.*, 2:02–cv–08269–ABC–PLA, C.D. CA.—Syneron's Response Brief for Court–Appointed Expert Re: Claim Construction (Jan. 17, 2003).

*Lumenis Ltd., et al. v. Syneron Medical Ltd., et al.*, 2:02–cv–08269–ABC–PLA, C.D. CA.—Plaintiffs' Response Brief to Court–Appointed Expert (Jan. 9, 2003).

*Lumenis Ltd., et al. v. Syneron Medical Ltd., et al.*, 2:02–cv–08269–ABC–PLA, C.D. CA.—Submission of Materials for Court Appointed Expert Pursuant to the Parties' Joint Stipulation (Dec. 19, 2002).

*Lumenis Ltd., et al. v. Syneron Medical Ltd., et al.*, 2:02–cv–08269–ABC–PLA, C.D. CA.—Supplemental Declaration Of Alon Moar in Support of Plaintiff Lumenis, Inc.'s Motion for Preliminary Injunction (May 23, 2003).

*Lumenis Ltd., et al. v. Syneron Medical Ltd., et al.*, 2:02–cv–08269–ABC–PLA, C.D. CA.—Supplemental Declaration of Felix T. Woo in Support of Plaintiffs' Ex Parte Application for Temporary Restraining Order and Order to Show Cause Re Preliminary Injunction (Nov. 4, 2002).

*Lumenis Ltd., et al. v. Syneron Medical Ltd., et al.*, 2:02–cv–08269–ABC–PLA, C.D. CA.—Plaintiffs' Disclosures Persuant to Fed.R.Civ.P.26 (Jan. 14, 2003).

*Lumenis Ltd., et al. v. Syneron Medical Ltd., et al.*, 2:02–cv–08269–ABC–PLA, C.D. CA.—Plaintiffs' Response to Synerons' First Set of Interrogatories (Jan. 13, 2003).

*Lumenis Ltd., et al. v. Alma Ltd., et al.*, 07:CV3622, N.D.ILL.—Videotaped Deposition of Richard R. Anderson, M.D. (Dec. 13, 2007).

Aculight HR, *Operator Manual*, PB 3581110 Revision B (Jul. 2001).

AestiLight™ Millennium, *Operator Manual*, PB 3381110 Revision A (Aug. 2003).

AestiLight™ Photo Epilation System, *AestiLight Service Manual*, PB 3380120 Revision B (Mar. 2000).

AestiLight™ Photo Epilation System, *Operator Manual*, PB 3380110 Revision A (May 1999).

EpiLight® Hair Removal System, *Operator Manual*, PB 400–9001 Revision 9 (Aug. 2000).
EpiLight™ Hair Removal System, *Operator Manual*, PB 400–9001 Revision 2 (Jul. 1996).
EpiLight™ Hair Removal System, Operator Manual, PB 400–9001 Revision 5 (Aug. 1997).
EpiLight™ Hair Removal System, Operator Manual, PB 400–9001 Revision 2 (Jul. 1996).
EpiLight™ Hair Removal System, Operator Manual, PB 400–9001 Revision 4 (Jul. 1997).
EpiLight™ Hair Removal System, Operator Manual, PB400–9001 Revision 1 (Jun. 1996).
EpiLight™ Hair Removal System, Operator's Manual, PB 400–9001 Revision 7 (Jan. 1998).
EpiLight™ Hair Removal System, Operator's Manual, PB 400–9001 Revision 6 (Dec. 1997).
EpiLight™ Hair Removal, Operator Manual, PB 400–9001 Revision 3 (Feb. 1997).
IPL Quantum HR, Operator's Manual, PB 3580110 Revision B (Jun. 2001).
IPL Quantum SR, Operator's Manual, PB 3680110 Revision A (Sep. 2000).
IPL™ Quantum DL, Operator's Manual, PB 3780110 Revision B (Jul. 2002).
IPL™ Quantum HR, Operator's Manual, PB 3580110 Revision D, (Jul. 2002).
IPL™ Quantum HR, Operator's Manual, PB 3580100 Revision C (Dec. 2001).
IPL™ Quantum SR, Operator Manual, PB 3680110 Revision D (Oct. 2002).
Lumenis IPL™ Quantum, *Service Manual*, (Mar. 2002).
PhotoDerm®, *Operator Manual*, PB 200–9001 Revision 1 (Jun. 1996).
PhotoDerm PL, *Operator Manual*, PB 200–9012 Revision A (May 1997).
PhotoDerm VL, *Operator Manual*, PB 100–9033 Revision A (May 1997).
PhotoDerm® VL *Operator Manual*, (Jul. 1997).
PhotoDerm® VL, *Operator Manual*, PB 100–9001 Revision 2B (Oct. 1995).
PhotoDerm® VL, *Operator Manual*, PB 100–9001–1 Revision 1 (Apr. 1995).
PhotoDerm® VL/PL, *Operator's Manual*, PB 2180150 Revision B (May 1998).
PhotoDerm® VL/PL, *Service Manual*, PB 100–9022 Revision 2 (Nov. 1996).
PhotoDerm® VL/PL/HR, *Operator Manual*, PB 2280150 Revision B (May 1998).
TwoHead PhotoDerm®, *Service Manual*, (Apr. 2000).
VascuLight EPI Mode, *Operating Instructions*, PB 2300410 Revision C (Dec. 2001).
VascuLight™ Elite, *Operator's Manual*, PB 2780110 Revision A (Oct. 2002).
VascuLight™, *Operator Manual*, PB 2380150 Revision B (2001).
Epilight® Hair Removal System, *Service Manual*, PB4009007 Revision B (Jan. 1999).
Aculight™ *Operator's Manual*, PB3581110 Revision 0 (Feb. 2001).
IPL Quantum HR, *Operator Manual*, PB3580110 Revision A (Jun. 2000).
Epilight® Hair Removal System, *Operator Manual*, PB 4009001Revision (Nov. 1998).

ESC Medical, "New Photo–Epilation Technique for Hair Removal", *Medco Forum*, 4(13) (Sep. 1997).
Reliant Technologies, Inc. Product News,,Accu–Scan, Multi–Wavelength Laser Scanning System for CO2, Jan. 25, 1995, 3 pages.
Sharplan Swiftlase Flashscan, Jun. 1993.
Unilase A new CO2 Laser for Microsurgery, I.L. Med. Newsletter, vol. 1, No. 3, Spring 1991.
I. L. Med. Unilase System Brochure (1993).
Goldman, *Biomedical Aspects of the Laser—An Introduction of Laser Applications Into Biology and Medicine*, chapters 1, 2, 23 and index (1967).
Gossman et al., "Experimental Comparison of Laser and Cryosurgical Cilia Destruction", *Ophthalmic Surgery*, 23(3):179–182 (Mar. 1992).
Gossman et al., "Prospective Evaluation of the Argon Laser in the Treatment of Trichiasis", *Ophthalmic Surgery*, 23(3):183–187 (Mar. 1992).
"The Spectrum RD–1200 Q–Switched Ruby Laser", (Not Dated).
ESC Medical Systems, "Control of Pulse Duration and Pulse Secuence Delays for Effective Photo–Epilation", *EpiLight Hair Removal System Application Notes*, 3(2) (1997).
Geronemus, "Laser and Pulsed Light Source Treatment of Leg Vessels", (Sep. 1995).
Goldman, "Effects of New Laser Systems on the Skin", *Arch Dermatol*, 108(3):385–90 (Sep. 1973).
Goldman, "Treating Varicose and Telangiectatic Leg Veins", *Federal Practitioner* (Mar. 1997).
Kincade, "New Procedures push tissue studies beneath the surface", *Laser Focus World*, pp. 57–63, (Aug. 1995).
Achauer et al., "Argon Laser Treatment of Telangiectasia of the Face and Neck: 5 Years' Experience", *Lasers Surg. Med.*, 7:495–498 (1987).
Alora et al., "Recent Developments in Cutaneous Lasers", *Lasers Surg. Med.*, 26:108–118 (2000).
Alster et al., "Treatment of Port–Wine Stains with the Flashlamp–pumped Pulsed Dye Laser: Extended Clinical Experience in Children and Adults", *Ann. Plast. Surg.*, 32(5):478–484 (1994).
Altshuler et al., "Extended Theory of Selective Photothermolysis",*Lasers Surg. Med.*, 29:416–432 (2001).
Ambrose et al., "Prospective randomized comparison of photocoagulation and rubber band ligation in treatment of haemorrhoids", *Br. Med. J.*, 286:1389–1391 (1983).
Anderson et al., "Mechanisms of Selective Vascular Changes Caused by Dye Lasers",*Lasers Surg. Med.*, 3:211–215 (1983).
Anderson et al., "Selective Photothermolysis: Precise Microsurgery by Selective Absorption of Pulsed Radiation", *Science*, 220:524–527 (1983).
Anderson, T.F., "Light Sources in Photomedicine", in *Clinical Photomedicine*, Chapter 3, pp. 37–58, Marcel Dekker, Inc., New York (1993).
Angermeier, M.C., "Treatment of facial vascular lesions with intense pulsed light", *J. Cutan. Laser Ther.*, 1:95–100 (1999).
Anvari et al., "Selective cooling of biological tissues: application for thermally mediated therapeutic procedures", *Phys. Med. Biol.*, 40:241–252 (1995).
Apfelberg et al., "Comparison of Argon and Carbon Dioxide Laser for Treatment of Decorative Tattoos Clinical and Pathological Observations", *Lasers Surg. Med.*, 3:183 (Abstract No. 294) (1983).

Apfelberg et al., Dot or Pointillistic Method for Improvement in Results of Hypertrophic Scarring in the Argon Laser Treatment of Portwine Hemangiomas,*Lasers Surg. Med.*, 6:552–558 (1987).

Apfelberg et al., "Investigation of YAG Laser Uses in Plastic Surgery",*Lasers Surg.*, 6:246 (Abstract No. 77) (1986).

Apfelberg et al., "Preliminary Investigation of KTP/532 Laser Light in the Treatment of Hemangiomas and Tattoos", *Lasers Surg. Med.*, 6:38–42 (1986).

Apfelberg et al., "Progress Report on Extended Clinical Use of the Argon Laser for Cutaneous Lesions", *Lasers Surg. Med.*, 1:71–83 (1980).

Apfelberg et al., "Progress Report on Multicenter Study of Laser–Assisted Liposuction", *Aesth. Plast. Surg.*, 18:259–264 (1994).

Apfelberg et al., "Results of Argon and CO2 Laser Exposure of Telangiectasia of the Lower Extremity: A Preliminary Report", *Lasers Surg. Med.*, 3:149 (Abstract No. 165) (1983).

Apfelberg et al., "Study of Three Laser Systems for Treatment of Superficial Varicosities of the Lower Extremity", *Lasers Surg. Med.*, 7:219–223 (1987).

Apfelberg et al., "Superpulse $CO_2$ Laser Treatment of Facial Syringomata", *Lasers Surg. Med.*, 7:533–537 (1987).

Apfelberg et al., "Update on Laser Usage in Treatment of Decorative Tattoos",*Lasers Surg. Med.*, 2:169–177 (1982).

Apfelberg, D.B., "Intralesional Laser Photocoagulation— Steroids as an Adjunct to Surgery for Massive Hemangiomas and Vascular Malformations",*Ann. Plast. Surg.*, 35:144–148 (1995).

Ara et al., "Irradiation of Pigmented Melanoma Cells with High Intensity Pulsed Radiation Generates Acoustic Waves and Kills Cells", *Lasers Surg. Med.*, 10:52–59 (1990).

Ashinoff et al., "Cappillary Hemangiomas and Treatment with the Flash Lamp–Pumped Pulsed Dye Laser", *Arch. Dermatol.*, 127:202–205 (1991).

Ashinoff et al., "Flashlamp–pumped pulsed dye laser for port–wine stains in infancy: Earlier versus later treatment", *J. Am. Acad. Dermatol.*, 24:467–472 (1991).

Bell et al., "100 μsec pulsed $CO_2$ laser resurfacing of lower eyelids: Erythema and rhytides reduction", *SPIE*, 2970:360–366 (1997).

Broska et al., "Comparison of the Argon Tunable Dye Laser with the Flashlamp Pulsed Dye Laser in Treatment of Facial Telangiectasia", *J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–594 (1991).

Burson et al., "Gel de Transmission de Ultrasonidos: Estudio Comparitivo de Distintas Formulaciones", *Farm Hosp.*, pp. 394–399 (1991) (in Spanish, with English Abstract Only).

Cates, M.C., "A long pulse (5 μs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremities", *J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL",*J. Cutan. Laser Ther.*, 1:101–104 (1999).

Cole–Beuglet et al., "Ultrasound mammography for the Augmented Breast",*Radiology*, 146:737–742 (1983).

Colver et al., "Port Wine Stains", *J. Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "A History of Photodynamic Therapy",*Aust. N. Z. J. Surg.*, 61:340–348 (1991).

Denham et al., "Light Distribution in Laser Irradiated Tissue",*Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulos et al., "High–energy Short–pulse Flashlamps: Operating Characteristics",*Applied Optics*, 16:70–75 (1977).

Ell et al., "Laser Lithotripsy of Gallstone by Means of a Pulse d Neodymium YAG Laser—In Vitro and Animal Experiments",*Endoscopy*, 18:92–94 (1986).

Englehardt et al., "Spectroscopy During Laser Induced Shock Wave Lithotripsy",*SPIE*, 906:200–240 (1988).

Fitzpatrick et al., "Flashlamp–pumped Pulsed Dye Laser Treatment of Port–Wine Stains",*J. Dermatol. Surg. Oncol.*, 20:743–748 (1994).

Fitzpatrick et al., "Treatment of Leg Veins: A Comparison of Laser Therapy with a Noncoherent, Multiwave Light Source", *Proc. Ann. Meeting IEEE Lasers & Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study",*Lasers Med. Sci.*, 8:185–196 (1993).

Foster et al., "The Successful Use of the PhotoDerm VL in the Treatment of a Cavernous Hemangioma in a Dark– Skinned Infant",*Minimally Invasive Surgical Nursing*, 10:102–104 (1996).

Garden et al., "Effect of Dye Laser Pulse Duration on Selective Cutaneous Vascular Injury",*J. Invest. Dermatol.*, 87(5):653–657 (1986).

Garden et al., "The Treatment of Port–wine Stains by the Pulsed Dye Laser: Analysis of Pulse Duration and Long– term Therapy",*Arch. Dermatol.*, 124:889–896 (1988).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Lasers Surg. Med.*, 11:287–296 (1991).

Gijsbers et al., "Effect of Force on Ablation Depth for a XeCl Excimer Laser Beam Delivered by an Optical Fiber in Contact with Arterial Tissue Under Saline", *Lasers Surg. Med.*, 12:576–584 (1992).

Gilbert, D.J., "Incorporating Photodynamic Therapy Into a Medical and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long Term Hair Removal", *J. Cutan. Laser Ther.*, 1:167–171 (1999).

Gold et al., "Treatment of Wrinkles and Skin Tightening Using Aluma™ Skin Renewal System with Faces™ (Functional Aspiration Controlled Electrothermal Stimulation) Technology",*Aesthetic Buyers Guide*, pp. 1–6 (2005).

Gold, M.H., "Aminolevulinic Acid Photodynamic Therapy: Medical Evidence for Its Expaned Use", *Expert Rev. Med. Devices*, 3:357–371 (2006).

Gold, M.H., "Introduction to Photodynamic Therapy: Early Experience", *Dermatol. Clin.*, 25:1–4 (2007).

Goldberg et al., "Nonablative Treatment of Rhytids With Intense Pulsed Light", *Lasers Surg. Med.*, 26:196–200 (2000).

Goldberg et al., "Q–switched Nd:YAG Laser: Rhytid Improvement by Non–Ablative Dermal Remodeling", *J. Cutan. Laser Ther.*, 2:157–160 (2000).

Goldberg, D.J., "Effect of Temperature–Controlled Cooling on Light–Based Skin Treatments", *J. Cos. Laser Ther.*, 8:155–156 (2006).

Goldberg, D.J., "Erbium: YAG Laser Resurfacing: What Is Its Role?",*Aesth. Surg. J.*, 18(4):255–260 (1998).

Goldberg, D.J., "New Collagen Formation After Dermal Remodeling with an Intense Pulsed Light Source", *J. Cutan. Laser Ther.*, 2:59–61 (2000).

Goldman et al., "600 nm Flash Pumped Dye Laser for Fragile Telangiectasia of the Elderly",*Lasers Surg. Med.*, 13:227–233 (1993).

Goldman et al., "Photothermal Sclerosis of Leg Veins", *Dermatol. Surg.*, 22:323–330 (1996).

Goldman et al., "Pulsed dye laser treatment of telangiectases with and without subtherapeutic sclerotherapy", *J. Am. Acad. Dermatol.*, 23(1):23–30 (1990).

Goldman et al., "Treatment of Cutaneous Vascular Lesions", in *Cutaneous Laser Surgery*, Chapter 2, pp. 19–105 (1994).

Goldman et al., "Treatment of port–wine stains (capillary malformation) with the flashlamp–pumped pulsed dye laser", *J. Pediatrics*, 122(1):71–77 (1993).

Goldman, M.P., "Laser and Noncoherent Pulsed Light Treatment of Leg Telangiectasia and Venules", *Cos. Dermatol.*, 8(10):43–44 (1995).

Goldman, M.P., "Sclerotherapy Treatment for Varicose and Telangiectatic Leg Veins", in *Vascular and Pigmented Abnormalities*, Chapter 17, pp. 256–271 (1997).

Gomer, H., "Military laser burns away skin flaws",*The London Sunday Times*, No. 8929 (Oct. 15, 1995).

Gonzalez et al., "Treatment of telangiectases and other benign vascular lesions with the 577 nm pulsed dye laser", *J. Am. Acad. Dermatol.*, 27(2):220–226 (1992).

Gregory et al., "Effect of Blood Upon the Selective Ablation of Atherosclerotic Plaque with a Pulsed Dye Laser", *Lasers Surg. Med.*, 10:533–543 (1990).

Grevelink et al., "Update on the Treatment of Benign Pigmented Lesions with the Q–Switched Ruby Laser",*Lasers Surg. Med.*, 4:73–74 (Abstract No. 326) (1992).

Groot et al., "Comparison of the infrared coagulator and the carbon dioxide laser in the removal of decorative tattoos", *J. Am. Acad. Dermatol.*, 15:518–522 (1986).

Guttman, C., "Novel radiofrequency–based treatment achieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE*, 2671:211–218 (1996).

Henderson, B.W., "Photodynamic therapy—coming of age", *Photodermatology*, 6:200–211 (1989).

Henning et al., "Clinical and Histological Evaluation of Portwine Stain Treatment with a Microsecond pulsed Dye–laser at 577 NM", *Lasers Surg. Med.*, 4:375–380 (1984).

Henning et al., "Port Wine Stain Coagulation Experiments with a 540–nm Continuous Wave Dye–laser", *Lasers Surg. Med.*, 2:205–210 (1983).

Henning et al., "Rhinophyma Treated by Argon Laser",*Lasers Surg. Med.*, 2:211–215 (1983).

Henning et al., "Treatment of Keloids and Hypertrofic Scars with an Argon Laser",*Lasers Surg. Med.*, 6:72–75 (1986).

Hilsenrath, J.E., "Investing it; Unsightly Veins? Zap. Wall St. Woes? Zap.",*New York Times*, http://www.nytimes.com, pp. 1–3 (Jun. 23, 1996).

Hruza et al., "Laser Skin Resurfacing",*Arch. Dermatol.*, 132:451–455 (1996).

Hughes, P.S.H., "Multiple Miliary Osteomas of the Face Ablated With the Erbium: YAG Laser", *Arch. Dermatol.*, 135:378–380 (1999).

"Infrared–Coagulator", Lumatec product leaflet, pp.1–4.

Ishimaru, A., "Diffusion of light in turbid material",*Applied Optics*, 28(12):2210–2215 (1989).

Jacques, S.L., "The Role of Skin Optics in Diagnostic and Therapeutic Uses of Lasers", *Lasers Dermatol.*, pp. 1–21 (1992).

Jaitly et al., "1 MV Long Pulse Generator with Low Ripple and Low Droop",*$8^{th}$ IEEE Int'l Pulsed Power Conf.*, pp. 161–165 (1991).

Jaitly et al., "Design and Testing of Multi–output 300kV Prototype Induction Cell Pulsed Power Supply for Darht", *$10^{th}$ IEEE Int'l Pulsed Power Conf.*, pp. 1412–1421 (1995).

Jay, H.H., "Victory Over Veins", http://www.nytimes.com, pp. 1–2 (Jul. 21, 1996).

Johannigmann et al., "Ein Neues Ultraschall–Kontaktgel", *Geburtsh. U. Frauenheilk*, p. 34 (1974) (in German, with English Abstract Only).

Kalka et al., "Photodynamic Therapy in Dermatology",*J. Am. Acad. Dermatol.*, 42:389–413 (2000).

Kaminester, L.H., "Suntanning Centers",*JAMA*, 244(11):1258–1259 (1980).

Kaufmann et al., "Pulsed 2·94–μm erbium–YAG laser ablation—experimental results and first clinical application", *Clin. Exp. Dermatol.*, 15:389–393 (1990).

Keijzer et al., "Laser Beam Diameter for Port Wine Stain Treatment",*Lasers Surg. Med.*, 11:601–605 (1991).

Kennedy et al., "Photodynamic Therapy with Endogenous Protoporphyrin, IX: Basic Principles and Present Clinical Experience", *J. of Photochem. Photobio.*, 6:143–148 (1990).

Kilmer et al., "Pulse Dye Laser Treatment of Rhytids",*Lasers Surg. Med.*, p. 44 (Abstract No. 194) (1997).

Koechner, W., in *Solid State Laser Engineering*, Springer Series in Optical Sciences—vol. 1, Chapters 1–2, pp. 1–620, Springer–Verlag, New York (1976).

Lakmaker et al., "Modeling the Color Perception of Port Wine Stains and its Relation to the Depth of Laser Coagulated Blood vessels", *Lasers Surg. Med.*, 13:219–226 (1993).

Lash et al., "How We Got Here", *Lasers Surg. Med.*, 3:113 (Abstract No. 29) (1983).

Lask et al., "Laser Skin Resurfacing with the SikTouch Flashscanner for Facial Rhytides", *Dermatol. Surg.*, 21:1021–1024 (1995).

Lask et al., "Nonablative laser treatment of facial rhytides", *SPIE*, 2970:338–349 (1997).

Levins et al., "Q–Switched Ruby Laser Treatment of Tattos", *Lasers Surg Med.*, Suppl. 3:63–64 (Abstract No. 255) (1991).

Lowe et al., "Skin Resurfacing with the Ultrapulse Carbon Dioxide Laser", *Dermatol. Surg.*, 21:1025–1029 (1995).

Magee et al., "Vein Marking Through Ultrasound Coupling Gel", *Eur. J. Vasc. Surg.*, 4:491–492 (1990).

Majaron et al., "Deep Coagulation of Dermal Collagen with Repetitive Er:YAG Laser Irradiation", *Lasers Surg. Med.*, 26:215–222 (2000).

Majaron et al., "Er:YAG Laser Skin Resurfacing Using Repetitive Long–Pulse Exposure and Cryogen Spray Cooling: I. Histological Study",*Lasers Surg. Med.*, 28:121–130 (2001).

Majaron et al., "Er:YAG Laser Skin Resurfacing Using Repetitive Long–Pulse Exposure and Cryogen Spray Cooling: II. Theoretical Analysis",*Lasers Surg. Med.*, 28:131–137 (2001).

Margolis et al., "Visible Action Spectrum for Melanin–Specific Selective Photothermolysis",*Lasers Surg. Med.*, 9:389–397 (1989).

Marhic et al., "White–Light Flashlamp–pumped dye laser for photography through endoscopes",*Optics Communications*, 45(1):21–25 (1983).

McCaughan et al., "Photodynamic Therapy for Cutaneous and Subcutaneous Malignant Neoplasms", *Arch. Surg.*, 124:211–216 (1989).

McCaughan et al., "Photodynamic Therapy: An Eight–Year Experience", in *Photodynamic Therapy: Basic Principles and Clinical Applications*, pp. 323–331 (1992).

Meijering et al., "Limits of Radial Time Constants to Approximate Thermal Response of Tissue", *Lasers Surg. Med.*, 13:685–687 (1993).

Miller et al., "Optical Modelling of Light Distributions in Skin Tissue Following Laser Irradiation", *Lasers Surg. Med.*, 13:565–571 (1993).

Milner et al., "Analysis of nonablative skin resurfacing", *SPIE*, 2970:367–377 (1997).

Mordon et al., "Rationale for Automatic Scanners in Laser Treatment of Port wine Stains",*Lasers Surg. Med.*, 13:113–123 (1993).

Morelli et al., "Tunable Dye Laser (577 nm) Treatment of Port Wine Stains",*Lasers Surg. Med.*, 6:94–99 (1986).

Motamedi et al., "Thermal Response of Tissue During Laser Angioplasty", *Lasrers Surg. Med.*, 5:172 (Abstract No. 114) (1985).

Mutzhas et al., "A New Apparatus with High Radiation Energy Between 320–460 nm: Physical Description and Dermatological Applications",*J. Invest. Dermatol.*, 76:42–47 (1981).

Nakagawa et al., "Ultrastructural Changes in Human Skin After Exposure to a Pulsed Laser",*J. Invest. Dermatol.*, 84(5):396–400 (1985).

Nestor et al., "New Perspectives on Photorejuvenation",*Skin & Aging*, 11:68–74 (2003).

Newman et al., "Variable Pulse Erbium: YAG Laser Skin Resurfacing of Perioral Rhytides and Side–by–side Comparison with Carbon Dioxide Laser",*Lasers Surg. Med.*, 26:208–214 (2000).

Parrish et al., "Exploring Mechanisms of Specificity in Laser–Tissue Interactions", *Lasers Surg. Med.*, 3:175 (Abstract No. 260) (1983).

Parrish et al., "Spatial Confinement of Thermal Effects of Pulsed Laser Irradiation of Tissue",*Lasers Surg. Med.*, 3:157 (Abstract No. 195) (1973).

Paul et al., "The Effect of Temperature and Other Factors on Selective Microvascular Damage Caused by Pulsed Dye Laser",*J. Invest. Dermatol.*, 81(4):333–336 (1983).

Pfefer et al., "Mechanisms of Laser–Induced Thermal Coagulation of Whole Blood in vitro", *SPIE*, 3590:20–31 (1999).

Philipp et al., "Treatment of Congenital Vascular Disoders: Classification, Step Programme and Therapeutical Procedures",*SPIE*, 2086:228–238 (1993).

Pickering et al., "585 nm for the Laser Treatment of Port Wine Stains: A Possible Mechanism",*Lasers Surg. Med.*, 11:616–618 (1991).

Plewig et al., "A new apparatus for the delivery of high intensity UVA and UVA + UVB irradiation, and some dermatological applications",*Br. J. Dermatol.*, 98:15–24 (1978).

Polla et al., "Tunable Pulsed Dye Laser for the Treatment of Benign Cutaneous Vascular Ectasia", *Dermatologica*, 174:11–17 (1987).

Pottier et al., "Assessment of Non–Coherent Light Sources for Photodynamic Therapy",*SPIE*, 2371:364–368 (1995).

Pratesi, R., "Potential Use of Incoherent and Coherent Light–Emitting–Diodes (LEDs) in Photomedicine", in *Photomedicine, Laser Photobiol. Photomed.*, 22:293–38 (1983).

Ramrus et al., "A Compact One–Half MV Rep–Rate Pulser", *20$^{th}$ IEEE Power Modulator Symposium*, pp. 68–71 (1992).

Ramrus et al., "Design and Performance of a One–Half MV Rep–Rate Pulser", Proc. Of the 8$^{th}$ IEEE International Pulsed Power Conference, pp. 982–985 (1991).

Ranganathan et al., "Promises for Ultrasonic Waves on Activity of Silica Gel and Some Supported Catalystes",*Ind. Eng. Chem. Prod. Res. Develop.*, 12:155–158 (1973).

Rassing et al., "Measurement of Ultrasonic Absorption in a Gel by Light Diffraction and Resonator Methods",*J. Mol. Liq.*, 26:97–108 (1983).

Rastegar et al., "Technique for Measurement of One–Dimensional Instantaneous Ablation Velocity", *Lasers Surg. Med.*, 8:533–535 (1988).

Raulin et al., "Treatment of a Nonresponding Port–Wine Stain With a New Pulsed Light Source (PhotoDerm® VL)", *Lasers Surg. Med.*, 21:203–208 (1997).

Raulin et al., "Treatment of Adult Port–Wine Stains Using Intense Pulsed Light Therapy (PhotoDerm VL): Brief Initial Clinical Report",*Dermatol. Surg.*, 23:594–601 (1997).

Raulin et al., "Treatment of benign venous malformations with an intense pulsed light source (PhotoDerm VL)", *Eur. J. Dermatol.*, 7:279–282 (1997).

Raulin et al., "Treatment of Essential Telangiectasias with an Intense Pulsed Light Source (PhotoDerm VL)",*Dermatol. Surg.*, 23:941–946 (1997).

Raulin et al., "Treatment of Port–wine Stains With a Noncoherent Pulsed Light Source",*Arch. Dermatol.*, 135:679–683 (1999).

Reyes et al., "Treatment of port–wine stains during childhood with the flashlamp–pumped pulsed dye laser", *J. Am. Acad. Dermatol.*, 23:1142–1148 (1990).

Ross et al., "Effects of CO₂ Laser Pulse Duration in Ablation and Residual Thermal Damage: Implications for Skin Resurfacing",*Lasers Surg. Med.*, 19:123–129 (1996).

Rowe, P.M., "Photodynamic therapy begins to shine",*Lancet*, 351:1496 (1998).

Sadick et al., "Photorejuvenation with Intense Pulsed Light: Results of a Multi–Center Study",*J. Drugs Dermatol.*, 3(1):41–49 (2004).

Sadick, N.S., "A Structural Approach to Nonablative Rejuvenation",*Cosmetic Dermatol.*, 15(12):39–43 (2002).

Sadick, N.S., "Update on Non–Ablative Light Therapy for Rejuvenation: A Review",*Lasers Surg. Med.*, 32:120–128 (2003).

Schamiloglu et al., "Modern Pulsed Power: Charlie Martin and Beyond",*Proceedings of the IEEE*, 92(7):1014–1020 (2004).

Schroeter et al., "An Intense Light Source: The Photoderm VL–Flashlamp as a New Treatment Possibility for Vascular Skin Lesions",*Dermatol. Surg.*, 24:743–748 (1998).

Schroeter et al., "Clinical significance of an intense, pulsed light source on leg telangiectasias of up to 1mm diameter", *Eur. J. Dermatol.*, 7:38–42 (1997).

Schroeter et al., "Photoderm VL treatment of leg teleangiectasia",*JEADV*, 5(Suppl. 1):S49 (Abstract No. W76) (1995).

Schwimer et al., "The Effect of Ultrasound Coupling Gels on Sperm Motility In Vitro",*Fertil. Steril.*, 42:946–947 (1984).

Sheean et al., "Arrest of Embryo Development by Ultrasound Coupling Gels",*Fertil. Steril.*, 45:568–571 (1986).

Smith et al., "532–Nanometer Green Laser Beam Treatment of Superficial Varicosities of the Lower Extremities",*Lasers Surg. Med.*, 8:130–134 (1988).

Steiger et al., "Comparison of Different Pulsed and Q–switched Solid–state Laser Systems for Endoscopic Laser Induced Shock Wave Lithotripsy: Performance and Laser/Stone Interaction", *SPIE*, 2300:94–101 (1990).

Strickland et al., "A 5kV, 250 kA Rep–Rated Pulser Using Parallel Ignitrons", *7th IEEE Int'l Pulsed Conf.*, pp. 729–731 (1989).

Sunde et al., "Traumatic Tattoo Removal: Comparison of Four Treatment Methods in an Animal Model with Correlation to Clinical Experience", *Lasers Surg. Med.*, 10:158–164 (1990).

Svaasand et al., "Light and Drug Distribution with Topically Administered Photosensitizers",*Lasers Surg. Med.*, 11:261–265 (1996).

Szeimies et al., "A Possible New Incoherent Lamp for Photodynamic Treatment of Superficial Skin Lesions", *Acta Derm. Venereol (Stockh).*, 74:117–119 (1994).

Tan et al., "Action Spectrum of Vascular Specific Injury Using Pulsed Irradiation",*J. Invest. Dermatol.*, 92(6):868–871 (1989).

Tan et al., "EMLA for Laser Treatment of Portwine Stains in Children",*Lasers Surg. Med.*, 12:543–548 (1992).

Tan et al., "Histologic Responses of Port–wine Stains Treated by Argon, Carbon Dioxide, and Tunable Dye Lasers",*Arch. Dermatol.*, 122:1016–1022 (1986).

Tan et al., "Pulsed Dye Laser Treatment of Recalcitrant Verrucae: A Preliminary Report",*Lasers Surg. Med.*, 13:127–137 (1993).

Tan et al., "Treatment of Children with Port–Wine Stains Using the Flashlamp–Pulsed Tunable Dye Laser",*N. Engl. J. Med.*, 320(7):416–421 (1989).

Taub, A.F., "Photodynamic Therapy: Other Uses",*Dermtol. Clin.*, 25:101–109 (2007).

Taylor et al., "Q–Switched Ruby Laser (QSRL) Irradiation of Benign Pigmented Lesions: Dermal vs. Epidermal", *Lasers Surg. Med.*, 3:65 (Abstract No. 262) (1991).

Templeton et al., "Comparison of infrared coagulation and rubber band ligation for first and second degree haemorrhoids: a randomized prospective clinical trial",*Br. Med. J.*, 286:1387–1389 (1983).

Troccoli et al., "Multiple–Pulse Photocoagulation of Blood Vessels With A 585 Nm Tunable Laser", *Lasers Surg. Med.*, 4:3 (Abstract No. 2) (1992).

van Gemert et al., "Can Physical Modeling Lead to an Optimal Laser Treatment Strategy for Port Wine Stains", in *Laser Applications in Medicine and Biology*, Chapter 5, pp. 199–247, Plenum Press, New York (1991).

van Germert et al., "Instantaneous Ablation Behavior of In–Vitro Rods During Laser Irradiation", *Lasers Surg. Med.*, 5:136 (Abstract No. 4) (1985).

van Germert et al., "Is There an Optimal Laser Treatment for Port Wine Stains?",*Lasers Surg. Med.*, 6:76–83 (1986).

van Germert et al., "Wavelengths for Laser Treatment of Port Wine Stains and Telangiectasia", *Lasers Surg. Med.*, 16:147–155 (1995).

"Varicose Vein Device Producer comes to U.S. Market", *Clinica*, 687:9 (Jan. 8, 1996).

Venning et al., "Tattoo removal using infra–red coagulation: a dose comparison",*Br. J. Dermatol.*, 117:99–105 (1987).

Wagner et al., "Percutalgine–Gel et Ultrasonotherapie en Pathologie du Sport",*La Revue de Medecine*, 32:1681–1683 (1982) (in French, with English Abstract Only).

Waldorf et al., "Skin Resurfacing of Fine to Deep Rhytides Using a Char–free Carbon Dioxide Laser in 47 Patients", *Dermatol. Surg.*, 21:940–946 (1995).

Walsh et al., "Er:YAG Laser Ablation of Tissue: Measurement of Ablation Rates",*Lasers Surg. Med.*, 9:327–337 (1989).

Walsh et al., "Pulsed CO₂ Laser Tissue Ablation: Effect of Tissue Type and Pulse Duration On Thermal Damage",*Lasers Surg. Med.*, 8:108–118 (1988).

Walsh, J.T., "Er:YAG Laser Ablation of Tissue: Effect of Pulse Duration and Tissue Type on Thermal Damage",*Lasers Surg. Med.*, 9:314–326 (1989).

Walsh, J.T., "Pulsed Laser Ablation of Tissue: Analysis of the Removal Process and Tissue Healing", *Unpublished Ph.D. dissertation Massachusetts Institute of Technology, on file with Institute Archives and Hayden Library, Massachusetts Institute of Technology*, pp. 1–312 (1988).

Weiss et al., "Rejuvenation of Photoaged Skin: 5 Years Results with Intense Pulsed Light of the Face, Neck, and Chest",*Dermatol. Surg.*, 28:1115–1119 (2002).

Welch et al., "Practical Models for Light Distribution in Laser–Irradiated Tissue", *Lasers Surg. Med.*, 6:488–493 (1987).

Werner et al., "Die Hamangiombehandlung mit dem Neodym: Yttrium–Aluminium–Granat Laser (Nd:YAG–Laser)", *Laryngo–Rhino–Otol.*, 71:388–395 (1992), (in German, with English Abstract Only).

West, T., "How Laser Surgery Can Help Your Rosacea Patients",*Skin & Aging*, 43–46 (1998).

Wilder, D., "Pulsed 1064–nm Nd:YAG Laser Therapy for Noninvasive Treatment of a Massive Hemangioma: Case Report", *J. Clin. Laser Med. Surg.*, 17(6):245–247 (1999).

Wilson et al., "The physics of photodynamic therapy", *Phys. Med. Biol.*, 31(4):327–360 (1986).

Gros, et al, Diaphanologie Mammaire, Memoires Originaux, *J. Radiol. Electrol.*, 53(4):297–306 (1972), in French, with English translation.

Brochure for an Infrared Coagulator by Redfield Corporation (1968).

*Groot & Johnson*, "Lasers and Advanced Dermatological Instrumentation", *Australas J. Dermatol.*, 28:77–85 (1987).

Kaufmann et al., "Pulsed Er: YAG– and 308 nm UV–Excimer Laser: An In Vitro and In Vivo Study of Skin–Ablative Effects", Laser Surg. Med., 9:132–140 (1989).

Lasers and Advanced Dermatological Instrumentation by Groot and Johnson, Australas Dermatol 1987.

"The Infrared Coagulator in Dermatology," by Graham Colver, Dermatologic Clinics, vol. 7, No. 1, pp. 155–167, 1989.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13, 16, 17 and 18 is confirmed.

Claims 2–7, 9 and 12 were previously cancelled.

Claims 1, 14, 15 and 26 are determined to be patentable as amended.

Claims 8, 10, 11, 19–25 and 27–32, dependent on an amended claim, are determined to be patentable.

New claims 33–36 are added and determined to be patentable.

1. A therapeutic treatment device comprising:
a flashlamp operable to provide a pulsed light output having a spectrum of frequencies continuous over at least one bandwidth for treatment, *wherein the pulsed light output is configured to cause heat to penetrate a skin treatment area*;
a hand-held housing unit defining an opening and containing the flashlamp, the hand-held housing unit suitable for being disposed adjacent [a] *the* skin treatment area and for treating an area of at least 2.5 square centimeters;
at least one optical filter mounted within the hand-held housing unit; and
a control box including a variable pulse-width pulse forming circuit electrically connected to the flashlamp via at least a flexible cable, wherein the flashlamp and the at least one optical filter are configured to provide pulses having a pulse width in the range of about 5–20 milliseconds and an energy density of the light on the skin of about 6–20 Joules per square centimeter, *wherein the control box is configured to control a depth of penetration of the heat as a function of the pulse width and a thermal property of the skin treatment area*; and
a reflector mounted within the hand-held housing unit and proximate the light source.

14. A method of treatment with light energy comprising:
providing a pulsed light output having a spectrum of frequencies continuous over at least one bandwidth using a flashlamp;
locating a hand-held unit including a light guide, a filter, and the flashlamp adjacent to an area of skin;
filtering the pulsed light output to control the spectrum of the pulsed light output;
directing the pulsed light output to a least a 2.5 square centimeter area that includes skin irregularities, wherein the pulsed light travels through the filter *and causes heat penetration in the area of skin*;
cooling the flashlamp with water;
focusing the flashlamp for controlling the power density of the pulsed light output; [and]
controlling the pulse-width of the pulsed light output via a pulse forming circuit disposed in a control box and operably coupled to the hand-held unit via a flexible cable;
*controlling a depth of the penetration of the heat as a function of a pulse width and a thermal property of the area of skin; and*
wherein controlling the pulse-width includes providing a pulse-width in the range of about 5 milliseconds to 20 milliseconds, and an energy density within 6–20 Joules per square centimeter, whereby blood vessels are coagulated.

15. A method of treatment with light energy comprising:
providing a pulsed light output from a flashlamp;
locating a hand-held unit including a light guide, a filter, and the flashlamp adjacent to an area of skin;
directing the pulsed light output to a treatment area of at least 2.5 square centimeters;
controlling the pulse-width of the pulsed light output *as a function of a desired depth of heat penetration of the area of skin*;
focusing the light source for controlling the power density of the pulsed light output;
filtering and controlling the spectrum of the pulsed light output;
providing a fluorescent material within the hand-held unit and between the flashlamp and the skin treatment area;
absorbing radiation in the fluorescent material, the radiation being emitted by the flashlamp;
emitting radiation from the fluorescent material, the radiation having a wavelength in the range of about 550–650 nm; and
absorbing radiation in the wavelength range substantially less than 500 nm.

26. An apparatus for providing light to the skin, comprising:
a hand-held unit including a flashlamp, a fluorescent material, a filter and a light guide;
a control box including a power supply and a pulse-width forming circuit;
a flexible cable configured to connect the hand-held unit to the control box,
wherein the hand-held unit is configured to be disposed adjacent to the skin and configured to direct light to at least a 2.5 square centimeter area of skin, the filter is configured to transmit light having a wavelength of about 500–650 nm to the skin, and the pulse-width forming circuit is configured to pulse the flashlamp for about 10 to 15 milliseconds, wherein the energy density of the light on the skin is about 6 to 20 Joules per square centimeter; and
a reflector mounted in the hand-held unit and proximate to the flashlamp,
*wherein the pulse-width forming circuit is configured to control the flashlamp as a function of a desired depth of heat penetration of the skin.*

33. A therapeutic treatment device comprising:
*a plurality of flashlamps operable to provide a pulsed light output having a spectrum of frequencies continuous over at least one bandwidth for treatment;* a hand-held housing unit defining an opening and containing the flashlamps, the hand-held housing unit suitable for being disposed adjacent a skin treatment area and for treating an area of at least 2.5 square centimeters;

at least one optical filter mounted within the hand-held housing unit;

a control box including a variable pulse-width pulse forming circuit electrically connected to the flashlamps via at least a flexible cable, wherein the flashlamps and the at least one optical filter are configured to provide pulses having a pulse width in the range of about 5–20 milliseconds and an energy density of the light on the skin of about 6–20 Joules per square centimeter; and a reflector mounted within the hand-held housing unit and proximate the flashlamps.

34. An apparatus for providing light to the skin, comprising:

a hand-held unit including a plurality of flashlamps, a fluorescent material, a filter and a light guide;

a control box including a power supply and a pulse-width forming circuit;

a flexible cable configured to connect the hand-held unit to the control box, wherein the hand-held unit is configured to be disposed adjacent to the skin and configured to direct light to at least a 2.5 square centimeter area of skin, the filter is configured to transmit light have a wavelength of about 500–650 nm to the skin, and the pulse-width forming circuit is configured to pulse the flashlamps for about 10 to 15 milliseconds, wherein the energy density of the light on the skin is about 6 to 20 Joules per square centimeter; and a reflector mounted in the hand-held unit and proximate to the flashlamps.

35. The treatment device of any one of claims 8, 10, 11, or 20–25, wherein the hand-held unit includes two flashlamps.

36. The method of any one of claims 27, 28, or 30–32 further comprising at least another flashlamp in the hand-held unit.

* * * * *